US011203013B2

(12) United States Patent
Davis et al.

(10) Patent No.: US 11,203,013 B2
(45) Date of Patent: Dec. 21, 2021

(54) ENANTIOMERICALLY ENRICHED, POLYCRYSTALLINE MOLECULAR SIEVES

(71) Applicants: California Institute of Technology, Pasadena, CA (US); William Marsh Rice University, Houston, TX (US)

(72) Inventors: Mark E. Davis, Pasadena, CA (US); Stephen Kramer Brand, Pasadena, CA (US); Joel E. Schmidt, Utrecht (NL); Michael W. Deem, West University Place, TX (US)

(73) Assignees: California Institute of Technology, Pasadena, CA (US); William Marsh Rice University, Houston, TX (US)

( * ) Notice: Subject to any disclaimer, the term of this patent is extended or adjusted under 35 U.S.C. 154(b) by 641 days.

(21) Appl. No.: 15/875,245

(22) Filed: Jan. 19, 2018

(65) Prior Publication Data

US 2018/0207625 A1 Jul. 26, 2018

Related U.S. Application Data

(60) Provisional application No. 62/448,424, filed on Jan. 20, 2017, provisional application No. 62/475,656, filed on Mar. 23, 2017.

(51) Int. Cl.
*B01J 29/04* (2006.01)
*B01J 31/02* (2006.01)
*C07D 233/66* (2006.01)
*B01J 35/00* (2006.01)
*G01N 23/20* (2018.01)
*G01R 33/46* (2006.01)

(52) U.S. Cl.
CPC ......... *B01J 29/047* (2013.01); *B01J 31/0244* (2013.01); *B01J 35/002* (2013.01); *C07D 233/66* (2013.01); *C07B 2200/07* (2013.01); *C07C 2529/04* (2013.01); *G01N 23/20075* (2013.01); *G01R 33/46* (2013.01)

(58) Field of Classification Search
CPC .... B01J 29/047; B01J 31/0244; B01J 35/002; C07D 233/66
See application file for complete search history.

(56) References Cited

U.S. PATENT DOCUMENTS

| | | | |
|---|---|---|---|
| 3,454,626 A | 7/1969 | Gottstein | |
| 4,554,262 A | 11/1985 | Dessau | |
| 4,910,006 A | 3/1990 | Zones et al. | |
| 5,316,753 A | 5/1994 | Yumi | |
| 5,414,078 A | 5/1995 | Liotta et al. | |
| 5,869,706 A | 2/1999 | Dartt et al. | |
| 6,239,315 B1 | 5/2001 | Mueller et al. | |
| 7,138,099 B1 | 11/2006 | Zones et al. | |
| 8,115,001 B2 | 2/2012 | Corma et al. | |
| 9,604,197 B2 | 3/2017 | Schmidt et al. | |
| 9,821,297 B2 | 11/2017 | Boal et al. | |
| 9,861,968 B2 * | 1/2018 | Schmidt | B01J 29/86 |
| 9,908,783 B2 * | 3/2018 | Schmidt | C10G 29/205 |
| 10,293,330 B2 * | 5/2019 | Schmidt | C10G 2/33 |

OTHER PUBLICATIONS

Tang et al., Nature Material, (2008), v.7, p. 381-385.*
Rojas et al., Angew. Chem. Int. Ed., (2012), v.51, p. 3854-3856.*
Brand et al., PNAS, (2017), v.114, p. 5101-5106.*
Tong et al., "Synthesis of chiral polymorph A-enriched zeolite Beta with an extremely concentrated fluoride route", Sci. Rep., 2015, 5, 11521.
Lobo and Davis, "Zeolite and Molecular sieve synthesis", Chem. Mater., 1992, 4(4), 756-768.
Zones, S., Translating new materials discoveries in zeolite research to commercial manufacture. Microporous and Mesoporous Materials, 2011. 144(1): p. 1-8.
Bravo-suárez, J. J.; Chaudhari, R. V; Subramaniam, B. Design of Heterogeneous Catalysts for Fuels and Chemicals Processing: An Overview. In Novel Materials for Catalysis and Fuels Processing; Bravo-Suárez, J. J., Kidder, M. K., Schwartz, V., Eds.; ACS Symposium Series; American Chemical Society: Washington, DC, 2013; vol. 1132, pp. 3-68.
Camblor, M. a.; Corma, A.; Valencia, S. Spontaneous Nucleation and Growth of Pure Silica Zeolite-B Free of Connectivity Defects. Chem. Commun. 1996, No. 20, 2365.
Camblor, M.A., L. Villaescusa, and M. Diaz-Cabanas, Synthesis of all-silica and high-silica molecular sieves influoride media. Topics in Catalysis, 1999. 9(1-2): p. 59-76.
Castillo, J. M.; Vlugt, T. J. H.; Dubbeldam, D.; Hamad, S.; Calero, S. Performance of Chiral Zeolites for Enantiomeric Separation Revealed by Molecular Simulation. J. Phys. Chem. C 2010, 114 (50), 22207-22213.
Cheng, K.; Lee, Y. S.; Rothman, R. B.; Dersch, C. M.; Bittman, R. W.; Jacobson, A. E.; Rice, K. C. Probes for Narcotic Receptor Mediated Phenomena. 41. Unusual Inverse ?—Agonists and Potent ?—Opioid Antagonists by Modification of the N-Substituent in Enantiomeric 5-(3-Hydroxyphenyl)morphans. J. Med. Chem. 2011, 54 (4), 957-969.
Davis, M E., Ordered porous materials for emerging applications. Nature, 2002. 417( 6891): p. 813-21.
Davis, T. M.; Deem, M.; Liu, T.; Xie, D. Computationally-Guided Synthesis of Small-Pore Zeolite SSZ-52. In; Pittsburgh, PA, 2015.
Dryzun, C.; Mastai, Y.; Shvalb, A.; Avnir, D. Chiral Silicate Zeolites. J. Mater. Chem. 2009, 19 (14), 2062.
Eiling, G. R.; Hahn, R. C.; Schwab, G. Cyclopropylarene Chemistry. IV. Homoketenyl Cations in a Friedel-Crafts Acylation. J. Am. Chem. Soc. 1973, 95 (17), 5659-5662.

(Continued)

*Primary Examiner* — Yong L Chu
(74) *Attorney, Agent, or Firm* — BakerHostetler

(57) ABSTRACT

This disclosure describes enantiomerically enriched chiral molecular sieves and methods of making and using the same. In some embodiments, the molecular sieves are silicates or germanosilicates of STW topology.

28 Claims, 11 Drawing Sheets

(7 of 11 Drawing Sheet(s) Filed in Color)

(56) References Cited

OTHER PUBLICATIONS

Hathaway, P. E. and M. E. Davis, High resolution, quasi-equilibrium sorption studies of molecular sieves. Catalysis Letters, 1990. 5(4-6): p. 333-347.
Herse, C.; Bas, D.; Krebs, F. C.; Bürgi, T.; Weber, J.; Wesolowski, T.; Laursen, B. W.; Lacour, J. A Highly Configurationally Stable [4]heterohelicenium Cation. Angew. Chemie—Int. Ed. 2003, 42, 3162-3166.
Inouye, Y.; Sugita, T.; Walborsky, H. M. Cyclopropanes—XVII: The Absolute Configurations of Trans-1,2-Cyclopropanedicarboxylic Acid and Trans-2-Phenylcyclopropanecarboxylic Acid. Tetrahedron 1964, 20 (1961), 1695-1699.
Jo, D.; Hong, S. B.; Camblor, M. a. Monomolecular Skeletal Isomerization of 1-Butene over Selective Zeolite Catalysts ACS Catal. 2015, 2270-2274.
Lacour, J.; Londez, A.; Goujon-Ginglinger, C.; Buss, V.; Bernardinelli, G. Configurational Ordering of Cationic Chiral Dyes Using a Novel C(2)-Symmetric Hexacoordinated Phosphate Anion. Org. Lett. 2000, 2 (Ii), 4185-4188.
Lacour, J.; Vial, L.; Herse, C. Efficient NMR Enantiodifferentiation of Chiral Quats with BINPHAT Anion. Org. Lett. 2002, 4 (Figure 1), 1351-1354.
Lewis, D. W.; Freeman, C. M.; Catlow, C. R. A. Predicting the Templating Ability of Organic Additives for the Synthesis of Microporous Materials. J. Phys. Chem. 1995, 99 (28), 11194-11202.
Lewis, D. W.; Willock, D. J.; Catlow, C. R. A.; Thomas, J. M.; Hutchings, G. J. De Novo Design of Structure-Directing Agents for the Synthesis of Microporous Solids. Nature 1996, 382 (6592), 604-606.
Li, J.; Corma, A.; Yu, J. Synthesis of New Zeolite Structures. Chem. Soc. Rev. 2015.
Li, Y.; Yu, J. New Stories of Zeolite Structures: Their Descriptions, Determinations, Predictions, and Evaluations. Chem. Rev. 2014, 114 (14), 7268-7316.
Lin, L.C., et al., In silica screening of carbon-capture materials. Nat Mater, 2012. 11(7): p. 633-41.
Molander, G. a.; Burke, J. P.; Carroll, P. J. J. Org. Chem. 2004, 69 (5), 8062-8069.
Moliner, M.; Rey, F.; Corma, A. Towards the Rational Design of Efficient Organic Structure-Directing Agents for Zeolite Synthesis. Angew. Chem. Int. Ed. Engl. 2013, 52 (52), 13880-13889.
Morris, R. E.; Bu, X. Induction of Chiral Porous Solids Containing Only Achiral Building Blocks. Nat. Chem. 2010, 2 (5), 353-361.
Nakagawa, Y., et al., Guest/host relationships in zeolite synthesis: ring-substituted piperidines and the remarkable adamantane mimicry by 1-azonio spiro [5.5] undecanes. Microporous and Mesoporous Materials, 1998. 22(1): p. 69-85.
Navrotsky, A.P., A. N., Methods for removing organic compounds from nano-composite materials; U.S. Pat. No. 6,960,327 2005.
Neset, S.; Hope, H.; Undheim, K. Tetrahedron 1997, 53 (30), 10459-10470.
Newsam, J. M.; Treacy, M. M. J.; Koetsier, W. T.; Gruyter, C. B. D. Structural Characterization of Zeolite Beta. Proc. R. Soc. A Math. Phys. Eng. Sci. 1988, 420 (1859), 375-405.
Overberger , Y. Okamoto, V. B. Synthesis and Optical Properties of Asymmetric Polyamides Derived from Optically Active Dicarboxylic Acids and Spirodiamine. Macromolecules 1975, 8 (1), 31-36.
Overberger, C. G.; Shimokawa, Y. Synthesis and Optical Properties of Asymmetric Polyamides Derived from Optically Active Dicarboxylic Acids and Spirodiamine. Macromolecules 1971, 4 (6), 718-725.
Pasquini, C.; Desvergnes-Breuil, V.; Jodry, J. J.; Dalla Cort, A.; Lacour, J. Chiral Anion-Mediated Asymmetric Induction onto Chiral Diquats. Tetrahedron Lett. 2002, 43, 423-426.
Pophale, R.; P.A. Cheeseman, and M.W. Deem, A database of new zeolite-like materials. Phys Chem Chem Phys, 2011. 13(27): p. 12407-12.
Pophale, R.; Daeyaert, F.; Deem, M. W. Computational Prediction of Chemically Synthesizable Organic Structure Directing Agents for Zeolites. J. Mater. Chem. A 2013, 1 (23), 6750-6760.

Publication, A. (±) Trans-3,3'-(1,2-Cyclopropandiyl)Bis-2-(E)-Propenoic Acid, Diethyl Ester: Tandem Oxidation Procedure (TOP) Using MnO2 Oxidation-Stabilized Phosphorane Trapping. Org. Synth. 2008, 85 (September), 15.
Rojas, A.; Arteaga, O.; Kahr, B.; Camblor, M. a. Synthesis, Structure, and Optical Activity of HPM-1, a Pure Silica Chiral Zeolite. J. Am. Chem. Soc. 2013, 135 (32), 11975-11984.
Sastre, G.; Corma, A. Predicting Structural Feasibility of Silica and Germania Zeolites. J. Phys. Chem. C 2010, 114 (3), 1667-1673.
Schmidt, J. E.; Deem, M. W.; Davis, M. E. Synthesis of a Specified, Silica Molecular Sieve by Using Computationally Predicted Organic Structure-Directing Agents. Angew. Chem. Int. Ed. Engl. 2014, 53 (32), 8372-8374.
Schmidt, J. E.; Deem, M. W.; Lew, C.; Davis, T. M. Computationally-Guided Synthesis of the 8-Ring Zeolite AEI. Top. Catal. 2015.
Schmidt, J. E.; Deimund, M. A.; Davis, M. E. Facile Preparation of Aluminosilicate RTH across a Wide Composition Range Using a New Organic Structure-Directing Agent. Chem. Mater. 2014, 26 (24), 7099-7105.
Schmidt, J. E.; Deimund, M. a.; Xie, D.; Davis, M. E. Synthesis of RTH-Type Zeolites Using a Diverse Library of Imidazolium Cations. Chem. Mater. 2015, 27 (10), 3756-3762.
Schmidt, J. E.; Xie, D.; Davis, M. E. High-Silica, Heulandite-Type Zeolites Prepared by Direct Synthesis and Topotactic Condensation. J. Mater. Chem. A 2015, 3, 12890-12897.
Schmidt, J. E.; Xie, D.; Rea, T.; Davis, M. E. CIT-7, a Crystalline, Molecular Sieve with Pores Bounded by 8 and 10-Membered Rings. Chem. Sci. 2015, 6, 1728-1734.
Schmitt, K. D.; Kennedy, G. J. Toward the Rational Design of Zeolite Synthesis: The Synthesis of Zeolite ZSM-18. Zeolites 1994, 14 (8), 635-642.
STW. Available from: iza-structure.org/databases; last updated Feb. 26, 2010.
Sun, J.; Bonneau, C.; Cantín, A.; Corma, A.; Díaz-Cabañas, M. J.; Moliner, M.; Zhang, D.; Li, M.; Zou, X. The ITQ-37 Mesoporous Chiral Zeolite. Nature 2009, 458 (7242), 1154-1157.
Taborda, F.; Willhammar, T.; Wang, Z.; Montes, C.; Zou, X. Synthesis and Characterization of Pure Silica Zeolite Beta Obtained by an Aging-Drying Method. Microporous Mesoporous Mater. 2011, 143 (1), 196-205.
Takagi, Y.; Komatsu, T.; Kitabata, Y. Crystallization of Zeolite Beta in the Presence of Chiral Amine or Rhodium Complex. Microporous Mesoporous Mater. 2008, 109 (1-3), 567-576.
Vermeiren, W. and J.-P. Gilson, Impact of zeolites on the petroleum and petrochemical industry. Topics in Catalysis, 2009. 52(9): p. 1131-1161.
Walborsky, H. M.; Plonsker, L. Cyclopropanes. VIII. Rates of Ring Opening of Substituted Cyclopropyl Ketones and Carbinols. J. Am. Chem. Soc. 1961, 83 (9), 2138-2144.
Yang, Y.; Su, B.; Yan, Q.; Ren, Q. Separation of Naproxen Enantiomers by Supercritical/subcritical Fluid Chromatography. J. Pharm. Biomed. Anal. 2005, 39 (3-4), 815-818.
Yu, J.; Xu, R. Chiral Zeolitic Materials: Structural Insights and Synthetic Challenges. J. Mater. Chem. 2008, 18 (34), 4021.
Brand, et al: "Enantiomerically enriched, polycrystalline molecular sieves", PNAS, May 2017, vol. 114, No. 20, 5101-5106.
Gomez-Hortiguela, et al: "Chiral Organic Structure-Directing Agents", 2017, 1-49.
Ma, et al: Supplementary Information, Electron-crystallography for determining the handedness of a chiral zeolite nano-crystal, Nature Materials 2017, 1-26.
Ma, et al: "Electron crystallography for determining the handedness of a chiral zeolite nanocrystal". Nature Materials, vol. 16, 2017, 755-760.
Rojas, et al: Supporting Information, "A Pure Silica Chiral Polymorph with Helical Pores", Angewandte Chemie 2012, 5 pages.
Rojas, et al.: Supporting Information: Synthesis, Structure, and Optical Activity of HPM-1, a Pure Silica Chiral Zeolite, 2013, 10 pages.
Schmidt, et al: Supporting Information, "Synthesis of a Specified, Silica Molecular Sieve by Using Computationally Predicted Organic Structure-Directing Agents", Angewandte Chemie, 2014, 10 pages.

(56) References Cited

OTHER PUBLICATIONS

Tang, et al: Supplementary Information, "A zeolite family with chiral and achiral structures built from the same building layer", Zou-NM07112238, 2008, 12 pages.

Zhang, et al: "Enantioselective adsorption and diffusion of S-/R-glycidol in homochiral zeolites: A molecular simulation study", Journal of Membrane Science, 367, 2011, 63-70.

* cited by examiner

ENANTIOMERICALLY ENRICHED, POLYCRYSTALLINE MOLECULAR SIEVES

CROSS REFERENCE TO RELATED APPLICATIONS

This application claims priority to U.S. Provisional Patent Application Nos. 62/448,424, filed Jan. 20, 2017 and 62/475,656, filed Mar. 23, 2017, the contents of both of which are incorporated by reference in their entireties.

GOVERNMENT RIGHTS

This invention was made with government support under Grant No. DE-FG02-03ER15456 awarded by the US Department of Energy. The government has certain rights in the invention.

TECHNICAL FIELD

This disclosure describes chiral molecular sieves, including zeolites, and methods of making and using the same.

BACKGROUND

Zeolite and zeolite-like molecular sieves are being used as adsorbents and heterogeneous catalysts to prepare a wide variety of products ranging from gasoline to monomers for polymers such as polyethylene terephthalate (PET) that is used in plastic bottles. Pharmaceuticals, pesticides, fragrances and components in food can contain chiral centers, however, to date, the ability to provide chiral zeolite and zeolite-like molecular sieves that are enantio-enriched so as to provide catalysts for such chiral materials has remained elusive.

Zeolites and zeolite-like molecular sieves have been synthesized using organic structure-directing agents (OSDAs). This synthetic method utilizes an organic molecule (OSDA) to interact with and influence the assembly pathway of the inorganic components to create a crystalline, organic-inorganic composite material. Upon removal of the OSDA, the microporous void space that is created can be exploited in variety of applications; i.e., catalysis, separations, ion exchange and adsorption. These microporous, polycrystalline materials are three-dimensional networks of oxide tetrahedra (zeolites contain only silicon and aluminum, while zeolite-like molecular sieves can have a broader range of elements) that create highly-ordered, hydrothermally-stable framework structures with pores of sizes less than 2 nm. Molecular sieves provide shape-selective properties and, coupled with the inclusion of catalytic active sites, are capable of innumerable, highly selective chemical reactions. Despite the abundance of chirality in nature, the discovery of a zeolite or zeolite-like microporous material with enantioselective properties has remained elusive. Enantioenriched, chiral zeolitic materials are of particular interest for their potential to provide robust, new, enantiospecific, shape-selective catalytic pathways and separation processes. Achievement of the long-standing goal of creating a chiral, polycrystalline molecular sieve with bulk enantio-enrichment would enable these materials to perform enantioselective functions.

The present disclosure is directed to solving this challenge and providing such enantio-enriched molecular sieves.

SUMMARY

The present invention is directed to chiral microporous molecular sieves, and methods of preparing the same. In some embodiments, the enantiomerically enriched, chiral microporous molecular sieves are of STW topology, made using chiral linked di-imidazolium cations.

Some embodiments provide for crystalline microporous solids comprising:
  (a) silicon oxide, germanium oxide, or combination thereof; and optionally
  (b) aluminum oxide, boron oxide, cerium oxide, gallium oxide, hafnium oxide, iron oxide, tin oxide, titanium oxide, indium oxide, vanadium oxide, zirconium oxide, or combination thereof, wherein
  the microporous solid exhibits an enantiomerically enriched, chiral morphology (for example, as determined by HRTEM) and an enantiomeric excess ("ee") of one enantiomer of at least 5%. In some embodiments, the crystalline microporous solid is a pure silicate, an aluminosilicate, a borosilicate, a germanosilicate, or a titanosilicate. In other embodiments, the crystalline microporous solid is a pure aluminosilicate, a pure borosilicate, a pure germanosilicate, or a pure titanosilicate. In some of these embodiments, the crystalline microporous solids having enantiomerically enriched, chiral morphology has STW topology.

The enantiomerically enriched, chiral crystalline microporous solid may contain an Organic Structure Directing Agent (OSDA) occluded within its pores, or may be free from such OSDAs. When present, the OSDA may comprise a structure having a linked pair of imidazolium cations of a structure:

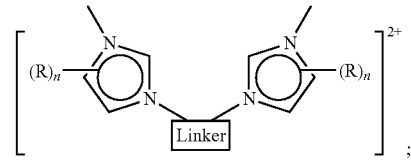

wherein Linker is a 2, 3, 4, 5, or 6-membered chiral linking group, preferably a 4, 5, or 6-membered chiral linking group, including cyclic and alicyclic chiral linking groups, preferably a chiral linking group comprising a saturated cyclic chiral linking group; and
R is independently methyl or ethyl, preferably methyl; and
n is independently 0, 1, 2, or 3, preferably 2 or 3.

In some embodiments, the Linker comprises a chirally substituted cyclopropane, aziridine, epoxide, cyclobutane, cyclopentane, cyclohexane, tetrahydrofuran, pyrrolidine, or tetrahydrothiophene. Exemplary Linker structures are disclosed.

The enantiomerically enriched, chiral crystalline microporous solid may be calcined and exist predominantly in the hydrogen form, or may contain an alkali metal ion, an alkaline earth metal cation, a transition metal or transition metal oxide within its pores.

Other embodiments include processes for preparing such materials, for example comprising hydrothermally treating a composition comprising:
  (a) at least one source of a silicon oxide, germanium oxide, or combination thereof;
  (b) optionally at least one source of aluminum oxide, boron oxide, cerium oxide, gallium oxide, hafnium oxide, iron oxide, tin oxide, titanium oxide, vanadium oxide, zinc oxide, zirconium oxide, or combination or mixture thereof;

(c) either a source of fluoride or a source of hydroxide; and (d) a chiral Organic Structure Directing Agent (OSDA) to produce a crystalline microporous solid having an enantiomerically enriched, chiral morphology. Again, in some of these embodiments, the crystalline microporous solid having an enantiomerically enriched, chiral morphology has STW topology.

In some embodiments, the OSDA comprises a linked pair of quaternary imidazolium cations of a structure:

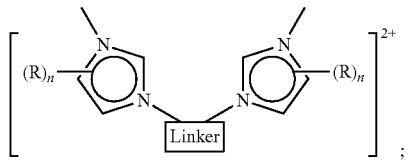

wherein Linker is a 2, 3, 4, 5, or 6-membered chiral linking group, preferably a 4, 5, or 6-membered chiral linking group, including cyclic and alicyclic chiral linking groups, preferably a chiral linking group comprising a saturated cyclic chiral linking group; and R is independently methyl or ethyl, preferably methyl; and n is independently 0, 1, 2, or 3, preferably 2 or 3.

under conditions effective to crystallize a crystalline microporous solid that exhibits an enantiomerically enriched, chiral morphology; i.e., having an enantiomeric excess ("ee") of at least 5%, 10%, 15%, 20%, 25%, 50%, 75%, or 90%. Typically, the conditions are conducive to forming a crystalline microporous silicate composition having STW topology, and may include hydrothermally treating the composition at a temperature in a range of from about 100° C. to about 200° C. for a time effective for crystallizing the crystalline microporous solid.

Some embodiments comprise isolating the enantiomerically enriched, chiral crystalline microporous solid from the hydrothermally treated mixture. The isolated crystalline microporous solid may be calcined and optionally treated with an aqueous ammonium salt or with a alkali metal cation, an alkaline earth metal cation, or at least one transition metal, transition metal salt, or transition metal oxide.

Other embodiments also provide methods selectively separating chiral organic molecules using these inventive enantiomerically enriched, chiral crystalline microporous solid, for example by selectively adsorbing one enantiomer of the organic molecule with an appropriate enantiomerically enriched, chiral crystalline microporous solid.

Still other embodiments provide for the use of these inventive enantiomerically enriched, chiral crystalline microporous solids as catalysts for organic reactions, specifically for the conversion of achiral or prochiral precursors to chiral intermediates or products.

BRIEF DESCRIPTION OF THE DRAWINGS

The application file contains at least one drawing executed in color. Copies of this patent or patent application publication with color drawing(s) will be provided by the Office upon request and payment of the necessary fee.

The present application is further understood when read in conjunction with the incorporated drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. The drawings are as described herein. In the drawings:

FIGS. 7(F-I) shows a comparison of two HRTEM images with gold nanoparticles as markers. A crystal was tilted from [2$\bar{1}\bar{1}$0] (FIG. 7F) to [10$\bar{1}$0] (FIG. 7G) and a shift-down was observed, which indicates a space group of P6522. f-g) The processed images of (FIG. 7 11) and (FIG. 7 1) after Fourier filtering that only includes spatial frequencies within a particular range to enhance the contrasts of gold nanoparticles. Scale bars are 5 nm.

FIGS. 8(A-B) is an image where a crystal was tilted from [2$\bar{1}\bar{1}$0] (a) to [1$\bar{1}$00] (b) and a shift-up was observed, which indicates a space group of P6$_5$22. FIGS. 8(C-D) are the processed images of FIGS. 8(A-B) after Fourier filtering that only includes spatial frequencies within a particular range to enhance the contrasts of gold nanoparticles.

FIGS. 9(A-B) is an image where a crystal was tilted from [2$\bar{1}\bar{1}$0] (a) to [1$\bar{1}$0] (b) and a shift-down was observed, which indicates a space group of P6122. FIGS. 9(C-D) are the processed images of FIGS. 9(A-B) after Fourier filtering that only includes spatial frequencies within a particular range to enhance the contrasts of gold nanoparticles.

FIGS. 10(A-B) is an image where a crystal was tilted from [2$\bar{1}\bar{1}$0] (a) to [10$\bar{1}$0] (b) and a shift-up was observed, which indicates a space group of P6122. FIGS. 10(C-D) are the processed images of FIGS. 10(A-B) after Fourier filtering that only includes spatial frequencies within a particular range to enhance the contrasts of gold nanoparticles.

DETAILED DESCRIPTION OF ILLUSTRATIVE EMBODIMENTS

Figure 1:
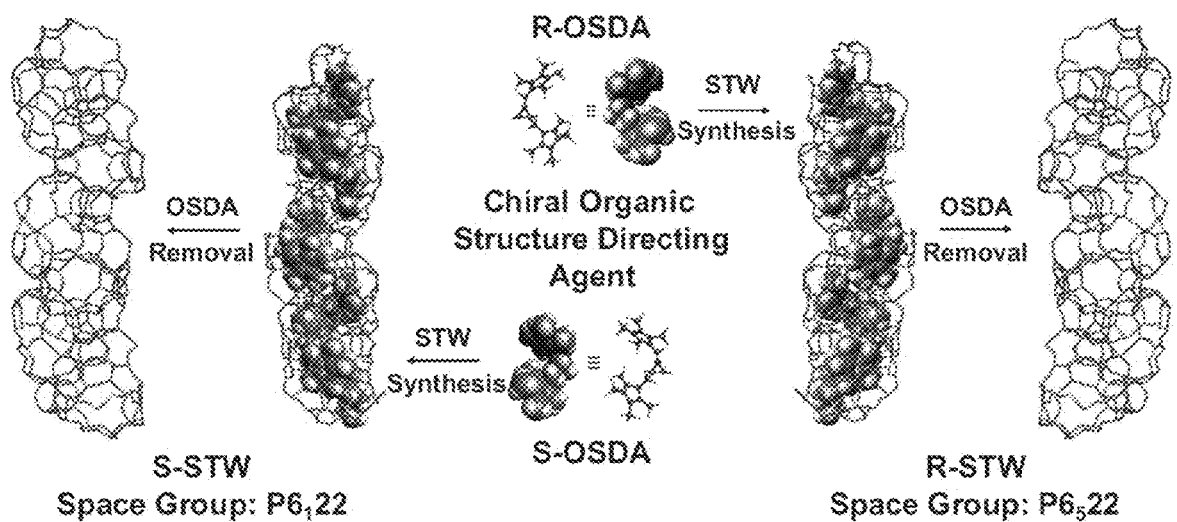
FIG. 1 illustrates the synthesis of enantioenriched STW samples using enantiopure, chiral OSDAs.

The present disclosure is directed to enantiomerically enriched molecular sieves and methods of making and using the same.

The present disclosure includes embodiments of crystalline microporous solid that exhibit chiral morphology, including those enantioenriched with one enantiomer such that the composition exhibits an enantiomeric excess ("ee") of one enantiomer of at least 5%. In other independent embodiments, the enantiomeric excess may be at least 10%, 15%, 20%, 25%, 50%, 75%, or 90% to about 100%. This chiral morphology can be conveniently determined by HRTEM or other methods described herein. The enantiomeric excess may be defined based on the volume or weight of the total microporous crystalline composition and/or may be determined by counting and analyzing a representative number of individual crystals.

While the present disclosure describes the use of rigid, chiral diquat OSDAs to produce the chiral microporous crystalline solids, previous work by at least some of the same inventors used monoquat OSDAs to produce achiral structures of STW topolologies. This work is described in U.S. patent application Ser. No. 14/517,793, filed Oct. 17, 2014, which is incorporated by reference herein for all purposes, but at least for the methods and conditions used to make the STW materials. As shown in the Examples, the conditions used for the monoquat syntheses are comparable as those for the diquat syntheses, and the methods used in this reference are applicable to the present disclosure, substituting the chiral diquat for the monquat OSDA. Additionally, U.S. patent application Ser. No. 14/602,449 filed Jan. 22, 2015, which is incorporated by reference herein for all purposes, but at least for the methods and conditions used to make the STW materials, also described the use of achiral linked diquats for the formation of compositions of STW topologies, and the methods and conditions used there are also relevant and incorporated here.

Additionally, general reactions conditions, including sources of the various oxides useful in the present syntheses, and methods of using the presently disclosed compositions are similar or the same as disclosed in other applications from the California Institute of Technology, for example U.S. patent application Ser. No. 14/517,793, filed Oct. 17, 2014, and Ser. No. 14/602,415 filed Jan. 22, 2015, and Ser. No. 15/063,867 filed Mar. 10, 2015.

The present invention may also be understood more readily by reference to the following description taken in connection with the accompanying Figures, Examples, and Attachments, all of which form a part of this disclosure. It is to be understood that this invention is not limited to the specific products, methods, processes, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this specification, claims, and drawings, it is recognized that the descriptions refer to compositions and processes of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

Typically, the compositions comprise pure silica or are silicate-based, and may be described as comprising:

(a) silicon oxide, germanium oxide, or combination thereof; and optionally (b) aluminum oxide, boron oxide, cerium oxide, gallium oxide, hafnium oxide, iron oxide, tin oxide, titanium oxide, indium oxide, vanadium oxide, zirconium oxide, or combination. In some embodiments, the crystalline microporous solid having chiral morphology is also of STW topology. In certain embodiments the chiral crystalline microporous solid comprises D4R rings in the framework. Generally, the compositions are described in terms of being a crystalline microporous solid. While this encompasses single crystal materials, unless otherwise specified, the compositions comprise bulk polycrystalline enantiomerically enriched microporous powders (crystallites).

More broadly, the chiral crystalline compositions may be described as synthetic molecular sieves that comprise a tetravalent element oxide (i.e. $MO_2$, wherein M refers to a tetravalent element), e.g., silicon(IV) oxide, germanium(IV) oxide, tin(IV) oxide, titanium(IV) oxide, zirconium(IV) oxide, cerium (IV) oxide and/or hafnium(IV) oxide and/or one additional trivalent element oxide, e.g., an oxide of aluminum, boron, iron, indium, or a combination thereof. Within each group of tetravalent and trivalent elements, the relative ratios are flexible. In preferred embodiments, the tetravalent element oxide comprises $SiO_2$ and $GeO_2$. Compositions comprising pure or higher silicate contents are preferred. In some embodiments, the chiral crystalline microporous is a pure silicate, a pure germanate, a pure stannate, a pure titanate, a pure hafnate, an aluminosilicate, a borosilicate, a germanosilicate, or a titanosilicate. In other embodiments, the chiral crystalline microporous is a pure aluminosilicate, a pure borosilicate, a pure germanosilicate, or a pure titanosilicate.

Where described as an aluminosilicate or a pure aluminosilicate, the composition can have a ratio of Si/Al atoms in a range of from 75 to 200. In other embodiments, the ratio of Si/Al atoms in the composition may range from 75 to 80, from 80 to 85, from 85 to 90, from 0 to 95, from 95 to 100, from 100 to 105, from 105 to 110, from 110 to 115, from 115 to 120, from 120 to 125, from 125 to 150, from 150 to 175, or from 175 to 200, or the ratio may be described in terms of two or more of these ranges. The ratio of Si/Al may also be described as about 100. But even higher Si/Al ratios are possible and preferred, for example, where the ratio of Si/Al atoms in a range of from 200 to 250, from 250 to 500, from 500 to 1000, from 1000 to infinity (i.e., pure silicate), or a combination of two or more of these ranges Where described as a germanosilicate or a pure germanosilicate, the composition can have a ratio of Si/Ge atoms in a range of from from 0.5 to 20, In other embodiments, the ratio of Si/Ge atoms in the composition may range from from 0.5 to 1, from 1 to 2, from 2 to 3, from 3 to 4, from 4 to 5, from 5 to 6, from 6 to 7, form 7 to 8, from 8 to 9, from 9 to 10, from 10 to 11, from 11 to 12, from 12 to 13, from 13 to 14, from 14 to 15, from 15 to 16, from 16 to 17, from 17 to 18, from 18 to 19, or from 19 to 20, or the ratio may be described in terms of two or more of these ranges, Again, higher and lower ratios are possible, especially those those compositions higher in silica content, such that the ratio of Si/Ge atoms can also range from 20 to 50, from 50 to 100, from 100 to 150, from 150 to 200, from 200 to 250, from 250 to 500, from 500 to 1000, from 1000 to infinity, or any combination of two or more of these ranges.

In some embodiments, at least some of the pores of the chiral microporous crystalline compositions are occluded with one or more enantiomerically enriched Organic Structure Directing Agents (OSDAs), as described herein. The OSDA may derive, for example, for their inclusion during synthesis. The presence of the enantiomerically enriched OSDA content can be determined, for example, by Circular Dichroism Analysis (as described further in the Examples). Preferably, the chiral OSDAs comprise two substituted imidazolium cations linked by a 2 to 6 atom structurally chiral linker having moieties imparting chirality to the linkage. For example, in certain embodiments, the OSDA comprises a structure having a linked pair of imidazolium cations of a structure:

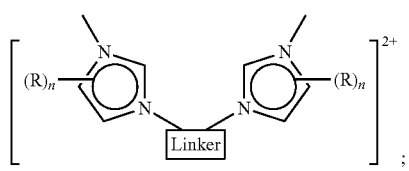

wherein Linker is a 2, 3, 4, 5, or 6-membered chiral linking group, preferably a 4, 5, or 6-membered chiral linking group, including cyclic and alicyclic chiral linking groups, preferably a chiral linking group comprising a saturated cyclic chiral linking group; and R is independently methyl or ethyl, preferably methyl; and n is independently 0, 1, 2, or 3, preferably 2 or 3.

In some embodiments, the moieties chirality to the linker may comprise a chirally substituted ethylene, propylene, butylene, pentylene, hexylene, cyclopropane, aziridine, epoxide, cyclobutane, cyclopentane, cyclohexane, cyclic propyl, butyl, or pentyl ether (e.g., tetrahydrofuranyl), cyclic propyl, butyl, or pentyl amine (e.g., pyrrolidinyl), or cyclic propyl, butyl, or pentyl sulfide (e.g., tetrahydrothiophenyl). The cyclic structure themselve may be linked to impart chirality, or the linkages may further be enantiomerically substituted with, for example, $C_{1-12}$ alkyl substituents (cyclic or alicyclic, linear or branched) or $C_{1-10}$ aryl substituents. For example, the Linker may comprise a structure including:

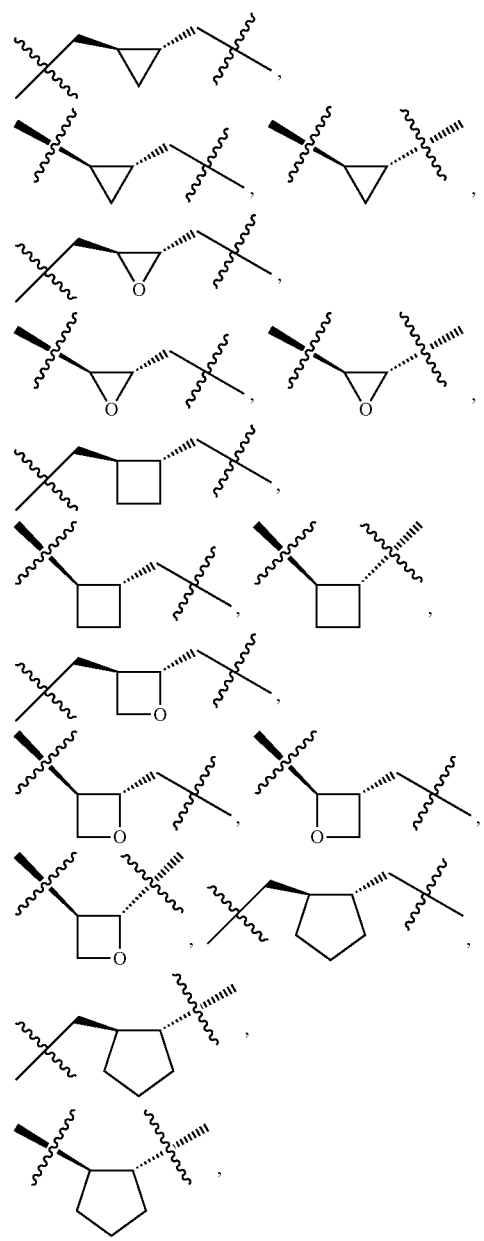

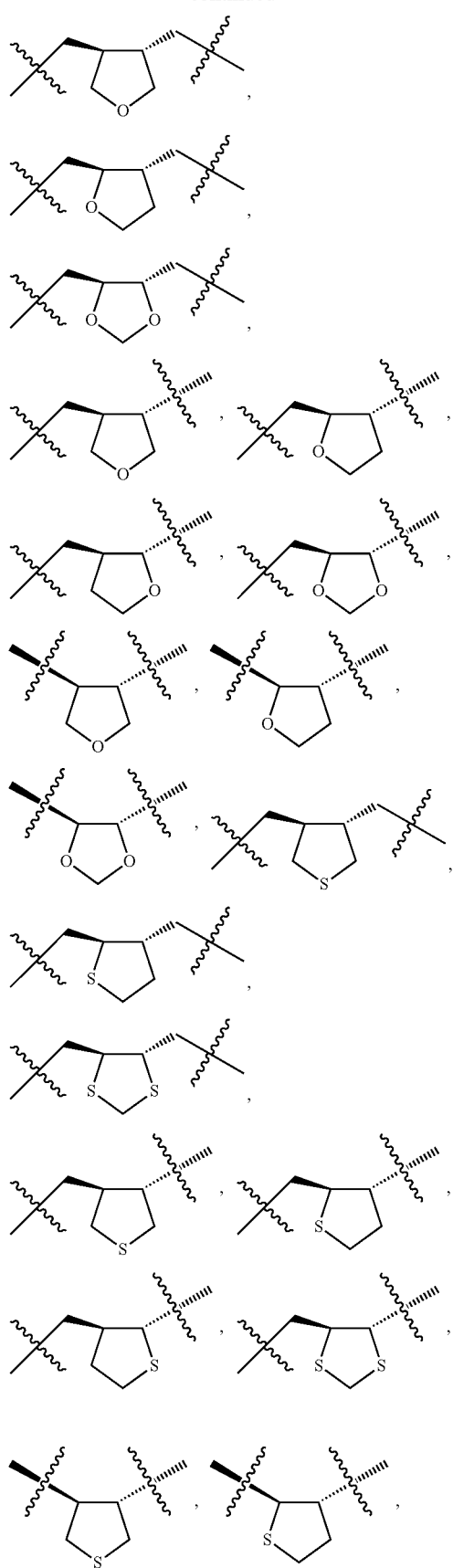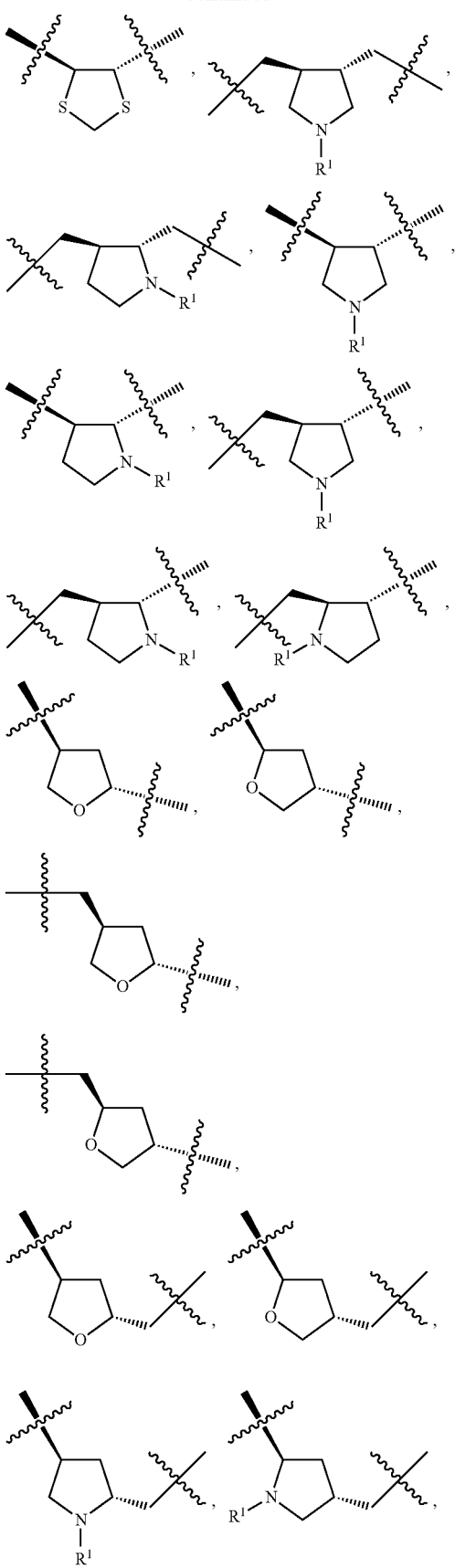

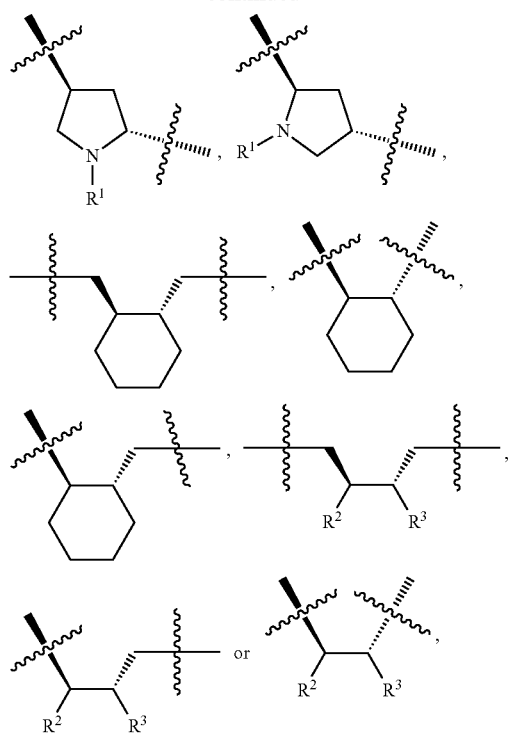
or a chiral enantiomer thereof, where $R^1$ is H or $C_{1-6}$alkyl, $R^2$ and $R^3$ are independently alkyl or aryl, preferably $C_{1-12}$ alkyl or aryl.
Alternatively, the Linker may also comprise a structure:
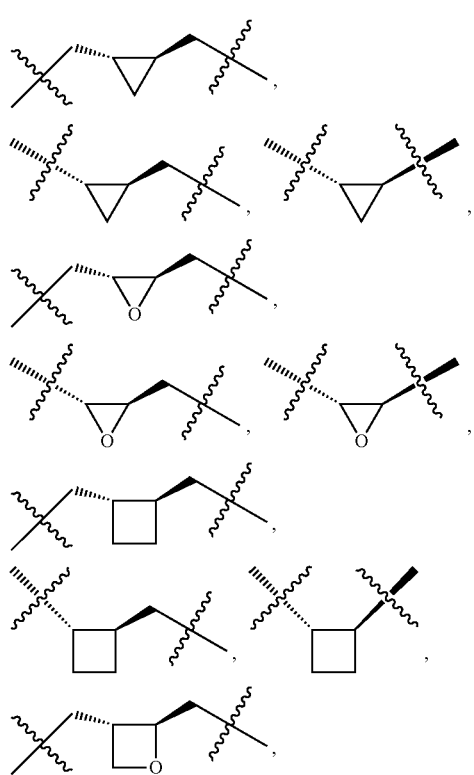
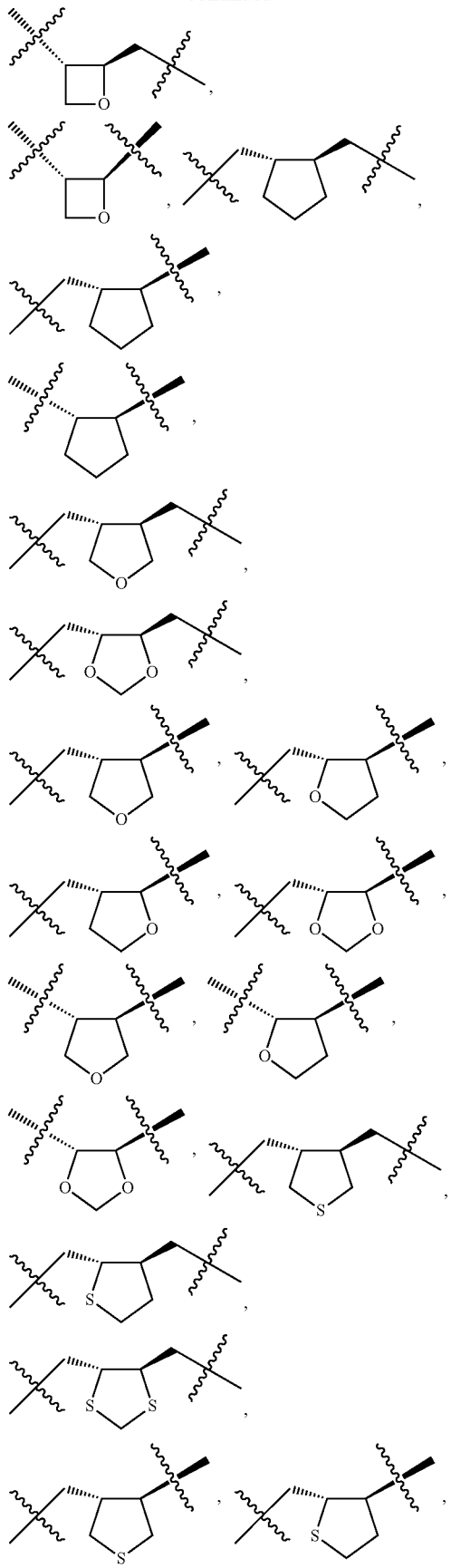

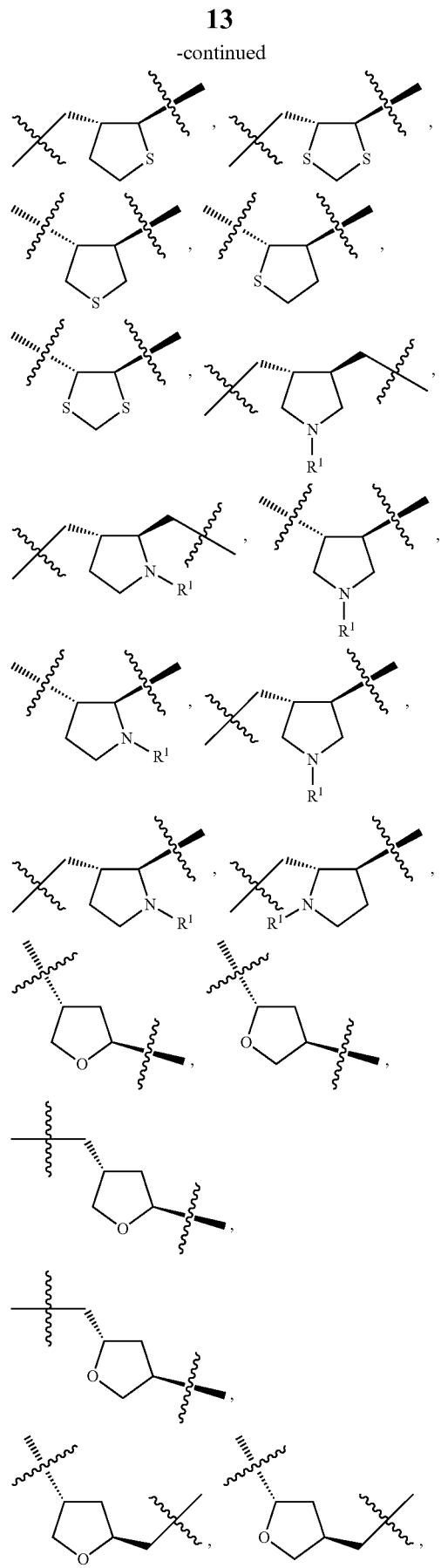

or a chiral enantiomer thereof, where $R^1$ is H or $C_{1-6}$alkyl, $R^2$ and $R^3$ are independently alkyl or aryl, preferably $C_{1-12}$ alkyl or aryl.

Where the OSDA is cationic, the counter anion can be an organic or an inorganic anion. Preferably, the inorganic anion is hydroxide, fluoride, chloride, bromide, iodide, phosphate, sulfate, bisulfate, bisulfite, carbonate, bicarbonate, hexafluorophosphate, nitrate, oxyhalogen, such as chlorate, $ClO_3^-$ and perchlorate, $ClO_4^-$, and the organic anion is a $C_{1-4}$ aliphatic carboxylate, a $C_{1-4}$ aliphatic sulfate, a $C_{1-4}$ aliphatic sulfonate, a $C_{1-4}$ alkoxide and a $C_{7-11}$ aryl carboxylate, a $C_{6-10}$ aryl sulfate, a $C_{6-10}$ aryl sulfonate, a $C_{6-10}$ aryloxide. The organic anion can also be preferably be a $C_{1-4}$ cyclic, linear, branched, unbranched, saturated or unsaturated aliphatic group, or a $C_{6-10}$ substituted or non-substituted, aromatic, including heteroaromatic groups.

In some embodiments, a counter anion of the organic structure directing agents can be obtained by any one of the processes known to a person of skill in the art. For example in embodiments where the cationic OSDA has a iodide anion, such counter ion can be replaced with a hydroxide ion by ion exchange using an ion exchange resin.

In those embodiments where the chiral crystalline microporous solid is substantially free of the OSDA, the solid may be in predominantly in a hydrogen form. In other embodiments, the chiral crystalline microporous solid is calcined and is either in its hydrogen form or contains at least one alkali metal cation, alkaline earth metal dication, or transition metal, transition metal salt, or transition metal oxide within its pores. For example, in some embodiments, the chiral crystalline microporous solid contains one or more Li, Na, K, Rb, Cs, Be, Mg, Ca, Sr, Be, Al, Ga, In, Zn, Ag, Cu, Fe, Co, Ni, Cd, Ru, Rh, Pd, Pt, Au, Hg, La, Ce, Pr, Nd, Pm, Sm, Eu, or $R_{4-n}N^+H_n$ cations, in its pores, where R is alkyl, n=0-4. In other embodiments, the chiral crystalline microporous solid contains, in its pores, scandium, yttrium, tin, titanium, zirconium, vanadium, manganese, chromium, molybdenum, tungsten, iron, ruthenium, osmium, cobalt, rhodium, iridium, nickel, palladium, platinum, copper, silver, gold, or mixtures thereof, each as a metal, oxide, or salt. In one aspect, the pores contain copper, as metal, oxide, or salt.

In addition to the inventive compositions, the present disclosure describes methods and processes for preparing enantiomerically enriched silicate compositions. Some embodiments provide processes comprising hydrothermally treating a composition comprising:

(a) at least one source of a silicon oxide, germanium oxide, or combination thereof;

(b) optionally at least one source of aluminum oxide, boron oxide, cerium oxide, gallium oxide, hafnium oxide, iron oxide, tin oxide, titanium oxide, vanadium oxide, zinc oxide, zirconium oxide, or combination or mixture thereof;

(c) either a source of fluoride or a source of hydroxide; and (d) an enantiomerically enriched chiral Organic Structure Directing Agent (OSDA) under conditions effective to crystallize an enantiomerically enriched crystalline microporous silicate that exhibits a chiral morphology and has enantiomeric excess ("ee") of at least 5%, 10%, 15%, 20%, 25%, 50%, 75%, or 90%.

As described above for the compositions, the enantiomerically enriched chiral Organic Structure Directing Agents (OSDAs), preferably comprise two substituted imidazolium cations linked by 2 to 6 atom linker having moieties imparting chirality to the linkage. For example, in certain embodiments, the OSDA comprises a structure having a linked pair of imidazolium cations of a structure:

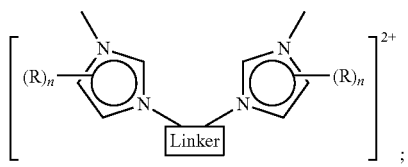

wherein Linker is a 2, 3, 4, 5, or 6-membered chiral linking group, preferably a 4, 5, or 6-membered chiral linking group, including cyclic and alicyclic chiral linking groups, preferably a chiral linking group comprising a saturated cyclic chiral linking group; and R is independently methyl or ethyl, preferably methyl; and n is independently 0, 1, 2, or 3, preferably 2 or 3, In certain embodiments, the Linker is defined by the structures as described elsewhere herein.

In certain embodiments, the as-synthesized enantiomerically enriched crystalline microporous silicate has an STW framework.

In some embodiments, the reaction mixture is a gel form, preferably a homogeneous gel form, formed with or without heating the reaction mixture at a temperature range of between about 20-100° C., with or without stirring or agitation thereof. In some embodiments wherein the preparing comprising heating the reaction mixture the heating can be performed for a time of from about 10 minutes to about 14 days. Preferably, preparing a reaction mixture to form a homogeneous gel can be performed at room temperature or at about 20° C., and in less than 8 hours with or without agitation.

In some embodiments, the pH of the reaction mixture depends on the choice of the anion for the OSDA. For example, where the anion is hydroxide the pH is higher than 7; for example, in exemplary embodiments when hydroxide is the counter anion, a resulting mixture has a pH of about 12.5 to 14. In other cases, the pH can be substantially neutral. For example, in exemplary embodiments, when fluoride is the counter ion and hydrogen fluoride is used to neutralize the hydroxide, a resulting mixture has a pH of about 7.

In embodiments of the method herein described, the reaction mixture can also comprise one or more oxides of a tetravalent element from Group 4 or 14. In some embodiments, this one or more element may include silicon, germanium, titanium, tin, zirconium, cerium, or hafnium. Silicon is preferred. Sources of such element oxides may include alkoxides, oxides, hydrated oxides, hydroxides, carboxylates (e.g., acetates), oxalates, ammonium salts and sulfates of the element(s).

Sources of silicon comprise amorphous silica, fumed silica, precipitated silicates, silica hydrogel, silicic acid, colloidal silica, tetra-alkyl orthosilicates (e.g. tetraethyl orthosilicate), and hydrated silica (including hydroxides). Examples of silica sources useful for making high-silica forms of the molecular sieves of the disclosure include fumed silica (e.g. CAB-O-SIL M-5, Cabot Corporation), hydrated silica (e.g. HI-SIL 233, PPG Industries), silica tetra alkoxides, and mixtures thereof. In some embodiments source of silica can be provided by colloidal forms of silica where the solid content is, for example, 30-40 wt. % $SiO_2$, and these materials can be stabilized by small amounts of sodium or ammonium cations.

In some embodiments, the reaction mixtures comprises silica and germania, or sources thereof. In independent embodiments, the ratio of Si/Ge of the reaction mixture can be between 1:1 and 20:1, preferably between 2:1 and 5:1, and most preferably about 2:1 to 3:2. Other ratios are described elsewhere herein. In some embodiments, of Si/Ge ratio, where Si/Ge becomes infinite, the reaction mixture can be considered a pure silica mixture. In some of those embodiments, Si/Ge molecular sieves with STW framework herein described have a hydrothermal stability that increases with an increasing silicon content. Sources of germanium include germanium oxide, germanium alkoxides, for example germanium ethoxide, germanium hydroxides, and/or germanium carboxylates.

The sources of the oxides can be added to the reaction mixture from more than one source. In addition to the compositions described elsewhere herein, the compositions may comprise stannosilicates, cerium silicates, hafnium silicates, zirconium silicates, including pure stannosilicates, pure cerium silicates, pure hafnium silicates, and zirconium silicates. In some embodiments, the processes can include sources of three or more sources of oxides, for example germanostannosilicates, germanoaluminosilicates, or germanotitanosilicates, and including molecular sieves from oxides of four or five elements. Accordingly, in those embodiments preparing the reaction mixture comprises at least one source of each of the elemental oxides.

The sources of the oxides may also comprise sources of one or more oxides of a trivalent element. The trivalent element can include those elements from Groups 3-13 of the Periodic Table. More specifically, the trivalent element can be a metal with the +3 oxidation state, such as of gallium, aluminum, iron, cobalt, rhodium, lanthanum, praseodymium, gadolinium, boron, titanium, vanadium, and chromium. The trivalent element in the +3 oxidation state can also be indium, thallium, scandium, or yttrium. Oxides of trivalent elements can be introduced into the reaction mixture in the form of alkoxides, carboxylates (e.g., acetates), hydroxides, hydrated oxides, oxalates, ammonium salts and sulfates of the trivalent elements. Typical sources of aluminum oxide include aluminates, alumina, and aluminum compounds such as $Al(isopropoxide)_3$, $AlCl_3$, $Al(NO_3)_3$, $Al_2(SO_4)_3$, $Al(OH)_3$, kaolin clays, and other zeolites. An example of the source of aluminum oxide is LZ-210 zeolite (a type of Y zeolite). Boron, gallium, and iron can be added in forms corresponding to their aluminum and silicon counterparts. In some embodiments, the trivalent elements are provided from the reaction mixture from more than one source.

In such cases, certain embodiments provide that the molar ratio of the tetravalent element to trivalent element is 100:1 and greater. For example, in the case of an aluminosilicate having an Si/Al ratio of 100 and greater or a titanosilicate material having a ratio of Si/Ti of 100 or greater.

In some embodiments, the ratio of the tetravalent element to the OSDA is in a range of from 1:2 to 100:1. Preferred embodiments again here provide that the tetravalent element is Si. In related embodiments, the molar ratio of the tetravalent element (e.g., Si)/OSDA is defined as encompassing a range of from 1:2 to 1:1, from 1:1 to 2:1, from 2:1 to 3:1, from 3:1 to 4:1, from 4:1 to 5:1, from 5:1 to 7.5:1, from 7.5:1 to 10:1, from 10:1 to 15:1, from 15:1 to 20:1, from 20:1 to 25:1, from 25:1 to 30:1, from 30:1 to 35:1, from 35:1 to 40:1, from 40:1 to 45:1, from 45:1 to 50:1, or a combination of two or more of these ranges. For example, in some embodiments, the molar ratio of Si:OSDA is in a range of from about 4:1 to 1:2, preferably from about 3:1 to 1:1, even more preferably about 2:1.

In other embodiments, the ratio of water to the tetravalent element is in a range of from 30:1 to 1:1. Preferred embodiments again here provide that the tetravalent element is Si. In related embodiments, then, the molar ratio of water to the tetravalent element (e.g., Si) is defined as from 30:1 to 25:1, from 25:1 to 20:1, from 20:1 to 15:1, from 15:1 to 10:1, from 10:1 to 9:1, from 9:1 to 8:1, from 8:1 to 7:1, from 7:1 to 6:1, from 6:1 to 5:1, from 5:1 to 4:1, from 4:1 to 3:1, from 3:1 to 2:1, from 2:1 to 1:1, or a combination of two or more of these ranges.

In particular in embodiments, the ratio of metal oxides, especially silica to water is specifically controlled to a predetermined $H_2O/Si$ molar ratio. In some embodiments, the molar ratio of water to $SiO_2$ in the reaction mixture is any of the ratios provided above for the ratio of water to tetravalent element, and includes 20 or less, preferably in a range of from 2 to 14, most preferably between 4 to 7.

In other embodiments, where fluoride is present as the mineralizing agent, the ratio of fluoride ion to the tetravalent element to water is in a range of from 20:1 to 1:1. Preferred embodiments again here provide that the tetravalent element is Si. In related embodiments, then, the molar ratio of fluoride ion to the tetravalent element (e.g., Si) is defined as from 20:1 to 15:1, from 15:1 to 10:1, from 10:1 to 9:1, from 9:1 to 8:1, from 8:1 to 7:1, from 7:1 to 6:1, from 6:1 to 5:1, from 5:1 to 4:1, from 4:1 to 3:1, from 3:1 to 2:1, from 2:1 to 1:1, or a combination of two or more of these ranges According to some embodiments, the reaction mixture can also include anions such as hydroxide, fluoride, chloride, bromide, iodide, acetate, sulfate, tetrafluoroborate and carboxylate. An exemplary anion for the reaction mixture is fluoride, which can be available as an aqueous salt or in the form of hydrogen fluoride (HF). An additional exemplary anion for the reaction mixture is hydroxide that in some embodiments can be added to the reaction mixture in form of an alkyl ammonium hydroxide, for example tetramethyl ammonium hydroxide (TMAOH). In one embodiment, the reaction mixture contains hydroxide and fluoride ions in ratios between $1OH^-$:$4F^-$ to $4OH^-$:$1F^-$, such as between $3OH^-$:$4F^-$ to $4OH^-$:$3F^-$, and preferably around $1OH^-$:$1F^-$. In one preferred embodiment, OSDA hydroxide is neutralized with an equal molar amount of hydrogen fluoride such that the hydroxide is substantially replaced with fluoride ion as the counter anion in the solution. The term "substantially replaced" as used herein with reference to ion replacement refers to embodiments in which at least 99% of a first anion is replaced by a second anion and includes hydroxide neutralized by hydrogen fluoride.

In some embodiments, the reaction mixture is sealed in a container and/or stirred for a time period sufficient to substantially complete the formation of the enantiomerically enriched microporous crystalline composition, preferably for at least 12 hours, and more preferably for around 12-14 hours. The term "substantially complete" with reference to a reaction indicate a time sufficient to have a detectable product of the reaction in the reaction mixture.

In other embodiments, the hydrothermal treating can be accompanied by the evaporation of water and/or other volatile byproducts, such as ethanol, isopropanol, and other alcohols deriving from alkoxide precursors, e.g. the process may further comprise using a stream of air, possibly in an evaporation step. Some water can be retained after the evaporating. In some embodiments, reaction mixture comprises added fluoride, e.g. in the form of aqueous hydrogen fluoride (or hydrofluoric acid), sodium fluoride, ammonium fluoride, or other fluoride salts.

In some embodiments the preparing can comprise keeping and/or stirring the reaction mixture at a temperature between about 20° C. and about 100° C. for a time range from about 10 min to about 2 weeks to form a homogeneous gel mixture, in a gelling step. Preferably, the reaction mixture is kept and/or stirred at a temperature about 20° C.

In some embodiments, the reaction mixture is maintained under crystallization conditions sufficient to form the molecular sieve. Such conditions are generally known. (See, Harry Robson, Verified Syntheses of Zeolitic Materials, $2^{nd}$ revised edition, Elsevier, Amsterdam (2001)). For example, the reaction mixture can be maintained at an elevated temperature until the molecular sieve is formed over a period of a few days to several weeks. The hydrothermal crystallization is usually conducted under autogenous pressure, ranging from 50-200 PSI (0.34 MPa to 1.38 MPa), and usually in a PTFE-lined autoclave so that the reaction mixture is subject to autogenous pressure.

In some embodiments, the hydrothermally treating is done at a temperature in a range of from about 100° C. to about 200° C. for a time effective for crystallizing the enantiomerically enriched chiral crystalline microporous solid. In certain other embodiments, the hydrothermally treating is done at a temperature in a range of from about 100° C. to about 120° C., from about 120° C. to about 140° C., from about 140° C. to about 160° C., from about 160° C. to about 180° C., from about 180° C. to about 200° C., or any combination of two or more of these ranges. Independent embodiments also provide that the hydrothermal treating is done by holding at one or more of about 100° C., 110° C., 120° C., 130° C., 140° C., 150° C., 160° C., 170° C., 180° C., 190° C., or about 200° C., or any of the temperatures otherwise described on the Examples.

The reaction mixture can be maintained for a time and under conditions at these temperature for a time from about 1 to about 70 days, preferably from about 3 to about 23 days and in particular, from about 5 to about 7 days.

In some embodiments, the reaction mixture can include seed crystal, possibly seed crystals having STW framework. In some embodiments, seed crystals are added in order to accelerate the formation of the molecular sieves. For example, seed crystals can be at or around 0.01 micron to 10 micron in diameter, and preferably at or around 0.05 micron to 2 micron in diameter to accelerate the formation of the molecular sieve. Smaller seed crystals can result in faster molecular sieve formation. In some embodiments, seed crystals can be introduced in the reaction mixture in form of free crystals in suspension. In some embodiments, seed crystals can be introduced in the reaction mixture incorporated onto solid supports (e.g. membranes). When used as seeds, seed crystals are added in an amount between 0.01% and 10% of the mass of the total amount of oxide in the reaction mixture. The total amount of oxide refers to the total mass of oxides in the reaction mixture gel prior to heating, including but not limited to silica, alumina, germanium(IV) oxide, and other metal oxides.

In some embodiments, once the enantiomerically enriched crystalline microporous solid has formed, the it is isolated/separated from the reaction mixture by standard mechanical separation techniques such as filtration. The crystals are water-washed and then dried to obtain the as-synthesized molecular sieve crystals. The drying can be performed at atmospheric pressure or under vacuum, and possibly at an elevated temperature, most preferably around 100° C.

In embodiments where the enantiomerically enriched crystalline microporous solid formed is an intermediate material, the process of the present disclosure can further include synthesizing a target molecular sieve by post-synthesis techniques (e.g., once the OSDA is removed), such as acid leaching. Usually, it is desirable to remove the alkali metal cation by ion exchange and replace it with hydrogen, ammonium, or any desired metal ion. The enantiomerically enriched crystalline microporous solid can be leached with chelating agents, e.g., EDTA or dilute acid solutions, to increase the silica to alumina mole ratio. The molecular sieve can also be steamed; steaming helps stabilize the crystalline lattice to attack from acids.

In several embodiments the enantiomerically enriched crystalline microporous solid obtained with methods herein described can be used as-synthesized, or can be thermally treated (calcined). The term "as-synthesized" refers to the enantiomerically enriched crystalline microporous solid in its form after crystallization, prior to removal of the structure directing agent.

The structure directing agent can be removed by thermal treatment (e.g., calcination), preferably in an oxidative atmosphere (e.g., air, gas with an oxygen partial pressure of greater than 0 kPa) at a temperature readily determinable by one skilled in the art sufficient to remove the structure directing agent from the molecular sieve. In some embodiments, the molecular sieve obtained with methods herein described can be calcined in steam, air or inert gas at temperatures ranging from about 200° C. to about 800° C. for periods of time ranging from 1 to 48 hours, or more. In some embodiments, the isolated crystalline microporous solid is calcined at a temperature in a range of from about 200° C. to 300° C., from 300° C. to 350° C., from 350° C. to 400° C., from 400° C. to 450° C., from 450° C. to 500° C., from 500° C. to 550° C., from 550° C. to 600° C., from 600° C. to 650° C., from 650° C. to 700° C., from 700° C. to 750° C., from 750° C. to 800° C., from 800° C. to about 850° C., or higher, or at a temperature from two or more of these ranges.

The OSDAs can also be removed using oxidation processes, such as the oxidization of organic compounds using ozone. Ozone can also be used to remove OSDAs at either room temperature or elevated temperatures, such as between about 75° C. and about 250° C., preferably at temperatures between about 125° C. and about 175° C., such as at 150° C., which can prevent severe degradation of the molecular sieve framework. Usually, it is also desirable to remove the extra-framework cations (e.g. $Na^+$) by ion-exchange or other known method and replace it with ammonium, or any desired metal-ion.

Molecular sieves synthesized by the processes of the present disclosure can be characterized by their XRD pattern. Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation and from variations in the Si/Al or other mole ratios from sample to sample. Calcination can also cause minor shifts in the XRD pattern. Notwithstanding these minor perturbations, the basic crystal lattice structure remains unchanged.

The powder X-ray diffraction patterns presented herein were collected by standard techniques. The radiation was CuK-a radiation. The peak heights and the positions, as a function of 2θ, where θ is the Bragg angle, were read from the relative intensities of the peaks (adjusting for background), and d, the interplanar spacing in Angstroms corresponding to the recorded lines, can be calculated.

In some embodiments, the molecular sieve catalyst of the present disclosure can optionally be combined with one or more catalyst supports, active base metals, other molecular sieves, promoters, and mixtures thereof. Examples of such materials and the manner in which they can be used are disclosed in U.S. Pat. No. 4,910,006, issued May 20, 1990 and U.S. Pat. No. 5,316,753, issued May 31, 1994, each of which is incorporated by reference herein for at least these teachings.

In other embodiments, the calcined crystalline microporous solid are treated with at least one transition metal or transition metal oxide. In several embodiments, metals are introduced into molecular sieves herein described by replacing some of the cations in the molecular sieve with metal cations via standard ion exchange techniques known in the art. Typical replacing cations can include metal cations, e.g., rare earth, Group IA, Group IIA and Group VIII metals, as well as their mixtures. Examples of the replacing metallic cations include cations of metals such as rare earth, manganese, calcium, magnesium, zinc, cadmium, platinum, palladium, nickel, cobalt, titanium, aluminum, tin and iron. Transition metals and metal oxides may also be introduced, for example, by vapor deposition methods.

In specific embodiments, the pores of the chiral crystalline microporous solid contain Li, Na, K, Rb, Cs, Be, Mg, Ca, Sr, Be, Al, Ga, In, Zn, Ag, Cu, Fe, Co, Ni, Cd, Ru, Rh, Pd, Pt, Au, Hg, La, Ce, Pr, Nd, Pm, Sm, Eu, or $R_{4-n}N^+H_n$ cations, where R is alkyl, n=0-4. In specific aspects, the pores contain NaCl or KCl.

In other specific embodiments, the pores of the chiral crystalline microporous solid contain scandium, yttrium, tin, titanium, zirconium, vanadium, manganese, chromium, molybdenum, tungsten, iron, ruthenium, osmium, cobalt, rhodium, iridium, nickel, palladium, platinum, copper, silver, gold, or mixtures thereof, each as a metal, oxide, or salt. In one aspect, the pores contain copper, as metal, oxide, or salt.

In still other embodiments, the hydrogen, ammonium, and metal components can be ion-exchanged into the molecular sieves of the disclosure. The molecular sieves of the disclosure can also be impregnated with the metals, or the metals can be physically and intimately admixed with the molecular sieves of the disclosure using standard methods known to the art. Typical ion-exchange techniques involve contacting the synthetic molecular sieve with a solution containing a salt of the desired replacing cation or cations. Although a wide variety of salts can be employed, chlorides and other halides, acetates, nitrates, and sulfates are particularly preferred. The molecular sieve is usually calcined prior to the ion-exchange procedure to remove the organic matter present in the channels and on the surface, since this approach results in a more effective ion exchange. Representative ion exchange techniques are known in the art. In some embodiments, following contact with the salt solution of the desired replacing cation, the molecular sieve is typically washed with water and dried at temperatures ranging from about 65° C. to about 200° C. After washing, the molecular sieve can be calcined in air or inert gas as described above, to produce a catalytically active product especially useful in hydrocarbon conversion processes. Regardless of the cations present in the as-synthesized form of the molecular sieves of the disclosure, the spatial arrangement of the atoms which form the basic crystal lattice of the molecular sieve remains essentially unchanged.

In some embodiments, the transition metals may be deposited within the pores of the molecular sieves by processes such as chemical or physical vapor deposition.

The molecular sieves made with the methods of the present disclosure can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the molecular sieve can be extruded before drying, or, dried or partially dried and then extruded.

The molecular sieves made with the methods of the present disclosure can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al, and U.S. Pat. No. 5,316,753, issued May 31, 1994 to Nakagawa, both of which are incorporated by reference herein in their entirety.

The disclosure also contemplates the use of these inventive materials as enantioselective adsorbants and catalysts.

For example, in certain embodiments, the enantiomerically enriched chiral a crystalline microporous solid can be used in methods of selectively adsorbing chiral organic molecules, the methods comprising contacting a stereoisomeric or enantiomeric mixture of the organic molecule with the enantiomerically enriched crystalline microporous solid described herein. Examples of such selective adsorbances or separations are described in the Examples.

Likewise, the present microporous crystalline compositions may be used in traditional applications where the corresponding non-enantiomerically enriched molecular sieves may be used, for example acetylation addition, alkylation, dealkylation, hydrodealkylation, reductive alkylation, amination, ammonia synthesis, aromatization, arylation, autothermal reforming, carbonylation, decarbonylation, reductive carbonylation, carboxylation, reductive carboxylation, reductive coupling, condensation, cracking, hydrocracking, cyclization, cyclooligomerization, ammoxidation, dehalogenation, dimerization, epoxidation, esterification, halogenation, hydrohalogenation, homologation, hydration, dehydration, hydrogenation, dehydrogenation, hydrocarboxylation, hydroformylation, hydrogenolysis, hydrometallation, hydrosilation, hydrolysis, hydrotreating, isomerization, methylation, demethylation, metathesis, methanol synthesis, oxidation, partial oxidation, polymerization, reduction, reformation, reverse water gas shift, sulfonation, telomerization, transesterification, trimerization, Sabatier reaction, carbon dioxide reforming, preferential oxidation, or preferential methanation. But additionally, these enantiomerically enriched materials may be used in methods of preparing enantiomerically-enriched chiral organic molecule product from achiral or prochiral precursors, wherein the method comprises conducting an appropriate chemical reaction to form the chiral organic molecule product in the presence of the enantiomerically enriched crystalline microporous solid described herein.

For example, in some embodiments, the reaction is an epoxidation reaction or an epoxide ring-opening reaction. An example of the latter reaction is shown in the Examples. The use of molecular sieves of comparable chemistries and pore sizes (e.g., ITQ-16, ITQ-30, SSZ-33, TS-1) is also known for epoxidation reactions, lending support for the use of the presently described enantiomerically enriched molecular sieves for this purpose to produce enantiomerically enriched products. See, e.g., U.S. Pat. Nos. 5,869,706, 6,239,315, 8,115,001, which are incorporated by reference in their entireties for all purposes, but at least for their descriptions of substrates and reaction conditions for the catalytzed chemical transformations described herein. In certain related embodiments, the chemical reaction can also comprise a chiral olefin oxidation, for example proceeding through an epoxide, for example, the preparation of glycol monoethers from olefins, which comprises reacting the olefins with an epoxidizing reagent (e.g., aqueous hydrogen peroxide, organic peroxides such as tert-butylhydroperoxide and cumene hydroperoxide, or a hydrogen/oxygen mixture) in the simultaneous presence of hydroxyl-containing organic compounds over a mixture of the presently described molecular sieves and solid alkoxylation catalysts. See, e.g., U.S. Pat. No. 6,239,315.

In other embodiments, the reaction is an asymmetric hydrogenation reaction, and achiral or prochiral ethylenically unsaturated compound, imine, ketone, enamine, enamide and vinyl ester is hydrogenated with molecular hydrogen in the presence of metal catalysts comprising an enantiomerically enriched chiral molecular sieve of the present disclosure having pores containing a hydrogenation catalyst, e.g., a platinum group or coinage metal such as Pt, Pd, Ni, Rh, Ir, Ru, Os, Cu, Ag, or Au or a salt or oxide thereof.

Likewise, the catalysts comprising the presently described enantiomeric enriched materials, addivated by suitable metal catalysts known to those skilled in the art can be used to catalyze other reactions, including dihydroxylation, oxyamination, hydride transfer, hydrosilylation, hydroboration, hydrovinylation, hydroformylation, hydrocarboxylation, isomerization, allylic alkylation, cyclopropanation, Diels-Alder reaction, Heck reaction, isomerization, Aldol reaction, Michael addition and epoxidation. Again, such reactions are known to be catalyzed by other, non-chiral or enantiomerically enriched molecular sieves of similar pore sizes, for example having Beta, TS-1, ITQ-16, ITQ-30, ZSM-5, ZSM-11, ZSM-12, ZSM-23, ZSM-35, ZSM-38, ZSM-48 and ZSM-50 topologies. Note that the presently described molecular sieves may be used to effect these asymmetric transformations with or without the use of added chiral directing agents (e.g., without optically active amines or added chiral transition metal catalysts). See also U.S. Pat. Nos. 4,554,262; 5,414,078.

Terms

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of" and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method or process steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of" For those embodiments provided in terms of "consisting essentially of," the basic and novel characteristic(s) of a process is the ability to provide a microporous material having the designated topologies, and of a product or intermediate, one having the designated topology.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Throughout this specification, words are to be afforded their normal meaning, as would be understood by those skilled in the relevant art. However, so as to avoid misunderstanding, the meanings of certain terms will be specifically defined or clarified.

As used herein, the term "chiral" refers to a material that is asymmetric in such a way that the structure and its mirror image are not superimposable (by contrast, a mirror image of an achiral object, such as a sphere, cannot be distinguished from the object). Chiral compounds are typically optically active. And while chirality is normally associated with organic and organometallic structures, the present disclosure describes chiral microporous inorganic structures, which may or may not have chiral organic OSDAs occluded in the pores of the inorganic lattice. A chiral object and its mirror image are called enantiomorphs (Greek, "opposite forms"). As used herein, the term chiral microporous composition also connotes the presence of enantiomeric enrichment as described elsewhere herein.

While the term "enantiomer" is generally used when discussing organic or organometallic compounds and "enantiomorph" is used more generally, in the present disclosure, either term may be used to describe the microporous silicate compositions.

As used herein, the term "enantiomeric excess"(or "ee") is a measurement of purity used for chiral substances. It reflects the degree to which a sample contains one enantiomer (or enantiomorph) in greater amounts than the other. A racemic mixture has an ee of 0%, while a single completely pure enantiomer or enantiomorph has an ee of 100%. A sample with 75% of one enantiomer and 25% of the other has an ee of 50% (75%-25%). There are several means for determining the enantiomeric excess of a given sample of molecular sieve, including circular dichroism spectra (where the sieve contains the chiral OSDA) or HTREM, as disclosed herein. Mueller matrix microscopy has also been described as a promising method for assessing the enantiomeric purity of a microcrystalline powder. Additionally, the enantiomeric excess of the enantiomerically enriched microcrystalline solids may also be defined functionally; i.e., in terms of the products resulting from their use. For example, given the relative ease of measuring the optical purity of organic molecules, the enantiomeric excess of a given sample of molecular sieve may be equated to the enantiomeric excess of the product resulting from the reaction of a prochiral substrate (e.g., an olefin in the context of hydrogenation or epoxidation) to form an enantiomerically enriched product, or the relative adsorption of one enantiomer from a racemic mixture. Given that non-enantiomerically enriched molecular sieves provide no discrimination in this regard, the presence of any enantiomeric enrichment above experimental error (e.g., enantiomeric enrichment greater than about 5%) is evidence of the degree of enantiomeric enrichment of the molecular sieve.

The terms "halo" and "halogen" are used in the conventional sense to refer to a chloro, bromo, fluoro, or iodo substituent.

"Lower alcohols" or lower alkanes refer to alcohols or alkanes, respectively, having 1-10 carbons, linear or branched, preferably 1-6 carbon atoms and preferably linear. Methanol, ethanol, propanol, butanol, pentanol, and hexanol are examples of lower alcohols. Methane, ethane, propane, butane, pentane, and hexane are examples of lower alkanes.

Unless otherwise indicated, the term "isolated" means physically separated from the other components so as to be free of solvents or other impurities; additional embodiments include those where the compound is substantially the only solute in a solvent or solvent fraction, such a analytically separated in a liquid or gas chromatography phase.

"Optional" or "optionally" means that the subsequently described circumstance may or may not occur, so that the description includes embodiments where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present. Similarly, the phrase "optionally isolated" means that the target material may or may not be separated from other materials used or generated in the method, and, thus, the description includes separate embodiments where the target molecule or other material is separated and where the target material is not separated, such that subsequence steps are conducted on isolated or in situ generated product.

The terms "separating" or "separated" carries their ordinary meaning as would be understood by the skilled artisan, insofar as it connotes separating or isolating the product material from other starting materials or co-products or side-products (impurities) associated with the reaction conditions yielding the material. As such, it infers that the skilled artisan at least recognizes the existence of the product and takes specific action to separate or isolate it. Absolute purity is not required, though preferred, as the material may contain minor amounts of impurities and the separated or isolated material may contain residual solvent or be dissolved within a solvent used in the reaction or subsequent purification of the material.

As used herein, the term "crystalline microporous solids" or "crystalline microporous silicate or aluminosilicate solids," sometimes referred to as "molecular sieves," are crystalline structures having very regular pore structures of molecular dimensions, i.e., under 2 nm. The term "molecular sieve" refers to the ability of the material to selectively sort molecules based primarily on a size exclusion process. The maximum size of the species that can enter the pores of a crystalline microporous solid is controlled by the dimensions of the channels. These are conventionally defined by the ring size of the aperture, where, for example, the term "8-MR" or "8-membered ring" refers to a closed loop that is typically built from eight tetrahedrally coordinated silicon (or aluminum) atoms and 8 oxygen atoms. The term "molecular sieve" further indicates a porous solid having interconnected pores of same or different sizes, and includes (a) intermediate and (b) final or target molecular sieves and molecular sieves produced by (1) direct synthesis or (2) post-crystallization treatment (secondary synthesis). Exemplary molecular sieves comprise crystalline, microporous materials (e.g. pores less than 2 nm) that comprise three-dimensional networks of oxide tetrahedra. Typically, molecular sieves present a specificity in the structure-property relationships that can be used to select an appropriate molecular sieves for one or more specific applications. At present, over 200 different frameworks have been identified. As an example of the utility within these possible frameworks, recent studies on carbon capture have identified numerous frameworks with calculated performance superior to known materials. The term "silicate" refers to any composition including silica. It is a general term encompassing, for example, pure-silica, aluminosilicate, borosilicate, or titanosilicate structures. The terms "aluminosilicate," "borosilicate," "germanosilicate," and "titanosilicate," refers to any composition comprising silicate and and oxide of aluminum, boron, germanium, and titanium, respectively. These compositions may contain only the named oxides, in which case, they are described as a "pure aluminosilicate," "pure borosilicate," "pure germanosilicate," or "pure titanosilicate," or each may contain other oxides as well. The term "zeolite" refers to an aluminosilicate composition that is a member of this family.

Germanosilicate molecular sieves are microporous material frameworks comprised of $Si^4$ along with $Ge^{4+}$ oxides. These materials have neutral frameworks. A germanosilicate STW molecular sieve has an open framework structure sharing the oxygen atoms of $[SiO_4]$ and $[GeO_4]$ tetrahedral. In one embodiment, the syntheses are conducted in the presence of fluoride. The aqueous organic quaternary ammonium hydroxide is combined with a source of silica, e.g., tetraethylorthosilicate, along with a source of germanium, e.g. germanium(IV) ethoxide or germanium(IV) oxide. The resulting mixture is allowed to stir until complete hydrolysis of the alkoxides is accomplished. Excess water and alcohol are then allowed to evaporate, hydrofluoric acid is typically added, and the mixture is allowed to react under hydrothermal conditions until a crystalline product forms.

As used herein, the STW framework refers to the three letter code of molecular sieves consistent with the structural classification given by the Structure Commission of the International Zeolite Association. As indicated in the information provided by the Structure Commission of the International Zeolite Association incorporated herein by reference in its entirety STW framework includes ring sizes of 4, 5, 8 and 10 tetrahedral atoms. A pure silica STW framework has a powder X-Ray Diffraction (PXRD) pattern consistent with that provided in Table 1:

TABLE 1

Representative PXRD Peaks for STW Topology; peak heights and relative positions may differ with additional oxides and sample preparation

| 2-θ ± 0.2° | Relative Height |
|---|---|
| 9.05 | 42.6 |
| 10.44 | 100.0 |
| 12.40 | 29.7 |
| 14.73 | 27.6 |
| 17.35 | 32.0 |
| 22.76 | 31.2 |
| 22.93 | 34.7 |
| 23.52 | 24.0 |
| 25.82 | 24.9 |
| 26.01 | 31.7 |

Synthetic molecular sieves, particularly zeolites (e.g. aluminosilicates) are typically synthesized by mixing sources of alumina and silica in an aqueous media, often in the presence of a structure directing agent. The structure of the molecular sieve formed which includes STW framework is determined in part by solubility of the various sources, silica-to-alumina ratio, nature of the cation, synthesis conditions (temperature, pressure, mixing agitation), order of addition, type of OSDA, time of maintaining the reaction mixture and additional conditions identifiable by a skilled person. The aluminosilicate has catalytic activity due to the acid sites in the material.

As with pure silica molecular sieves, topologies of the molecular sieves of pure tin(IV) oxide, titanium(IV) oxide, zirconium(IV) oxide, cerium (IV) oxide and hafnium(IV) oxide depend on the ratios of various components in the reaction mixture, as well as the reaction conditions as will be understood by a skilled person.

1011711n addition to the conditions described herein, U.S. patent application Ser. Nos. 14/517,793 and 14/602,449 describe conditions which appear to be suitable for the formation of pure silica STW topologies.

U.S. patent application Ser. No. 14/517,793, filed Oct. 17, 2014 also describes the use of imidazolium monoquat OSDAs to form structures of STW topologies, for example including the use of penta methylimidazolium cations at $H_2O/SiO_2$ ratios of 4 to 7, at temperatures ranging from 140° C. to 175° C. and at $H_2O/SiO_2$ ratio of 17, at 175° C. and at using 2-ethyl-1,3,4-trimethyl-1H-imidazol-3-ium cations $H_2O/SiO_2$ ratios of 4 to 7, at temperatures ranging from 140° C. to 175° C.

U.S. patent application Ser. No. 14/602,449, filed Jan. 22, 2015 describes the use of several imidazolium monoquats and linked imidazolium diquats for form pure silica structures of STW topologies using fluoride (HF) mineralizing agents, for example using 2-ethyl, 1, 3-dimethyl imidazolium cations at $H_2O/SiO_2=2$ and 4 at 175° C., pentamethyl imidazolium cation at $H_2O/SiO_2=4$ and 7 at 175° C., and 3- and 4-carbon linked tetramethyl di-imidizolium diquats at $H_2O/SiO_2=4$ at 175° C.

General Approach

Several inherently chiral molecular sieves have been synthesized to date (although the bulk, polycrystalline samples are racemic), including: *BEA, CZP, GOO, -ITV, JRY, LTJ, OSO, SFS, and STW (molecular sieve framework types are designated by three-letter codes that define the unique connectivity of the oxide tetrahedral). In particular, several studies have reported polymorph A (that possesses a chiral helical pore) enriched *BEA. However, zeolite *BEA is limited in that the material crystallizes as highly faulted intergrowths of a racemic mixture of polymorphs A and polymorph B (achiral). In 1992, Lobo and Davis discussed the concept of synthesizing a chiral *BEA molecular sieve via the use of a chiral OSDA, and reported low enantio-enrichment (ee) for both a chemical reaction and an adsorption experiment (see Davis M E, Lobo R F (1992) Zeolite and molecular sieve synthesis. *Chem Mater* 4(4):756-768). Recently, Tong et al. have reported a high-fluoride method of synthesizing polymorph A enriched *BEA using achiral OSDAs (although difficult to understand the origin of the proposed enantio-enrichment), and reported low ee's from a chemical reaction (Tong M, et al. (2015) Synthesis of chiral polymorph A-enriched zeolite Beta with an extremely concentrated fluoride route. *Sci Rep* 5:11521.). Other authors have reported samples enriched in polymorph A with similar ambiguity in enantioenrichment.

These studies suggested the possibility of synthesizing an enantioenriched, chiral molecular sieve. However, the inherent difficulty in controlling the synthesis of polymorphic domains, and the enantiomeric domains of only polymorph A in *BEA, has made it very problematic to conclusively prove that a bulk sample of a molecular sieve does in fact have an enantiomerically enriched framework content. Lobo and Davis discussed this issue and suggested that a preferred approach would be to design syntheses that target chiral molecular sieve structures where individual crystals are single enantiomorphs (microporous analogs to quartz) (15). The STW framework is an example of this type of molecular sieve, since recent evidence shows that each individual crystal is a single enantiomorph (i.e., there are no polymorph or opposite enantiomeric domains within a single crystal).

In 2008 a molecular sieve denoted SU-32 was disclosed, that was later given the framework code of STW. This material was prepared from a fluoride mediated synthesis with diisopropylamine as the OSDA and a gel composition of:

$GeO_2:TEOS:DIPA:H_2O:HF=1.0:0.8:79.3:27.7:3.5$ (i.e., 0.8 $SiO_2$:1 $GeO_2$:79.3 DIPA:3.5 HF:27.7 $H_2O$, claimed Si/Ge=0.8-2.1 in gel gave SU-32). The product was found to have Si/Ge=0.85, though the product was contaminated with $GeO_2$ and SU-32 often existed along with another material, SU-15. As expected for a material containing a high amount of material the framework was only stable to calcination at 400° C., although the diisopropylamine was removed by 300° C. (it is unclear if the variable temperature PXRD was performed in dry air). The STW framework is one that exhibits intrinsic chirality, meaning the framework, channel system and cavity all have a hand. The framework consists of helical 10 MRs that are intersected by 8 MRs. All the 10 MRs within a single crystal will have the same handedness. This material generated significant interest as it was the first known, intrinsically chiral material that could be prepared with single crystals that are pure enantiomers (not intergrowths as with *BEA). However, the limited thermal and especially hydrothermal stability of this high-germanium material limited the practical applications, until a higher-silica version could be found. Pure-silica STW was reported in 2012, even though theoretical studies argued this material was not possible due to framework strain. This material was formed from the achiral OSDA 2-ethyl-1,3-dimethylimidazolium and was found to exhibit robust hydrothermal stability and a later study confirmed that individual crystals showed a single handedness. The synthesis of a hydrothermally stable version of STW brought this material significant interest in our lab if a method could be made to synthesize bulk, enantiopure samples of the material. Based on many previous theories we believed that a chiral, enantiopure OSDA large enough to impart chirality on the framework (has a chiral twist) would be required to do this. In order to do this we believed that a computational method would be needed to "design" such an OSDA. Recently a computational method has been developed that is capable of predicting chemically synthesizable OSDAs for desired microporous material frameworks. This is a significant improvement over previous prediction methods which often yielded OSDAs that were impractical to synthesize. This method was applied to STW without the restriction of chirality, as proof of concept for the method, and indeed it was able to predict a number of different imidazolium OSDAs for STW. One of the predicted ODSAs, pentamethylimidazolium, was found to be a significantly better OSDA for STW than the previously reported imidazolium. The method has more recently been verified for two additional zeolites, AEI (SSZ-39) and SSZ-52 (SFW). Inspired by previous other work with STW, the present inventors biased the experimental work that found that diquats formed from tetramethylimidazole led to pure silica STW. The top scoring results from this computational study are shown in Table 2 along with the predicted stabilizations energies of the various enantiomers of the OSDAs in the P6$_1$22 along with the OSDA in the other framework enantiomer. Initial attempts focused on OSDA 1, which showed a very favorable stabilization energy, as a pure enantiomer as the starting material for this OSDA can be purchased enantiopure (based on various stereomers and enantiomers of 4-hydroxy-proline) but the synthesis was complicated by the existence of the non-quaternary amine in the final product. Ultimate efforts focused on OSDA 2.

This design (shown in FIG. 1) provided for the synthesis of either the "R" or the "S" enantiomers of STW, thus yielding materials that enable appropriate control experiments when elucidating structures and functions.

The following listing of embodiments is intended to complement, rather than displace or supersede, the previous descriptions.

Embodiment 1

A crystalline microporous solid comprising:
(a) silicon oxide, germanium oxide, or combination thereof; and optionally
(b) aluminum oxide, boron oxide, cerium oxide, gallium oxide, hafnium oxide, iron oxide, tin oxide, titanium oxide, indium oxide, vanadium oxide, zirconium oxide, or combination thereof, wherein
the microporous solid exhibits a chiral morphology and an enantiomeric excess ("ee") of one enantiomer of at least 5%, 10%, 15%, 20%, 25%, 50%, 75%, or 90% to about 100%. In some Aspects of this Embodiment, the crystalline microporous solid having chiral morphology has STW topology. In some aspects of this Embodiment, the chiral morphology is determined by HRTEM. In some embodiments, the crystalline microporous solid is a bulk polycrystalline enantiomerically enriched microporous powder, as opposed to a single crystal of material.

In one embodiment, synthetic molecular sieves include silica (or a source of silica) with one additional tetravalent element oxide (i.e. MO$_2$, wherein M refers to a tetravalent element other than silicon) selected from the group consisting of tin(IV) oxide, titanium(IV) oxide, zirconium(IV) oxide, cerium (IV) oxide and hafnium(IV) oxide. The silica/MO$_2$ are typically synthesized by mixing silica with one of the sources of tin(IV) oxide, titanium(IV) oxide, zirconium (IV) oxide, cerium (IV) oxide and hafnium(IV) oxide, in the presence of an organic structure directing agent such as an amine or a quaternary ammonium. As with molecular sieve of pure silica, molecular sieve of SiO$_2$/MO$_2$ depends on the ratios of various components in the reaction mixture, as well as the reaction conditions as will be understood by a skilled person.

Embodiment 2

The chiral crystalline microporous solid of Embodiment 1 that is a pure silicate, an aluminosilicate, a borosilicate, a germanosilicate, a titanosilicate, a germanoaluminosilicate, or a germanotitanosilicate.

Embodiment 3

The chiral crystalline microporous solid of Embodiment 1 or 2, having a STW topology. In some aspects, the crystalline microporous solid is a pure silicate of STW topology, a germanosilicate of STW topology having a Si/Ge ratio in a range of from 1 to 20, and/or a aluminosilicate of STW topology having an Si/Al of 75-200. In certain aspects of this Embodiment, the crystalline microporous solid comprises D4R rings in the framework.

Embodiment 4

The chiral crystalline microporous solid of any one of Embodiments 1 to 3, further comprising an Organic Structure Directing Agent (OSDA) occluded within pores of the microporous solid, as determined by Circular Dichroism Analysis, the OSDA comprising a structure having a linked pair of imidazolium cations of a structure:

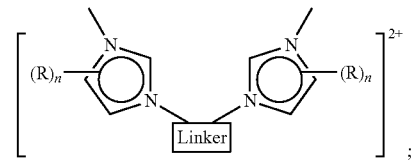

wherein Linker is a 2, 3, 4, 5, or 6-membered chiral linking group, preferably a 4, 5, or 6-membered chiral linking group, including cyclic and alicyclic chiral linking groups, preferably a chiral linking group comprising a saturated cyclic chiral linking group; and R is independently methyl or ethyl, preferably methyl; and n is independently 0, 1, 2, or 3, preferably 2 or 3.

Embodiment 5

The chiral crystalline microporous solid of Embodiment 4, wherein Linker comprises a chirally substituted cyclopropane, aziridine, epoxide, cyclobutane, cyclopentane, cyclohexane, tetrahydrofuran, pyrrolidine, or tetrahydrothiophene.

Embodiment 6
The chiral crystalline microporous solid of Embodiment 4 or 5, wherein Linker comprises a structure:
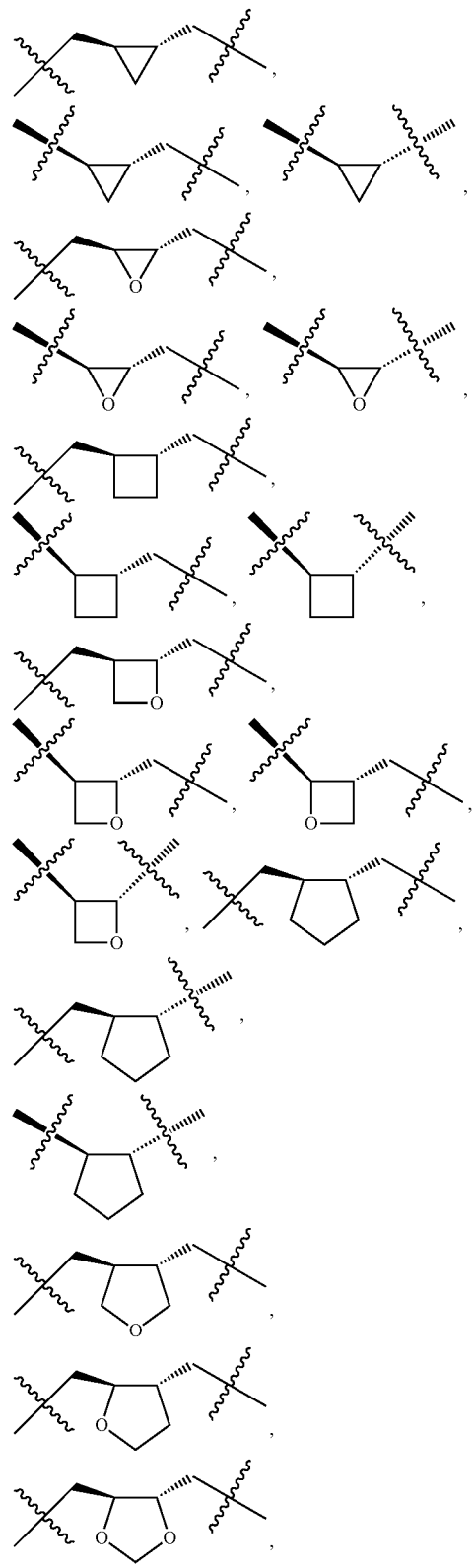
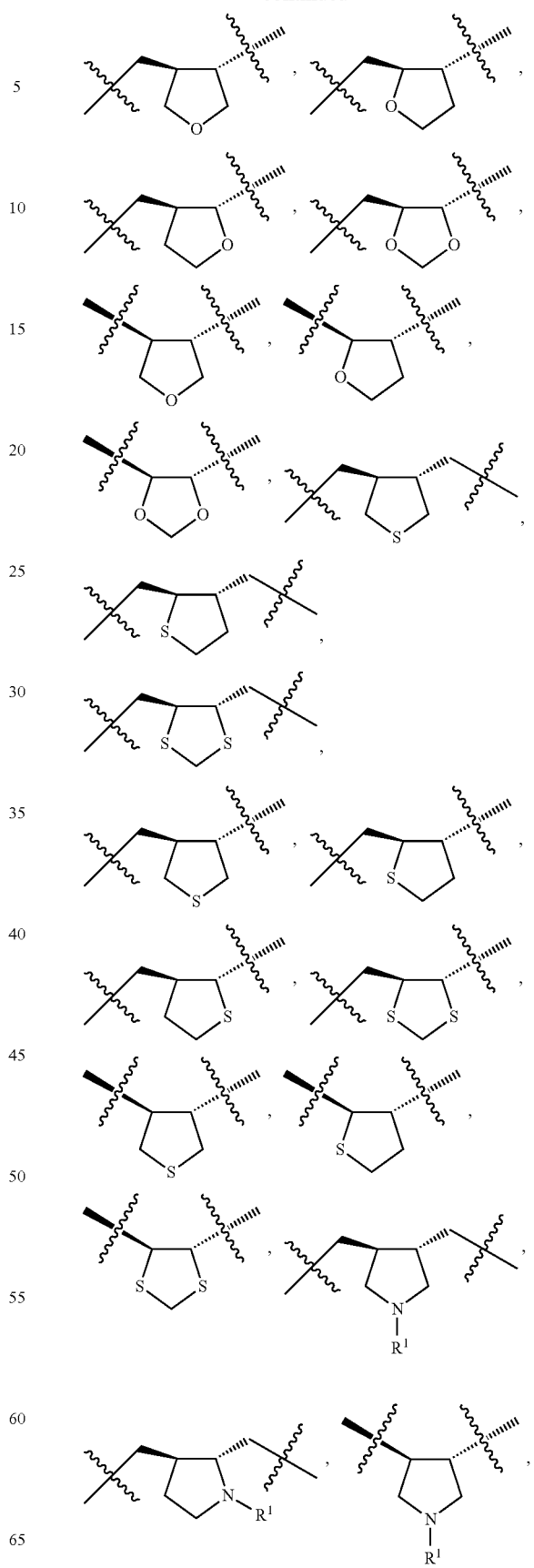

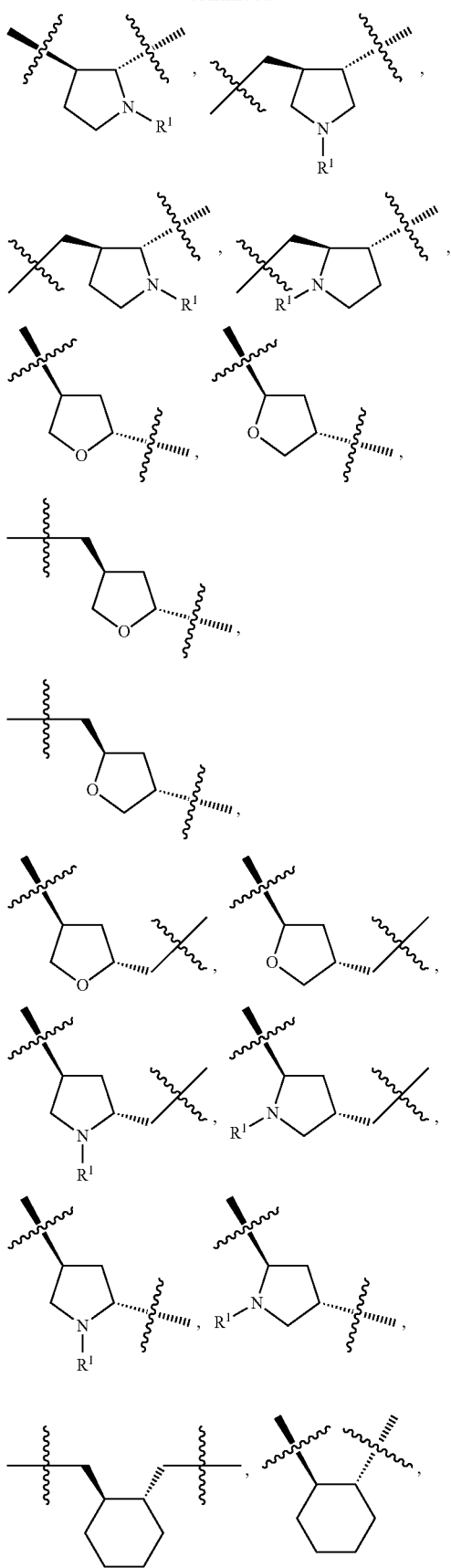
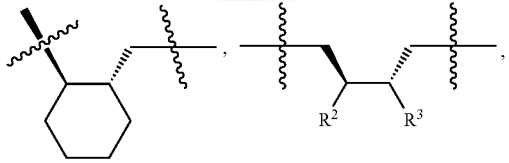
or a chiral enantiomer thereof, where $R^1$ is H or $C_{1-6}$alkyl, $R^2$ and $R^3$ are independently alkyl or aryl, preferably $C_{1-12}$ alkyl or aryl.
Embodiment 7
The chiral crystalline microporous solid of Embodiment 4 or 5, wherein Linker comprises a structure:
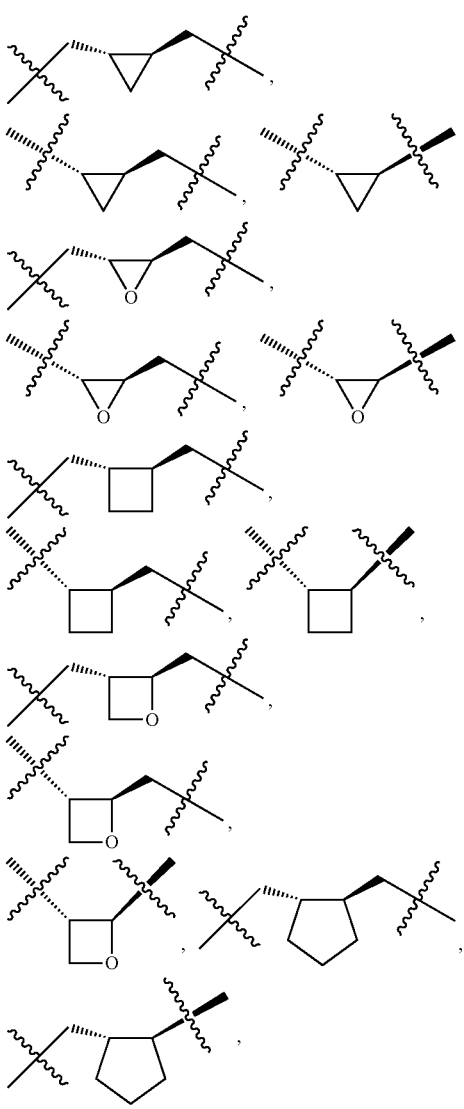

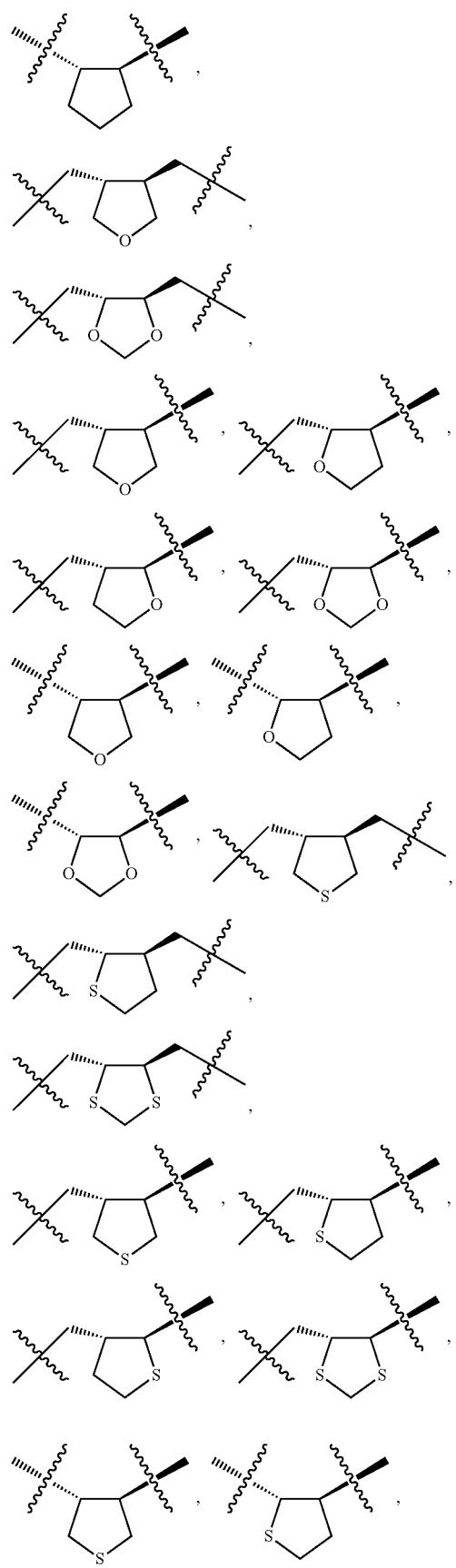
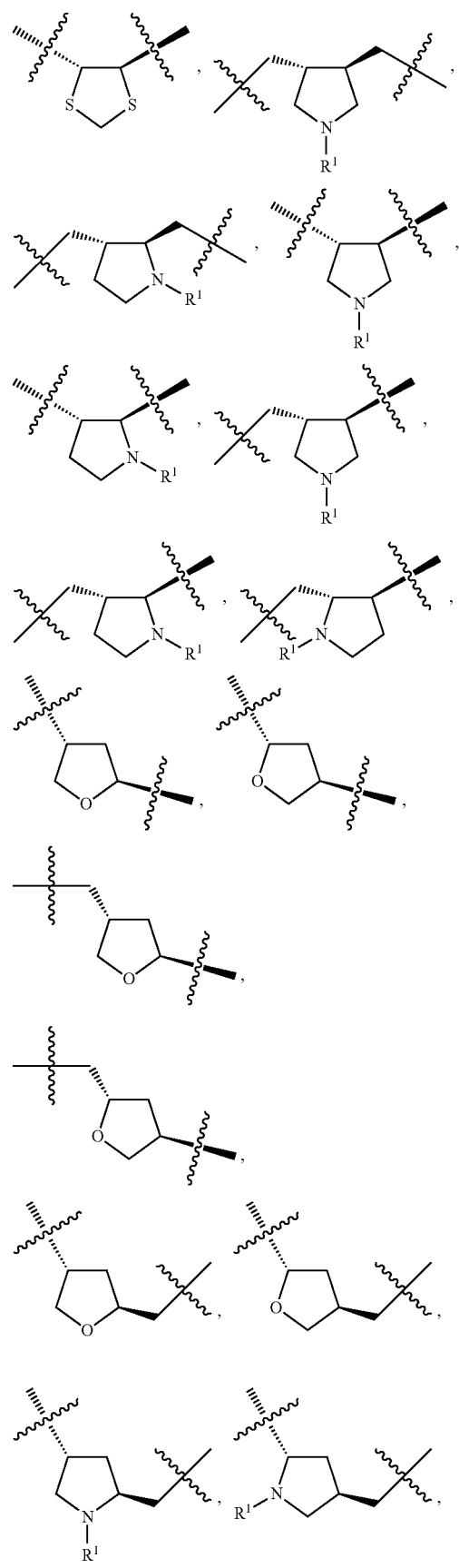

37
-continued

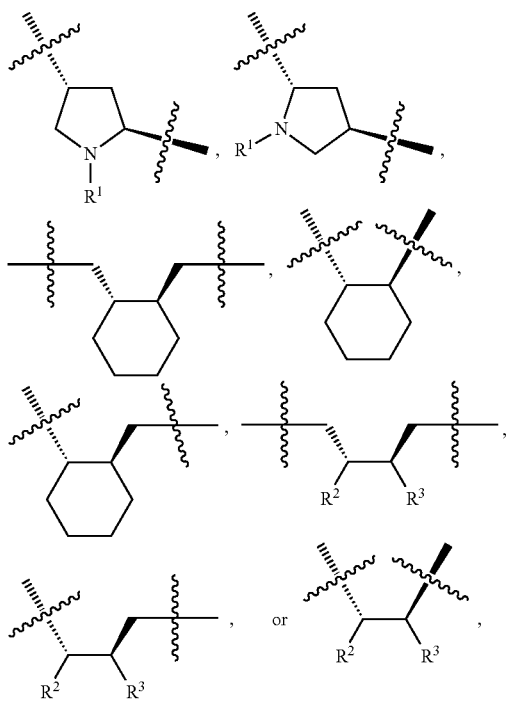

or a chiral enantiomer thereof, where $R^1$ is H or $C_{1-6}$alkyl, $R^2$ and $R^3$ are independently alkyl or aryl, preferably $C_{1-12}$ alkyl or aryl.

Embodiment 8

The chiral crystalline microporous solid of any one of Embodiments 1 to 3, that is substantially free of occluded organic material, the crystalline microporous solid being predominantly in a hydrogen form.

Embodiment 9

The chiral crystalline microporous solid of any one of Embodiments 1 to 3, calcined and either in its hydrogen form or containing at least one alkali metal cation, alkaline earth metal dication, or transition metal or transition metal oxide within its pores. For example, in certain Aspects of this Embodiment, the chiral crystalline microporous solid contains scandium, yttrium, tin, titanium, zirconium, vanadium, manganese, chromium, molybdenum, tungsten, iron, ruthenium, osmium, cobalt, rhodium, iridium, nickel, palladium, platinum, copper, silver, gold, or mixtures thereof, each as a metal, oxide, or salt. In one Aspect of this Embodiment, the pores contain copper, as metal, oxide, or salt.

Embodiment 10

The chiral crystalline microporous solid of any one of Embodiments 1 to 3, calcined and containing Li, Na, K, Rb, Cs, Be, Mg, Ca, Sr, Be, Al, Ga, In, Zn, Ag, Cd, Cu, Fe, Co, Ni, Ru, Rh, Pd, Pt, Au, Hg, La, Ce, Pr, Nd, Pm, Sm, Eu, or $R_{4-n}N^+H_n$ cations in its pores, where R is alkyl, n=0-4.

In certain aspects, the crystalline microporous solid of any one of the preceding Embodiments exhibits one or more of the spectroscopic characteristics described herein.

38

Embodiment 11

A process comprising hydrothermally treating a composition comprising:
(a) at least one source of a silicon oxide, germanium oxide, or combination thereof;
(b) optionally at least one source of aluminum oxide, cerium oxide, boron oxide, gallium oxide, hafnium oxide, iron oxide, tin oxide, titanium oxide, vanadium oxide, zinc oxide, zirconium oxide, or combination or mixture thereof;
(c) either a source of fluoride or a source of hydroxide; and
(d) a linked pair of quaternary imidazolium cations of a structure:

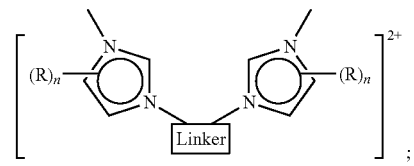

wherein Linker is a 2, 3, 4, 5, or 6-membered chiral linking group, preferably a 4, 5, or 6-membered chiral linking group, including cyclic and alicyclic chiral linking groups, preferably a chiral linking group comprising a saturated cyclic chiral linking group; and R is independently methyl or ethyl, preferably methyl; and n is independently 0, 1, 2, or 3, preferably 2 or 3, under conditions effective to crystallize a crystalline microporous solid that exhibits a chiral morphology and has enantiomeric excess ("ee") of at least 5%, 10%, 15%, 20%, 25%, 50%, 75%, or 90%. In certain aspects of this claim, the Linker is defined by a structure shown in claim 6.

Embodiment 12

The process of Embodiment 11, wherein the conditions are conducive to forming a chiral crystalline microporous silicate composition having STW topology (such conditions are known for other OSDAs, such as U.S. patent application Ser. No. 14/517,793, filed Oct. 17, 2014)

Embodiment 13

The process of Embodiment 11 or 12, wherein the hydrothermally treating is done at a temperature in a range of from about 100° C. to about 200° C. for a time effective for crystallizing the crystalline microporous solid.

Embodiment 14

The process of any one of Embodiment 11 to 13, further comprising isolating the enantiomerically enriched crystalline microporous solid.

Embodiment 15

The process of Embodiment 14, further comprising calcining the isolated crystalline microporous solid at a temperature in a range of from about 350° C. to about 850° C.

Embodiment 16

The process of Embodiment 15, further comprising treating the calcined material with an aqueous ammonium salt.

Embodiment 17

The process of Embodiment 16, further comprising treating the calcined crystalline microporous solid with at least one transition metal or transition metal oxide.

Embodiment 18

A method of selectively adsorbing a chiral organic molecule comprising contacting a stereoisomeric mixture of the organic molecule with a crystalline microporous solid any one of Embodiments 1 to 10 or prepared by a process of any one of the processes of Embodiments 11 to 17.

Embodiment 19

A method of preparing an enantiomerically enriched organic molecule product from achiral precursor, the method comprising conducting a chemical reaction to form the organic molecule product in the presence of the crystalline microporous solid any one of Embodiments 1 to 10 or prepared by a process of any one of the processes of Embodiments 11 to 17.

Embodiment 20

The method of Embodiment 19, wherein the chemical reaction is an asymmetric epoxide ring-opening reaction. In certain Aspects of this Embodiment, the chemical reaction is a chiral olefin oxidation, for example proceeding through an epoxide intermediate.

Embodiment 21

The method of Embodiment 19, wherein the chemical reaction is an asymmetric hydrogenation reaction.

Embodiment 22

The method of Embodiment 19, wherein the chemical reaction is an asymmetric dihydroxylation, oxyamination, hydride transfer, hydrosilylation, hydroboration, hydrovinylation, hydroformylation, hydrocarboxylation, isomerization, allylic alkylation, cyclopropanation, Diels-Alder reaction, Heck reaction, isomerization, Aldol reaction, Michael addition, or epoxidation.

EXAMPLES

The incorporated Examples are provided to illustrate some of the concepts described herein. While each Example is considered to provide specific individual embodiments of composition, methods of preparation and use, none of the Examples should be considered to limit the more general embodiments described herein. In fact, the description described in the Examples may be interpreted in terms of the more general teachings herein.

In the present disclosure, enantiopure organic structure directing agents (OSDAs) were used to synthesize enantio-enriched, polycrystalline molecular sieve samples of a specific enantiomer. Computational results correctly predicted which enantiomer would be obtained, and the enantiomeric enrichment was shown by high-resolution transmission electron microscopy. The enantioenriched and racemic samples of the molecular sieves were tested as adsorbents and heterogeneous catalysts. The enantio-enriched molecular sieves showed enantioselectivity for the ring opening reaction of epoxides and enantioselective adsorption of 2-butanol (R enantiomer of the molecular sieve shows opposite and approximately equal enantioselectivity from the S enantiomer of the molecular sieve, while the racemic sample of the molecular sieve showed no such enantioselectivity).

The enantio-enriched polycrystalline samples of a molecular sieve can also function as adsorbents to separate chiral molecules and as a heterogeneous catalyst to perform enantiospecific reactions. This initial demonstration proved that bulk, enantio-enriched chiral zeolites and zeolite-like molecular sieves can be synthesized, and that this new type of solid can be used to prepare chiral, small molecules.

As shown elsewhere herein, the STW topology provided a unique opportunity to control the synthesis of either the R- or S-enantiomer (or both). While the STW can co-crystallize with many phases that form from the imidazolium-based syntheses, including CSV, IWV, and RTH (see Tables), the abundance of the D4R rings in the STW phase provides that germanium should aid in forming the STW framework. In a typical reaction, a high concentration of the OSDA (e.g., 0.5 mole OSDA per mole of $SiO_2$) was used to maximize its influence. Under the conditions tested, STW was found to crystallize in a range of Si/Ge=2 to 20 after between 5 and 21 days. STW crystals having Si/Al of 75 to 200 were also obtained.

Example 1: Directed Computational Design of a Chiral OSDA for STW

Schmidt et al. reported on the synthesis of STW utilizing a computationally predicted OSDA. This work demonstrated the feasibility of a priori predicting chemically synthesizable monoquaternary, imidazolium OSDAs to create a specified, fluoride-mediated, pure-silica framework. Additionally, STW has been reported to form using diquaternary imidazolium-based OSDAs that are of sufficient size to conform to 10 MR channel structure, implying more rigid, chiral analogues may be included in the framework of STW, and may potentially impart structural chirality. Here, we implemented the previously published computational method implemented by Schmidt et al., and utilized the molecular design constraints suggested by Lobo and Davis. The computational method was modified, such that a given enantiomer of each potential OSDA molecule was simulated in both enantiomers of STW, with successful candidates producing a strong stabilization in only a single enantiomer. Based on our previous work with STW, we believed that a computed stabilization energy larger than $-15$ kJ-(mol Si)$^{-1}$ would be needed in order to form STW. Ultimately, a single OSDA candidate was selected (Table 2). Relative to the other predicted OSDAs for STW, OSDA 2 has the largest energy difference between enantiomers, making it the most suitable target for experimental evaluation. Coupled with energy predictions, this molecule was also selected after ensuring that the both enantiomers were synthetically attainable.

TABLE 2

Potential chiral OSDAs including OSDA 2, that was used to prepare enantioenriched STW, and their associated stabilization energies in both enantiomers of the STW framework (stabilization energies in kJ − (mol Si)$^{-1}$).

| Organic | Stabilization Energies (kJ/mol Si) Enantiomer 1, P6$_1$22 | Stabilization Energies (kJ/mol Si), Enantiomer 2, P6$_5$22 | Designation |
|---|---|---|---|
| [structure] | −16.32 | −14.60 | OSDA 1 |
| [structure] | −15.27 | −1.58 | OSDA 2 |
| [structure] | −14.65 | −1.37 | OSDA 3 |
| [structure] | −13.83 | 0.532 | OSDA 4 |

Example 2: Synthesis and Characterization of Enantiopure OSDA 2

Figure 2:
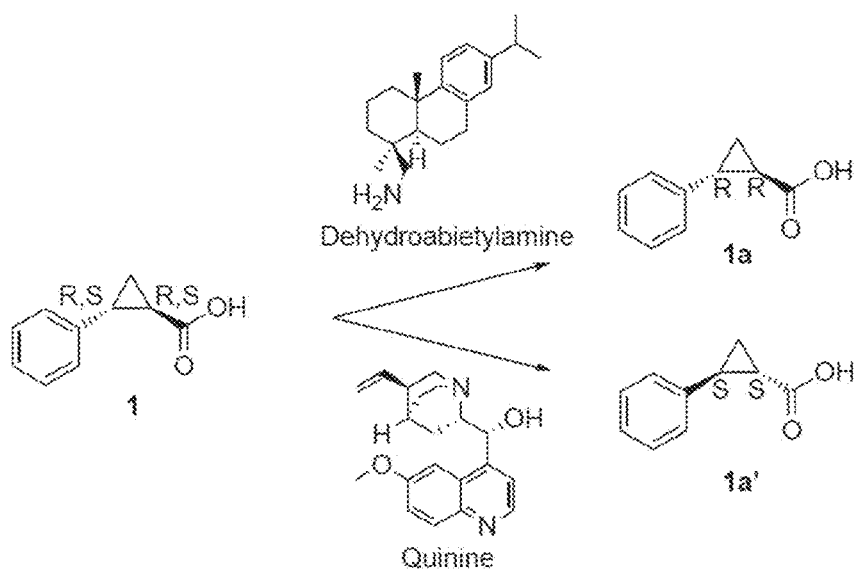
FIG. 2 provides a schematic illustration of the chiral resolution scheme of trans-2-phenylcyclopropane-1-carboxylic acid using dehydroabietylamine or quinine to yield 1a or 1a', respectively.
Figure 3:
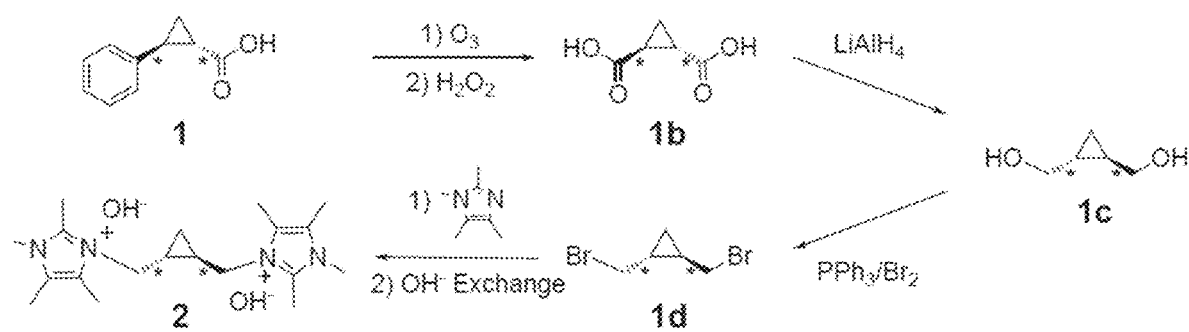
FIG. 3 provides a schematic illustration of the scheme for the synthesis of the racemic OSDA 2 from 1. Note that the same synthesis procedure can be applied to 1a or 1a' to yield R-2 or S-2, respectively.

Detailed procedures for the chiral resolution and reaction schemes used to synthesize OSDA 2 are given in FIGS. 2 and 3. A summary of the synthesis method implemented to develop both the R- and S-enantiomers of the organic structure directing agent used in this study is detailed in FIG. 2 (chiral separation) and FIG. 3 (reaction pathway).

Figure 4:
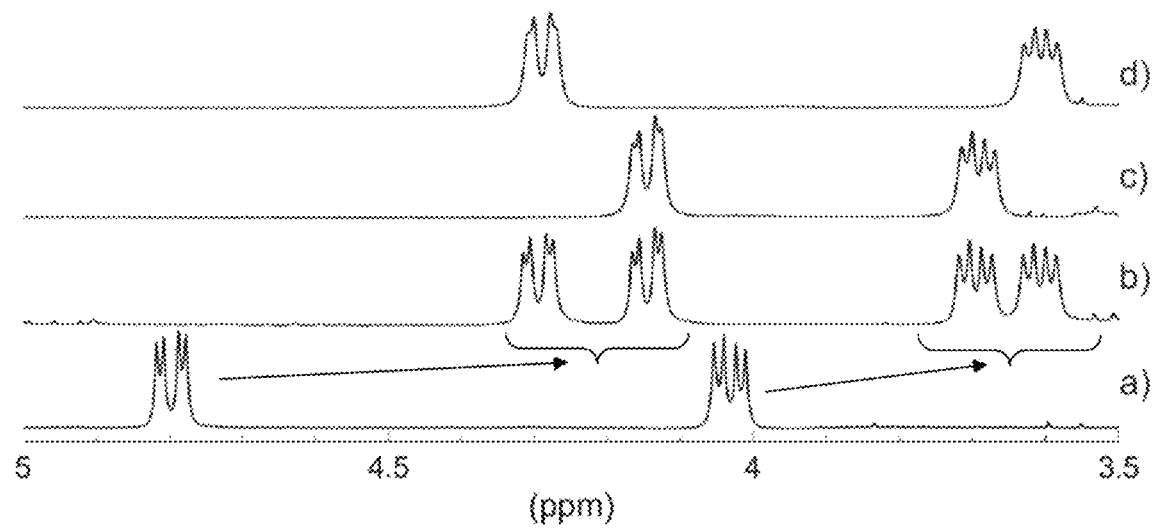
FIG. 4 shows the results of $^1$H NMR chiral shift experiments to analyze the enantiopurity of 2: a) neat racemic OSDA 2, b) racemic OSDA 2 with BINPHAT, c) R-2 with BINPHAT, d) S-2 with BINPHAT. An imidazole methyl resonance in a) has been suppressed at δ 3.74 ppm for clarity.

Chiral resolution of the starting compound (trans-2-phenylcyclopropane-1-carboxylic acid, 1) was performed by successive crystallizations with either dehydroabietylamine (DHBA) or quinine as chiral derivatization agents to obtain the R (1a) or S (1a') forms of the starting material (FIG. 2). Polarimetry measurements were taken for the salt and free-acid forms of 1a and 1a' to confirm enantiopurity, after the separation was complete. Note: enantiomers of OSDA 2 are denoted herein as R-2 and S-2. (Λ,R)-BINPHAT tetrabutylammonium salt was used as a chiral shift reagent to detect the enantiopurity of OSDA 2 after executing the reactions outlined in FIG. 3. As shown in FIG. 4, the neat product $^1$H NMR resonances at δ 4.80 and 4.04 ppm are singular and distinct multiplets. Addition of BINPHAT to a racemic sample of 2 results in a twofold spectral change: 1) a distinct shift upfield of only the aforementioned peaks from their initial position, and 2) an observed peak split. Integration of the split peaks indicates that they maintain a 1:1 ratio, expected for a racemic compound. However, the two enantiomers of 2 show only a single peak. This method confirms the enantiopurity of OSDA 2, and demonstrates that no racemization occurs throughout the organic synthesis scheme.

Example 2.1: Separation of the Enantiomers of OSDA 1

Several methods have been described to separate what are denoted the (−)-R (1a) and (+)-S (1a') enantiomers of trans-2-phenylcyclopropanecarboxylic acid (1) using either quinine and brucine or dehydroabietylamine, respectively. In this work, brucine was avoided due to the toxicity of this compound.

Example 2.2: Chiral Resolution of (1R,2R)-2-Phenylcyclopropane-1-carboxylic acid (1a)

The purification of dehydroabietylamine was conducted by the method reported by Gottstein (5). 900 g of dehydroabietylamine was dissolved in 1.5 liters of toluene. Then a solution of 210 g of glacial acetic acid in 500 mL of toluene was added. The solution was then refrigerated overnight and the product was collected via filtration and washed with cold toluene. The product was recrystallized one time from toluene and washed with hexane and dried under vacuum to yield 490 g of purified dehydroabietylamine acetate.

Dehydroabietylamine acetate (490 g) was dissolved in 630 mL of boiling water. Then 500 mL of 10% NaOH solution were added. After the mixture was chilled it was extracted several times with diethyl ether, the combined extracts were washed with water and dried over anhydrous potassium carbonate. The ether was then removed using rotary evaporation to yield 357 g of a yellow oil that slowly solidified.

The enantiopurification was performed according to the method of Cheng et al. (4). 150 g of 1 (racemic mixture from Aldrich, MW=162.19, 925 mmol) was dissolved in 940 mL of warm methanol. Then 263 g of purified dehydroabietylamine (925 mmol) was dissolved separately in 750 mL of warm methanol. The two solutions were slowly combined (Caution: Exothermic process, use caution) and, after sitting at room temperature overnight, the resultant solid salt of dehydroabietylamine and 1a was recovered using filtration and was then recrystallized from 90% aqueous methanol six times to yield a solid with a rotation of $[\alpha]_D^{20}$ −81° (c 0.42, MeOH) (literature: $[\alpha]_D^{20}$ −80.8° (c 0.61, MeOH)) (4). The total mass of recovered solids was 78.5 g.

The free acid was isolated by adding the salt dehydroabietylamine and 1a to a saturated solution of NaHCO3 and then extracting with diethyl ether. The aqueous fraction was then acidified with 37% hydrochloric acid followed by successive extractions with diethyl ether. The organic extractions were combined, dried over anhydrous magnesium sulfate and then the solvent removed using rotary evaporation to yield 18.1 g of enantiopure 1a. The rotation of 1a in chloroform was found to be $[\alpha]_D^{20}$ −375.6° (c 1.07, $CHCl_3$) (literature: $[\alpha]_D^{20}$ −401° (c 0.88, $CHCl_3$)) (4).

Example 2.3: Chiral Resolution of (1S,2S)-2-Phenylcyclopropane-1-carboxylic acid (1a')

Following the method of Cheng et al. and Overberger et al., 125 g of 1 (racemic mixture from Aldrich, MW=162.19, 771 mmol) were added to 250 g of quinine (Aldrich, MW=324.42, 771 mmol) in 4 L of ethyl acetate at reflux (3, 4). The mixture was then allowed to cool to room temperature and allowed to sit at room temperature for 1 week, over which time large white crystals of the salt of quinine and 1a' precipitated from the solution. The crystals were recovered by filtration, and the filtrate was then recrystallized an additional 5 times from ethyl acetate to yield a white product with a rotation of $[\alpha]_D^{20}$ −10.0° (c 1.0, EtOH) (literature: $[\alpha]_D^{20}$ −10.2° (c 1.0, EtOH)] (4). The total yield of the salt at was 95.1 g.

The free-acid product was recovered by dissolving 46.6 g of the salt of quinine and 1a' in 500 mL of 1 M HCl at room temperature. 1a' was then recovered by extraction with diethyl ether to yield 15.0 g. The rotation of 1a' in chloroform was found to be $[\alpha]_D^{20}$+370.8° (c 1.07, $CHCl_3$) (literature: $[\alpha]_D^{20}$+406° (c 1.0, $CHCl_3$)) (4).

For both 1a and 1a', further crystallization steps did not alter the polarimetry experiments. Additionally, the $^1$H NMR of both compounds was identical to the starting material ($CDCl_3$, 500 MHz): δ 7.0-7.2 (m, 5H, Ph), 2.52 (m, 1H), 1.83 (m, 1H), 1.59 (m, 1H), 1.33 (m, 1H).

The synthesis procedures detailed below are written from the perspective of using a racemic starting material. However, the exact same procedures can be applied for the enantiopure starting materials 1a and 1a' to obtain R-2 and S-2, respectively.

Example 2.4: Trans-2-phenylcyclopropane carboxylic acid (1) to trans-1,2-cyclopropane carboxylic acid (1b)

Compound 1b was prepared by ozonolysis of 1 (either enantiomer, or the racemic mixture) in acetic acid according to the procedure reported by Inouye et al. (6). In a typical synthesis 11.6 g of 1a (MW=162.19) was dissolved in 200 mL of glacial acetic acid. A stream of ozone was bubbled through the mixture with stirring (125 mL/minute of 6.7% ozone in 02) at 50° C. The mixture was allowed to react for 36 hours. The reaction was cooled, and 50 mL of 30% aqueous $H_2O_2$ was added and stirred overnight. All liquid was then removed using vacuum distillation. Then, an additional 50 mL of 30% aqueous $H_2O_2$ was added, stirred for several hours, and the liquid again removed using vacuum distillation. This was repeated a total of 4 times, and the recovered solids were dried under vacuum. A total of 7.49 g of solid 1b was recovered (MW=130.10). $^1$H NMR ($D_2O$, 500 MHz): δ 2.04 (m, 2H), 1.39 (m, 2H). $^{13}$C NMR ($D_2O$, 500 MHz): δ 175.7, 22.1, 15.3.

Example 2.5: Trans-1,2-cyclopropane carboxylic acid (1b) to Trans-1,2-cyclopropane diol (1c)

The procedure for the reduction of 1b to 1c was adapted from Taylor et al. (7) 200 mL of THF in a 1 L round-bottom flask (RBF) were cooled in an ice bath under a nitrogen atmosphere. Then 14.95 g of LiAlH4 was slowly added and stirred for 1 hour. 25 g of 1b (Aldrich) was dissolved in THF and the slowly added to the LiAlH4 suspension using a dropping funnel. After the addition was complete the mixture was stirred at 0° C. for 2 hours. Then, the RBF was removed from the ice bath and slowly allowed to warm up to room temperature and stirred for 2 hours. Finally, the reaction was heated to reflux and stirred overnight. The mixture was then cooled in an ice bath and 60 g of saturated ammonium chloride solution was slowly added, followed by 100 mL of ethyl acetate. The suspension was stirred for 4 hours and then filtered. The retentate was resuspended in additional ethyl acetate, stirred an additional 4 hours and then filtered once again. The liquid filtrate was combined and dried over magnesium sulfate. After removing the magnesium sulfate by filtration, the solvent was removed using rotary evaporation to yield a yellow oil. The yield of 1c was 9.54 g (93.4 mmol, 70%) and was used without further purification. $^1$H NMR ($CDCl_3$, 500 MHz): δ 5.05 (s, 2H), 3.76 (m, 2H), 3.07 (m, 2H), 1.01 (m, 2H), 0.43 (m, 2H). $^{13}$C NMR ($CDCl_3$, 500 MHz): δ 65.8, 19.8, 7.2.

Example 2.6: Trans-1,2-cyclopropane diol (1c) to Trans-1,2-dibromocyclopropane (1d)

Compound 1d was prepared following a method reported by de la Fuente et al. (8). In a typical reaction, 16.04 g of bromine was added to a solution of 26.32 g triphenylphosphine in dry acetonitrile (200 mL) at 273 K. A solution of 5 g of 1c in dry acetonitrile (100 mL) was added to the reaction mixture, which was then stirred under an argon purge overnight at room temperature. Remaining acetonitrile was subsequently evaporated to yield a clear oil as well as a white triphenylphosphine oxide solid. This crude mixture was finely dispersed in hexane (2×250 mL) and filtered to remove the triphenylphosphine oxide. The hexane solution was evaporated under vacuum to give 4.0 g of 1d. If necessary, 1d was purified using column chromatography on silica gel with hexane/ethyl ether (95:5) as the eluent. $^1$H NMR ($CDCl_3$, 500 MHz): 3.35 (m, 4H), 1.33 (m, 2H), 0.86 (m, 2H). $^{13}$C NMR ($CDCl_3$, 500 MHz): 37.0, 24.4, 17.3.

Example 2.7: Trans-1,2-dibromocyclopropane (1d) to Final OSDA Product (2)

Compound 1d was dissolved in chloroform and then a 10% excess of tetramethylimidazole was added and the solution was refluxed overnight. After the reaction was complete, the reaction mixture was cooled to room temperature and then the diquaternary product was extracted using water (3 times). The water was removed using rotary evaporation and the resulting solid was then dried under vacuum overnight. Finally, the product was recrystallized from chloroform to yield a white product in quantitative yield. $^1$H NMR (CDCl$_3$, 500 MHz): δ 4.80 (m, 1H), 4.04 (m, 1H), 3.74 (s, 3H), 2.99 (s, 3H), 2.31 (s, 3H), 2.24 (s, 3H), 1.73 (m, 1H), 0.85 (t, 2H). $^{13}$C NMR (CDCl$_3$, 500 MHz): δ 143.2, 125.8, 125.1, 48.2, 32.8, 17.4, 12.4, 10.6, 9.5, 9.1.

Prior to use in inorganic syntheses, 2 was ion exchanged to hydroxide form using Dowex Marathon A exchange resin and the final product concentration was determined using a Mettler-Toledo DL22 autotitrator using 0.01 M HCl as the titrant.

Example 2.8: Characterization of the Enantiopurity of 2

A survey of the literature finds that the enantiodiscrimination of quaternary (and diquaternary) ammonium compounds can be challenging. One method that has seen published success for this is the chiral shift reagent, Tetrabutylammonium[(Λ,R)-(1,1'-binaphthalene-2,2'diolato)(bis(tetrachlor-1,2-benzenediolato)phosphat(V)) (BINPHAT). In a typical NMR experiment, BINPHAT was mixed in equimolar amounts (according to charge) with OSDA 2 in boiling CDCl$_3$ and the product was studied using $^1$H NMR.

Example 3. Synthesis and Characterization of STW

Figure 5:
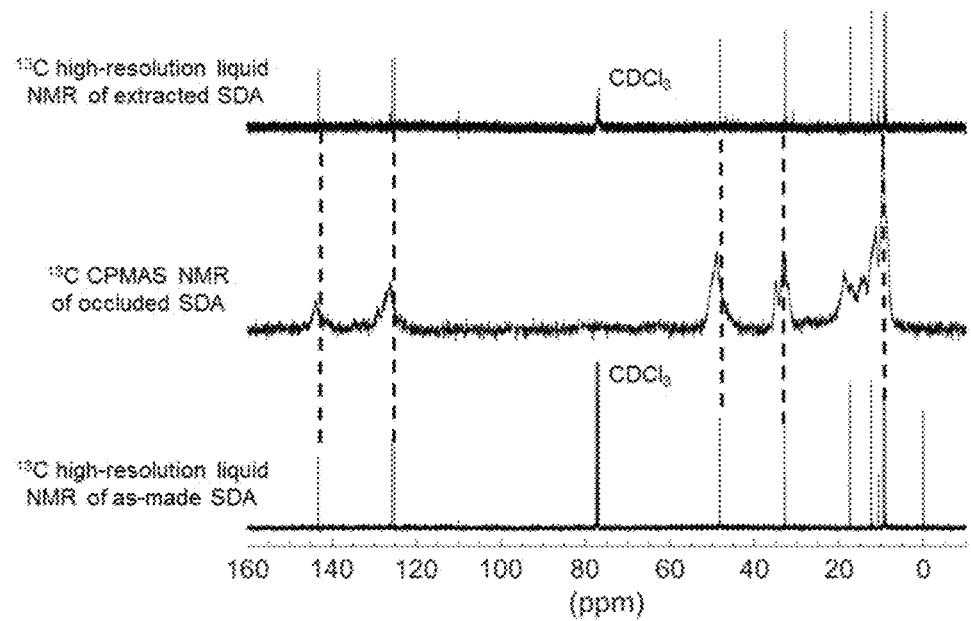
FIG. 5 shows a comparison of the $^{13}$C NMR collected for: a) the neat organic, b) the occluded organic within an enantioenriched STW sample, and c) the OSDA recovered dissolving the framework with hydrofluoric acid and extracting the organic.

Syntheses of STW were conducted with enantiopure samples of the R and S enantiomers of OSDA 2, as well as the racemic mixture of the two. These syntheses were performed at temperatures and H$_2$O/SiO$_2$ ratios that are typical for silica-enriched, fluoride-mediated syntheses. As STW is composed of approximately 80% double 4-tetrahedral atom rings that are known to be stabilized by inclusion of germanium, addition of varying quantities of germanium to the synthesis gels was explored (34, 35). Following the work of Schmidt et al., reagent molar ratios that lead to the synthesis of STW in the shortest times were: 1 SiO$_2$:x GeO$_2$: 5H$_2$O:0.5 HF:0.5 OSDA 2 at 160° C. (where x is a varying from 0.05 to 0.5) using 10% (w/w) seeds produced from an a chiral diquaternary OSDA with crystal sizes on the order of 1 micron. Aluminum-containing samples were also synthesized (in the presence of Ge) using aluminum isopropoxide. In these syntheses, initial gel Si/Al ratios were maintained above 50, otherwise RTH impurities were observed in the resultant products. Aging the synthesis gels over the course of 24 hours was found to reduce crystallization times. In addition to STW, numerous other phases were produced without significant variation in synthesis conditions, including: LTA, RTH, IWV, CSV, as well as several phases that could not be identified or considered of layered organosilicate materials. Synthesis of these microporous materials is not unexpected, as they have all been shown to be derived from similarly shaped imidazole-based OSDAs under crystallization conditions similar to those reported here. As-made STW crystals obtained utilizing OSDA 2 were analyzed by $^{13}$C CP-MAS solid-state NMR to evaluate whether the OSDA remains intact and directs the formation of STW. FIG. 5 compares the neat OSDA liquid $^{13}$C NMR spectrum with those obtained from analyzing the occluded organic (from solid-state $^{13}$C NMR) and the organic recovered by dissolution of the framework structure (liquid $^{13}$C NMR). Agreement between all spectra indicates that OSDA 2 was occluded intact within the STW framework, and was the structure directing agent. As such, STW was not formed from an organic decomposition product or as a consequence of spontaneous, directed crystallization from the seed crystals. Efforts to perform chiral shift experiments on recovered OSDA 2 collected from dissolution of the STW framework by hydrofluoric acid were not successful due to solubility issues (OSDA 2, chiral shift reagent, and solvent combinations).

Figure 6:
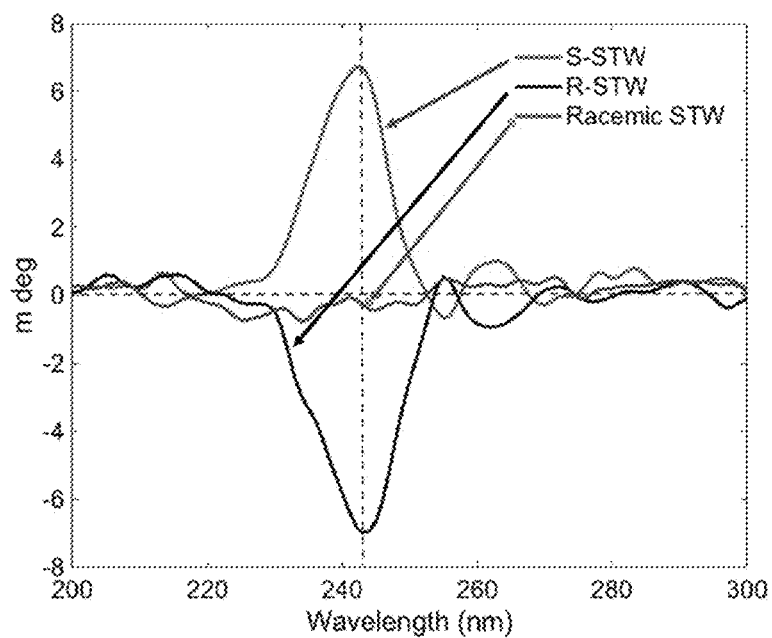
FIG. 6 provides circular dichroism spectra for as-made samples of STW using R-, S-, and racemic OSDA 2. Circular dichrosim reveals that the occluded organic within the STW structure is chiral.

Although it has been speculated that chiral OSDAs (when directed towards a chiral structure) is necessary to lead to an enrichment in the chirality of framework, this concept has never been conclusively proven. In order to do so, the chirality of the organic occluded within the STW structure must be known, as must the chirality of the framework structure for a bulk, polycrystalline sample. Circular dichroism (CD) provides an effective method of accomplishing the former for as-made STW samples. The results for R-, S-, and racemic STW samples are given in FIG. 6. As shown by the data in FIG. 6, the molecules occluded within R- and S-STW absorbed light at 242 nm with equal and opposite polarities. No measured rotation of light was observed for the racemic sample as, statistically, any polarization effects were negated for a sample containing equivalent quantities of chiral crystals. These data collectively demonstrated that OSDA 2 remained chiral and enantiopure within the STW framework. While it may be possible to analyze the structural chirality of a calcined STW structure, no adsorption in the 200-300 nm range was detected from these germanosilicate samples. Incorporation of UV-active heteroatoms beyond those that have been used in this work may provide a pathway for future investigation via CD studies.

In previous reports involving the enrichment of polymorph A in *BEA (that does not guarantee enantioenrichment), characterization of any true structural enrichment of polymorph A has been limited to transmission electron microscopy (TEM) analysis (PXRD analyses are fraught with problems) of the polymorph domains, and demonstration of enantioenrichment by measuring some function, e.g., catalysis or adsorption. A distinct issue with this methodology, however, is that the synthesis of these materials lacks proper controls with regards to the enantiomorphs obtained in the product materials, and therefore it is not possible to perform appropriate analytical and experimental controls to confirm chirality. The methods developed and used here are not subject to these problems. It was possible to control the synthesis of a chiral OSDA (and obtain the R-, S-, and racemic forms thereof) to yield bulk, polycrystalline STW samples comprised of individual crystals of a single chirality. As such, characterization and functional results that are capable of probing the bulk chirality of the two enantioenriched samples of opposing direction must demonstrate enantiomeric excess (ee) that is approximately equal and opposite, with the racemic preparation revealing no ee. The CD experiments for the R-, S-, and racemic STW samples provided the first illustration of how these types of controls can be exploited to derive meaningful conclusions.

Figure 7A:
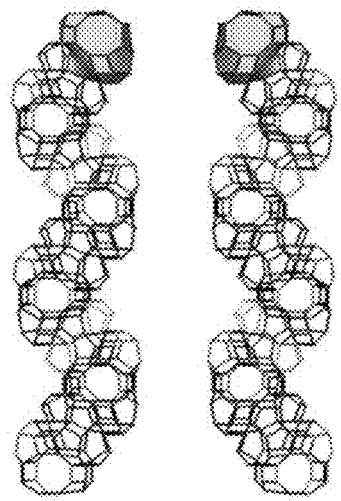
FIG. 7(A) illustrates the enantiomers of the STW framework.
Figure 7B:
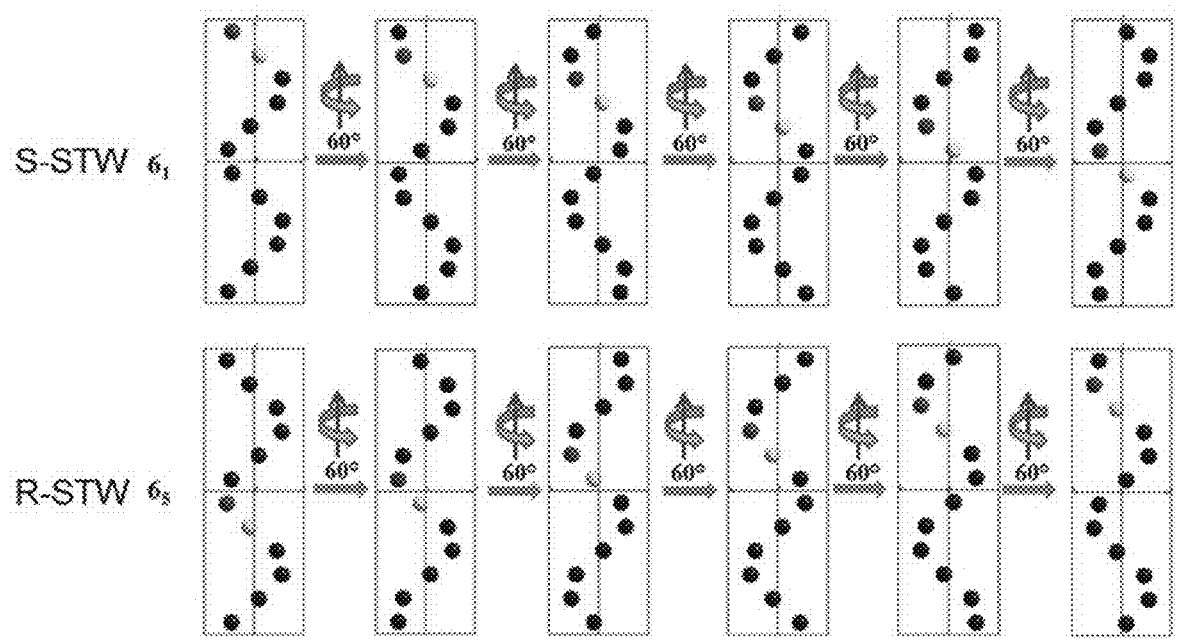
FIG. 7(B) illustrates the principles of the HRTEM analysis scheme used in this work. The two enantiomers have identical 2D projections along any direction, and handedness can be determined by comparing the two projections two projections after tilting the spiral axis.
Figure 7C:
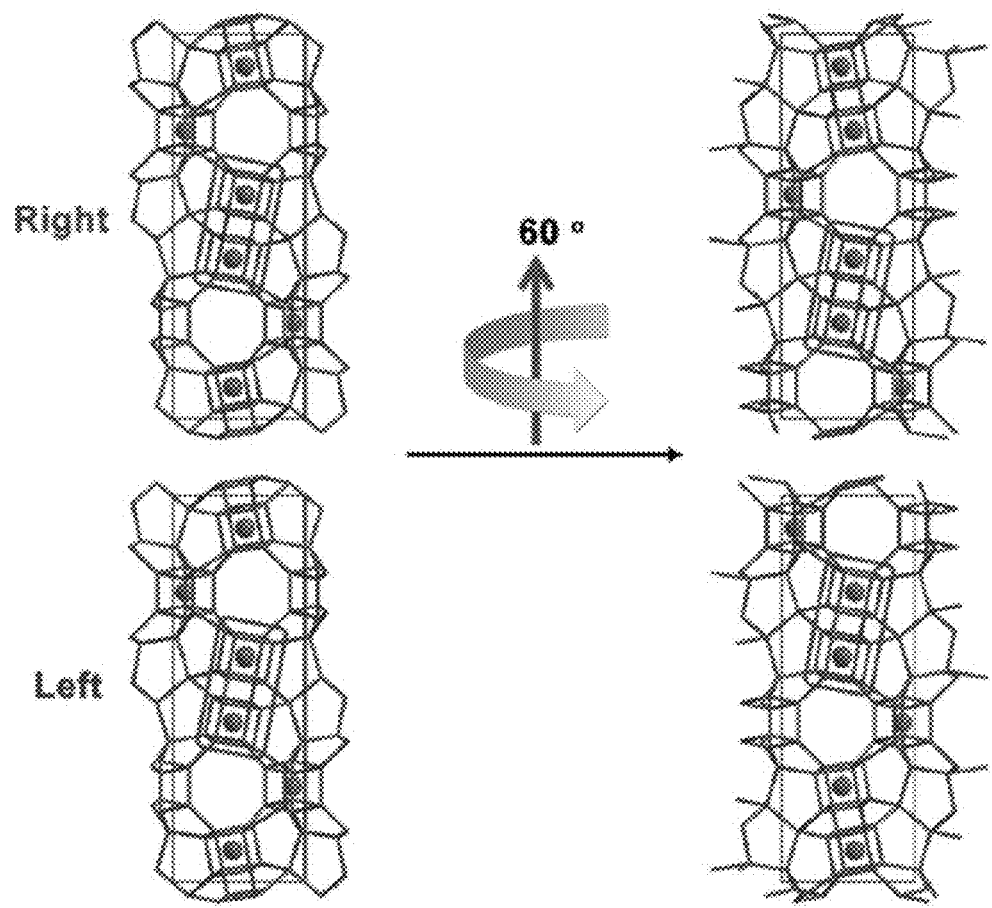
FIG. 7(C) is a schematic representation of a six-fold rotation of STW frameworks with different handedness.
Figure 7D:
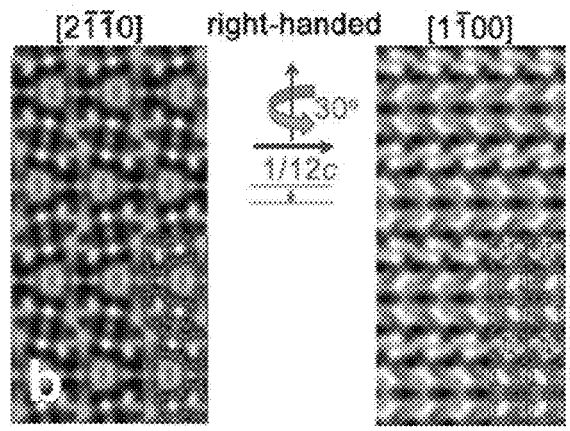
FIGS. 7(D-E) shows simulated HRTEM images of the zeolite with right- and left-handedness, respectively. The atomic structure models, where blue and red balls represent Si and O atoms, were overlaid on top of the simulated images. The shift between two images for right-handed and left-handed STW frameworks has the same length but reverse directions.
Figure 7E:
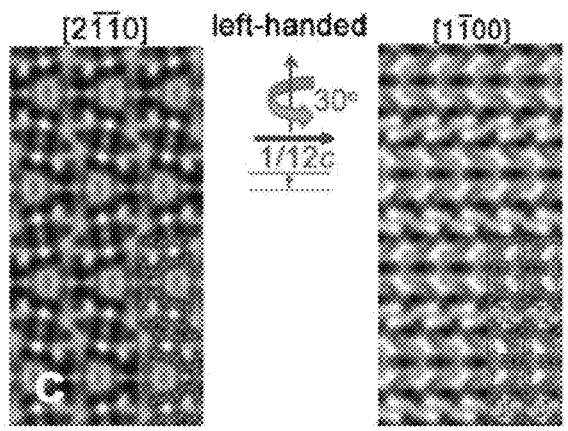
Figure 7F:
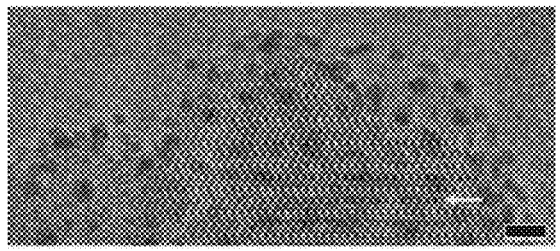
Figure 7G:
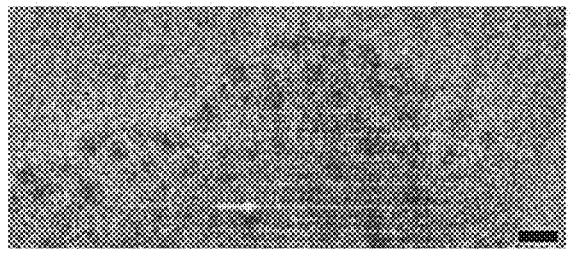
Figure 7H:
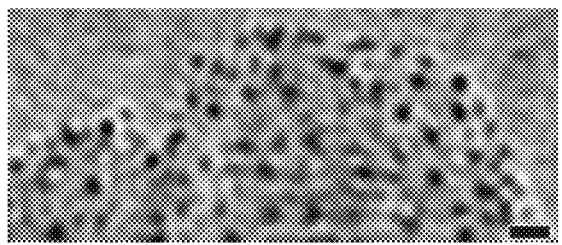
Figure 7I:
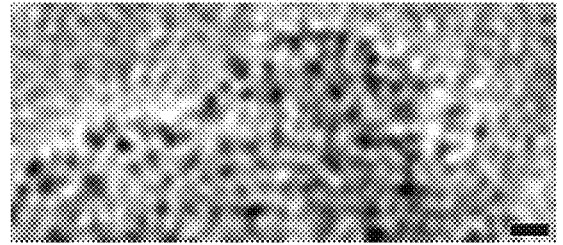
Figure 8A:
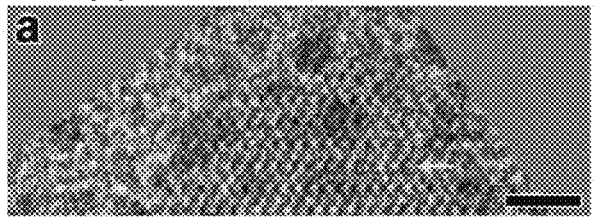
FIGS. 8(A-D) shows a comparison of two HRTEM images with gold nanoparticles as markers.
Figure 8B:
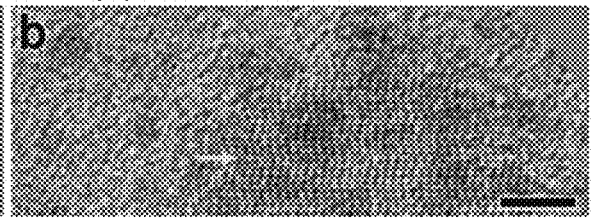
Figure 8C:
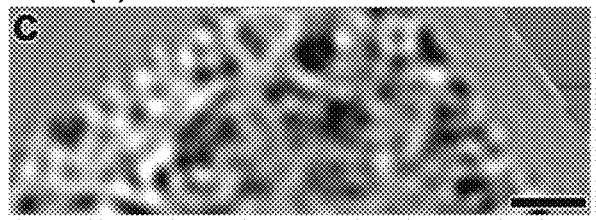
Figure 8D:
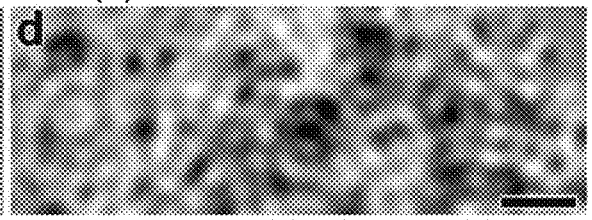
Figure 9A:
FIGS. 9(A-D) show a comparison of two HRTEM images with gold nanoparticles as markers.
Figure 9B:
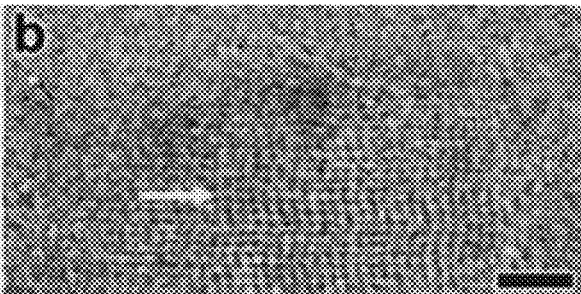
Figure 9C:
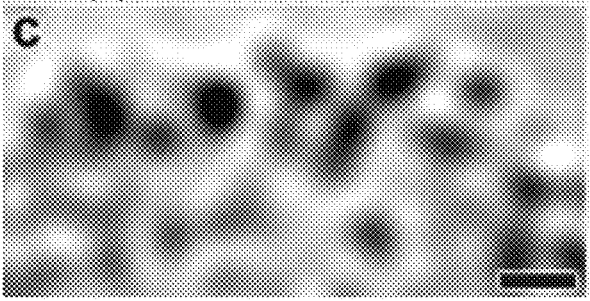
Figure 9D:
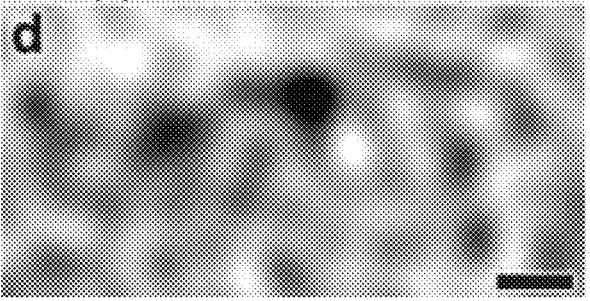
Figure 10A:
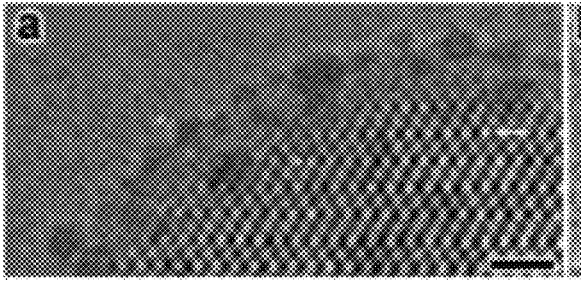
FIGS. 10(A-D) show a comparison of two HRTEM images with gold nanoparticles as markers.
Figure 10B:
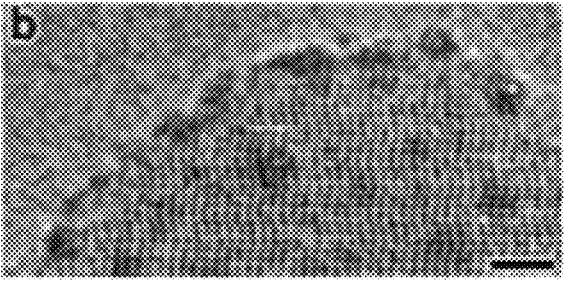
Figure 10C:
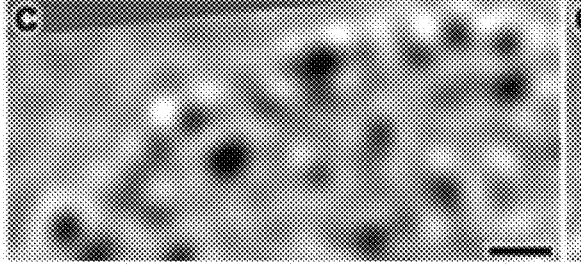
Figure 10D:
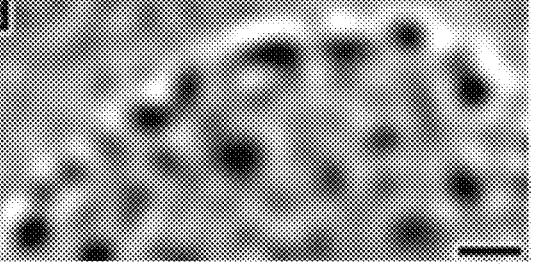
Figure 11:
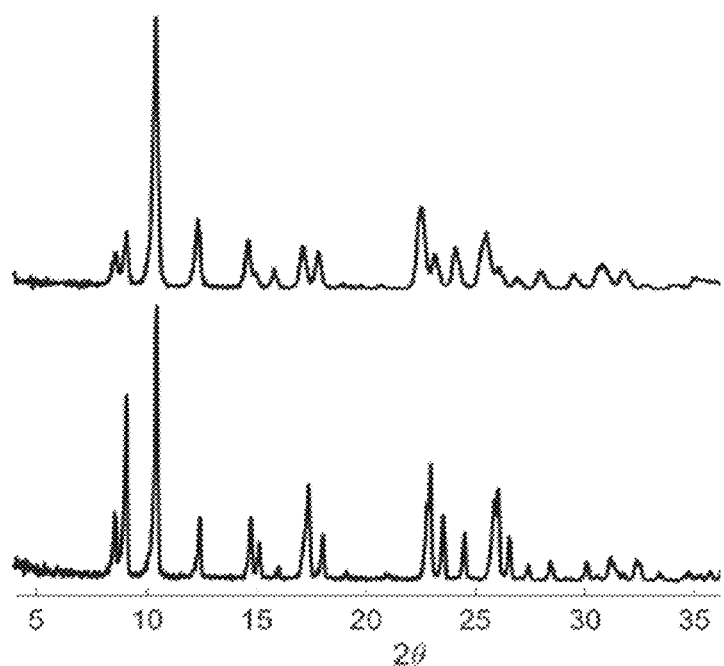
FIG. 11 shows a representative PXRD diffraction patterns for pure-silica racemic STW (lower) and germanosilicate enantrioenriched S-STW (upper). The d-spacings in the enantioenriched sample are shifted as a consequence of the germanium content. Synthesis conditions for the pure silicate-STW: 1 $SiO_2$/0.5 OSDA/0.5 HF/4 MO at 160° C., 7 days. Synthesis conditions for the germanosilicate-STW: 1 $SiO_2$/0.5 $GeO_2$/0.5 OSDA/0.5 HF/4 $H_2O$ at 160° C., 12 days, seeded.

Characterization of the structural chirality of STW was complicated. An examination of the literature yielded few methods for effectively determining this property for siliceous microporous materials beyond the demonstration of enantiomeric excesses derived from reactions or adsorption experiments. Analytical difficulty partially stems from the small crystal sizes (as is the case for STW synthesized with OSDAs used here) that prohibit the use of single crystal XRD. Scanning and high-resolution transmission electron microscopy (SEM and HRTEM, respectively) have proven to be highly advantageous methods for analyzing crystallite morphologies. HRTEM has been used previously to analyze the polymorph domains in *BEA. However, specific chiral space groups (i.e., structural enantiomers) within the detected polymorph A domains were not able to be determined. Fundamentally, the difficulty in unequivocally distinguishing between the space groups of a chiral material using traditional TEM techniques arises from properties inherent to both structural chirality and experimental limitations. Specifically, on a given two-dimensional plane (as is observed in a typical TEM experiment), the structures of the two enantiomers are superimposable and indistinguishable. A method was therefore developed to perform three-dimensional HRTEM experiments in order to effectively characterize chiral space groups. The projection of the STW framework shifts after rotation along the screw axis as schematically illustrated in FIGS. 7(A-C). The rotation direction can be either clockwise (to the right) or counter-clockwise (to the left). A zeolite crystal (that has been deposited with gold nanoparticles (diameter ~5 nm) that serve as reference points with the microporous structure) was first aligned to [2$\bar{1}\bar{1}$0] zone axis and a through-focus series of HRTEM images were taken from a thin area. The crystal was then tilted continuously to the right or to the left by 30° about the screw axis. Upon rotation, the [1$\bar{1}$00] zone axis was observed if the tilting was clockwise. Based on simulated results, the crystal was right-handed if the shift direction was downwards (FIGS. 7D and E). Upon rotation, the [1$\bar{1}$00] or [10$\bar{1}$0] zone axes were observed if the tilting direction was to the right or left, respectively. A series of through-focus images were then taken again along either zone axis. Two images along [2$\bar{1}\bar{1}$0] and [1$\bar{1}$00] were obtained by structure projection reconstructions using the through-focus series of HRTEM images and were aligned based on the positions of gold nanoparticles (FIGS. 7(F-I)) and FIGS. 8-11). By comparing the aligned images from the two zone axes, there was an observable shift between the two projections from which the space group of the crystal could be assigned.

The results collected from using this method to analyze STW crystals selected from bulk, polycrystalline samples synthesized using the R-, S- and racemic versions of 2 are given in Table 3. Out of the six crystals analyzed for both the R- and S-OSDA derived samples, five were determined to possess the $P6_122$ and $P6_522$ space groups, respectively, demonstrating (within this data set) notable enantioenrichment. Moreover, these experimental results were consistent with computational predictions whereby R-OSDA 2 is expected to yield crystals with $P6_122$ space group and, similarly, S-OSDA 2 is anticipated to result in crystals with the $P6_522$ space group (Table 3). Analysis of the racemic sample resulted in an equal number of crystals from each space group, was as expected.

TABLE 3

Summary of the results obtained from rotational HRTEM analysis for STW crystals synthesized from the R-, S- and racemic OSDA 2.

| OSDA Used | No. of Crystals Analyzed | $P6_122$ | $P6_522$ |
|---|---|---|---|
| R-2 | 6 | 5 | 1 |
| S-2 | 6 | 1 | 5 |
| Racemic 2 | 6 | 3 | 3 |

Ideally, for a given sample synthesized using a chiral OSDA, HRTEM analysis would subsequently demonstrate only crystals from the expected space group. However, as shown in Table 3, a crystal from both chiral OSDA derived samples was determined to be from the unexpected space group (e.g., $P6_522$ from the R-OSDA). Possible reasons for incomplete purity include: (1) the crystal of the opposite space group was a seed crystal, (2) there was OSDA degradation that occurred that yielded a racemic portion of the polycrystalline sample, and (3) the inherent nature of the crystallization process does not synthesize an enantiopure, but only an enantioenriched, polycrystalline sample. While currently the number of crystals that have been analyzed was not sufficient to draw a statistically conclusive picture of the bulk chirality of the samples, these HRTEM data (coupled with the distinct differences detected between R- and S-OSDA synthesized materials) are useful to demonstrate, for the first time, enantioenrichment of a bulk, polycrystalline sample of a molecular sieve.

CD and HRTEM characterizations demonstrated that a given enantiomer of OSDA 2 maintains its respective chirality in the occluded state, and is capable of producing an enantioenriched, molecular sieve framework. While there may exist crystallization processes wherein achiral molecules lead to enantioenrichment of product solids, such as by spontaneous chiral symmetry breaking by self-catalyzed crystallization, such systems would not allow for the directed synthesis of specific enantiomers of crystals, as we are able to demonstrate in this work. Thus, it follows that the initial hypothesis by Lobo and Davis that any bulk, polycrystalline sample having enantioenrichment (not obtained solely from chiral seeds) must be derived from a chiral OSDA with a particular set of properties, appears valid. Additionally, this synthesis methodology ensures that all forms (R-, S-, and racemic) are attainable, thus allowing for appropriate controls to be performed.

Example 3.1: Synthesis of Germanosilicate STW Using OSDA 2

STW was synthesized by methods adopted from those previously reported.

Conditions under which germanosilicate STW was found to crystallize most successfully were found to stem from starting gel compositions of 1 $SiO_2$:0.5 $GeO_2$:4 $H_2O$:0.5 HF:0.5 OSDA 2 (enantiopure or racemic). For a typical reaction, the desired quantity of germanium oxide and OSDA was mixed, and the solids were allowed to homogenize over the period of an hour. Next, a quantity of tetraethylorthosilicate was added, and the mixture was allowed to hydrolyze over the period of 12 hours. Ethanol produced as a consequence of the hydrolysis was then allowed to evaporate at room temperature, in addition to a quantity of water to attain the desired $H_2O/SiO_2$ ratio. After allowing the gel to age at its final composition for 24 hours, as-synthesized, racemic, pure-silica STW (particle size ~1 μm) was added as seed material (10% (w/w) of $SiO_2$ in the gel) to this gel and mixed. The final gel was transferred to a Teflon-lined stainless steel autoclave and heated at 433 K in a rotating oven until crystallization products formed. The recovered solids were centrifuged, washed extensively with water and acetone, then dried in an oven at 343 K. To remove the organic occluded within the structure, the sample was placed into a tube furnace maintained at 423 K through which ozone was passed (125 mL/minute of 6.7% ozone in 02). For materials with less germanium content, the solids were calcined in flowing air (100 mL min-1, Airgas, breathing grade) at 853 K (after a ramp of 1 K min-1) for 6 hours after maintaining 423 K for 3 hours.

Example 3.2: Synthesis of Aluminogermanosilicate STW Using OSDA 2

Aluminogermanosilicate STW was synthesized using a similar procedure outlined vide supra for germanosilicate STW. However, to the initial combination of germanium oxide and OSDA, a quantity of aluminum isopropoxide was added and allowed to homogenize and hydrolyze. The final gel composition of samples used in catalytic function testing were: 1 $SiO_2$: 0.5 $GeO_2$: 0.01 $Al_2O_3$: 5 $H_2O$: 0.5 HF: 0.5 Compound OSDA 2 (enantiopure or racemic). Similar procedures were also followed to remove the organic content

TABLE 4

Summary of STW syntheses using racemic 2.

| Si/Ge | Si/Al | $H_2O$/$TO_2$ | Temp. (° C.) | Seeds | Time | Results |
|---|---|---|---|---|---|---|
| 2 | ∞ | 5 | 175 | None | 6 | STW + dense |
| 9 | ∞ | 5 | 175 | None | 16 | STW + U |
| ∞ | ∞ | 5 | 175 | None | 23 | BEA + dense |
| 2 | ∞ | <3 | 175 | None | 4 | IWV |
| 9 | ∞ | <3 | 175 | None | 4 | IWV |
| ∞ | ∞ | <3 | 175 | None | 20 | Si-RTH layered |
| 2 | ∞ | 4 | 175 | None | 4 | IWV + STW |
| 2 | ∞ | 5 | 175 | None | 4 | IWV + STW |
| 2 | ∞ | 7 | 175 | None | 4 | IWV + STW |
| 10 | ∞ | 4 | 175 | None | 4 | IWV + CIT-7 |
| 10 | ∞ | 5 | 175 | None | 4 | IWV |
| 10 | ∞ | 7 | 175 | None | 4 | IWV |
| 2 | ∞ | 5 | 175 | Si-STW | 4 | STW |
| 10 | ∞ | 5 | 175 | Si-STW | 4 | IWV + STW |
| 2 | ∞ | 5 | 160 | Si-STW | 3 | STW + U |
| ∞ | ∞ | 4 | 175 | None | 13 | Si-RTH layered |
| ∞ | ∞ | 5 | 175 | None | 13 | Si-RTH layered |
| ∞ | ∞ | 7 | 175 | None | 36 | Dense |
| 10 | ∞ | 5 | 160 | Si-STW | 8 | STW |
| ∞ | ∞ | 5 | 160 | Si-STW | 11 | Si-RTH layered |
| ∞ | ∞ | 5 | 175 | Si-STW | 11 | Si-RTH layered |
| 10 | ∞ | 5 | 160 | Si-STW | 23 | STW |
| 15 | ∞ | 5 | 160 | Si-STW | 16 | STW |
| 20 | ∞ | 5 | 160 | Si-STW | 16 | MTW |
| 20 | ∞ | 5 | 160 | Si-STW | 16 | MTW |
| 10 | ∞ | 5 | 160 | Si-STW | 13 | STW + IWV |
| 15 | ∞ | 5 | 160 | Si-STW | 13 | STW + IWV |
| 20 | ∞ | 5 | 160 | Si-STW | 7 | STW |
| 20 | ∞ | 5 | 160 | Si-STW | 18 | STW + IWV |
| 20 | ∞ | 5 | 160 | Si-STW | 18 | STW + IWV |
| 30 | ∞ | 5 | 160 | Si-STW | 7 | IWV |
| 30 | ∞ | 5 | 160 | Si-STW | 7 | IWV |
| 50 | ∞ | 5 | 160 | Si-STW | 18 | STW + IWV |
| 50 | ∞ | 5 | 160 | Si-STW | 18 | IWV |
| 10 | ∞ | 4 | 160 | Si-STW | 20 | STW |
| 10 | ∞ | 7 | 160 | Si-STW | 5 | IWV + STW |
| 10 | ∞ | 7 | 160 | Si-STW | 5 | IWV + STW |
| 20 | ∞ | 4 | 160 | Si-STW | 20 | STW |
| 20 | ∞ | 7 | 160 | Si-STW | 5 | IWV + STW |
| 20 | ∞ | 10 | 160 | Si-STW | 5 | IWV |
| 30 | ∞ | 4 | 160 | Si-STW | 20 | STW + amph |
| 30 | ∞ | 7 | 160 | Si-STW | 12 | IWV |
| 30 | ∞ | 10 | 160 | Si-STW | 20 | IWV |
| ∞ | ∞ | 4 | 160 | Si-STW | 37 | STW + layered[1] |
| ∞ | ∞ | 4 | 160 | Si-STW | 37 | STW[2] |
| ∞ | ∞ | 4 | 160 | Si-STW | 20 | STW[3] |
| ∞ | ∞ | 2 | 160 | None | 14 | MTW + STW |
| ∞ | ∞ | 2 | 160 | None | 14 | MTW + STW |
| ∞ | ∞ | 3 | 160 | None | 14 | MTW + STW |
| ∞ | ∞ | 3 | 160 | None | 19 | MTW + STW |
| 4 | ∞ | 5 | 160 | None | 7 | LTA |
| 8 | ∞ | 5 | 160 | None | 7 | LTA |
| 20 | ∞ | 5 | 160 | Si-STW | 7 | LTA + U |
| 100 | ∞ | 5 | 160 | Si-STW | 30 | A |
| 20 | ∞ | 5 | 160 | Si-STW | 8 | U |
| 8 | ∞ | 4 | 160 | Si-STW | 10 | U |
| 10 | ∞ | 4 | 160 | Si-STW | 24 | U |
| 12 | ∞ | 4 | 160 | Si-STW | 10 | U + A |
| 14 | ∞ | 4 | 160 | Si-STW | 10 | U + A |
| 10 | ∞ | 4 | 160 | Si-STW | 13 | IWV + LTA |
| 2 | ∞ | 5 | 160 | Si-STW | 10 | STW |
| 2 | ∞ | 5 | 160 | Si-STW | 10 | LTA + A |
| 4 | ∞ | 5 | 160 | Si-STW | 10 | LTA + U |
| 4 | ∞ | 5 | 160 | Si-STW | 10 | LTA + U |
| 4 | ∞ | 5 | 160 | Si-STW | 13 | STW + U |
| 4 | ∞ | 5 | 160 | Si-STW | 13 | STW + U |
| 6 | ∞ | 5 | 160 | Si-STW | 13 | STW + U |
| 6 | ∞ | 5 | 160 | Si-STW | 13 | STW + U |
| 8 | ∞ | 5 | 160 | Si-STW | 29 | LTA + U |
| 8 | ∞ | 5 | 160 | Si-STW | 29 | LTA + U |
| 10 | ∞ | 5 | 160 | Si-STW | 29 | LTA + U |
| 10 | ∞ | 5 | 160 | Si-STW | 29 | LTA + U |
| 8 | ∞ | 5 | 160 | Si-STW | 11 | LTA |
| 8 | ∞ | 5 | 160 | Si-STW | 11 | LTA |
| 2 | 100 | 5 | 160 | Si-STW | 13 | STW + LTA |
| 2 | 100 | 5 | 160 | Si-STW | 13 | STW |
| 12 | ∞ | 5 | 160 | Si-STW | 11 | LTA |
| 12 | ∞ | 5 | 160 | Si-STW | 11 | LTA |

A = amorphous, U = unknown, synthesis time is reported in days.
[1]A mixture of 2 and pentamethylimdazolium (P) in a ratio of 2/P = 9 was used as the OSDA.
[2]2/P = 4,
[3]2/P = 2.3.

TABLE 5

Summary of STW syntheses using R-2.

| Si/Ge | Si/Al | $H_2O$/$TO_2$ | Temp, ° C. | Seeds | Time | Results |
|---|---|---|---|---|---|---|
| 20 | ∞ | 4 | 160 | Si-STW | 16 | STW |
| 20 | ∞ | 4 | 160 | Si-STW | 16 | RTH |
| 20 | ∞ | 4 | 160 | Si-STW | 16 | RTH + IWV + STW |
| 20 | ∞ | 4 | 160 | Si-STW | 16 | RTH |
| 30 | ∞ | 4 | 160 | Si-STW | 16 | RTH |
| 20 | 100 * | 4 | 160 | Si-STW | 19 | STW |
| 20 | 100 * | 4 | 160 | Si-STW | 19 | STW |
| 2 | 100 | 4 | 160 | Si-STW | 10 | STW |
| 2 | 100 | 4 | 160 | Si-STW | 10 | STW + LTA |
| 2 | 100 | 4 | 160 | Si-STW | 10 | STW + LTA + U |
| 2 | 100 | 4 | 160 | Si-STW | 10 | STW + LTA |

A = amorphous,
U = unknown,
synthesis time is reported in days (* = Si/Ti)

TABLE 6

Summary of STW syntheses using S-2.

| Si/Ge | Si/Al | $H_2O$/$TO_2$ | Temp. (° C.) | Seeds | Time | Results |
|---|---|---|---|---|---|---|
| 20 | ∞ | 5 | 160 | None | 10 | IWV + STW |
| 20 | ∞ | 5 | 160 | Si-STW | 5 | IWV + STW |
| 5 | ∞ | 5 | 160 | None | 5 | STW + tiny IWV |
| 5 | ∞ | 5 | 175 | Si-STW | 5 | IWV + STW |
| ∞ | ∞ | 5 | 160 | Si-STW | 8 | MTW + STW |
| ∞ | ∞ | 5 | 160 | None | 8 | MTW + STW |
| 20 | ∞ | 4 | 160 | Si-STW | 13 | STW |
| 20 | ∞ | 4 | 160 | Si-STW | 13 | STW |
| 20 | ∞ | 4 | 160 | Si-STW | 25 | A |
| 20 | ∞ | 4 | 160 | Si-STW | 25 | A |
| 10 | ∞ | 4 | 160 | Si-STW | 24 | LTA + U |
| 10 | ∞ | 4 | 160 | Si-STW | 24 | LTA + U |
| 2 | ∞ | 5 | 160 | Si-STW | 12 | STW + LTA |

TABLE 6-continued

Summary of STW syntheses using S-2.

| Si/Ge | Si/Al | H$_2$O/ TO$_2$ | Temp. (° C.) | Seeds | Time | Results |
|---|---|---|---|---|---|---|
| 2 | ∞ | 5 | 160 | Si-STW | 12 | STW + LTA |
| 2 | ∞ | 5 | 160 | Si-STW | 12 | STW |
| 2 | ∞ | 5 | 160 | None | 12 | STW + LTA |
| 2 | ∞ | 5 | 160 | None | 12 | LTA + U |
| 2 | 100 | 5 | 160 | Si-STW | 13 | STW |
| 2 | 100 | 5 | 160 | Si-STW | 12 | STW |
| 2 | 100 | 5 | 160 | Si-STW | 13 | STW + LTA |
| 2 | 100 | 5 | 160 | Si-STW | 20 | STW + LTA |

A = amorphous, U = unknown, synthesis time is reported in days.

Figure 12:
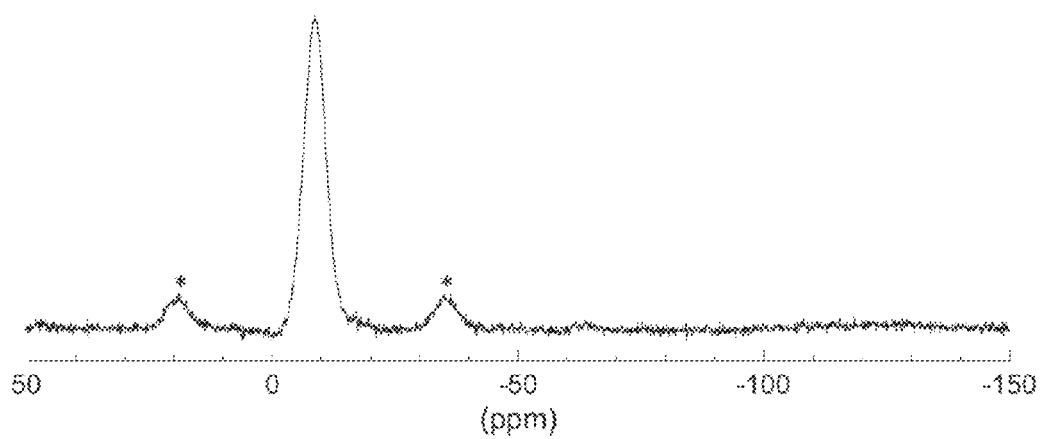
FIG. 12 shows a representative $^{19}F$ NMR spectrum for an enantioenriched S-STW germanosilicate sample. Peaks labeled with a * correspond to spinning side bands.
Figure 13:
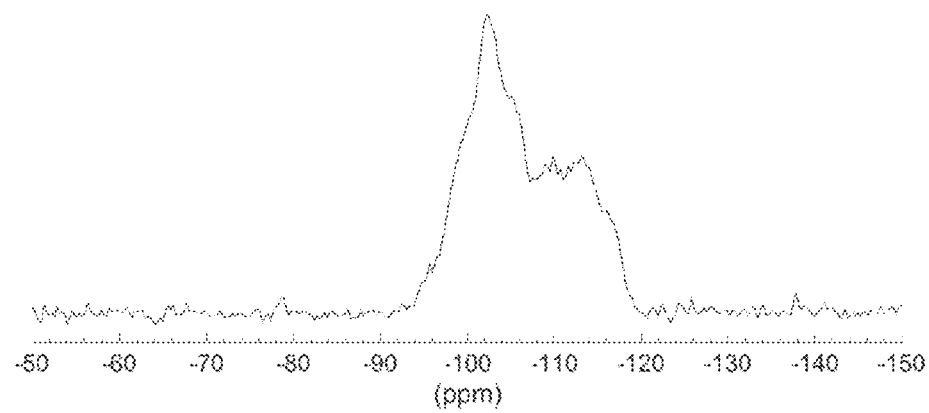
FIG. 13 shows a representative $^{29}Si$ NMR spectrum for an enantioenriched S-STW germanosilicate sample.
Figure 14:
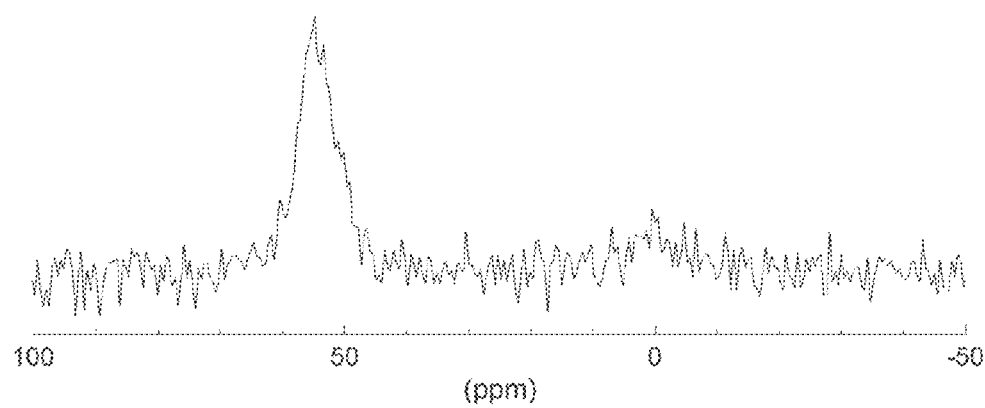
FIG. 14 shows a representative $^{27}Al$ NMR spectrum for an enantioenriched S-STW aluminogermanosilicate sample.

$^{13}$C, $^{19}$F, $^{27}$Al and $^{29}$Si solid-state NMR were performed using a Bruker DSX-500 spectrometer (11.7 T) and a Bruker 4 mm MAS probe. The spectral operating frequencies were 500.2 MHz, 125.721 MHz, 130.287 MHz and 99.325 MHz for $^1$H, $^{13}$C, $^{19}$F, $^{27}$Al and $^{29}$Si nuclei, respectively. Spectra were referenced to external standards as follows: tetramethylsilane (TMS) for 1H and $^{29}$Si, CFCl$_3$ for $^{19}$F, adamantane for $^{13}$C as a secondary external standard relative to tetramethylsilane and 1.0 M Al(NO$_3$)$_3$ aqueous solution for $^{27}$Al. Samples were spun at 14 kHz for $^1$H and $^{27}$Al MAS NMR and 8 kHz for $^{13}$C and $^{29}$Si MAS and CPMAS NMR experiments. $^{19}$F MAS NMR were collected at both 13 and 15 kHz to assign spinning sidebands. For detection of $^{27}$Al signal, a short 0.5 μs-π/18 pulse was used before FID was recorded in order to make quantitative comparison among resonances. See FIGS. 12-14 for representative NMRs.

Figure 15:
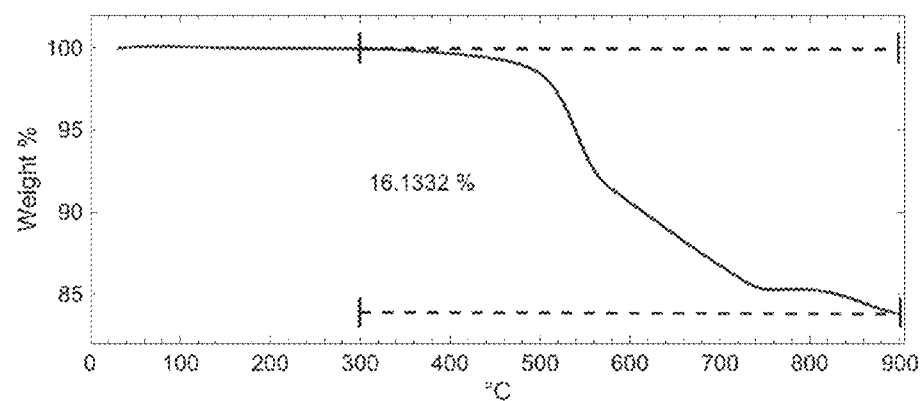
FIG. 15 shows a representative thermogravimetric analysis (TGA) profile for enantioenriched germanosilicate S-STW.

Thermogravimetric analysis (TGA) measurements were performed on Perkin Elmer STA 6000. Samples (0.01-0.06 g) were placed in an alumina crucible and heated at 1 K/min in a flowing stream (0.667 cm$^3$/s) of air. See FIG. 15 for a representative TGA profile for enantioenriched germanosilicate S-STW.

Figure 16:
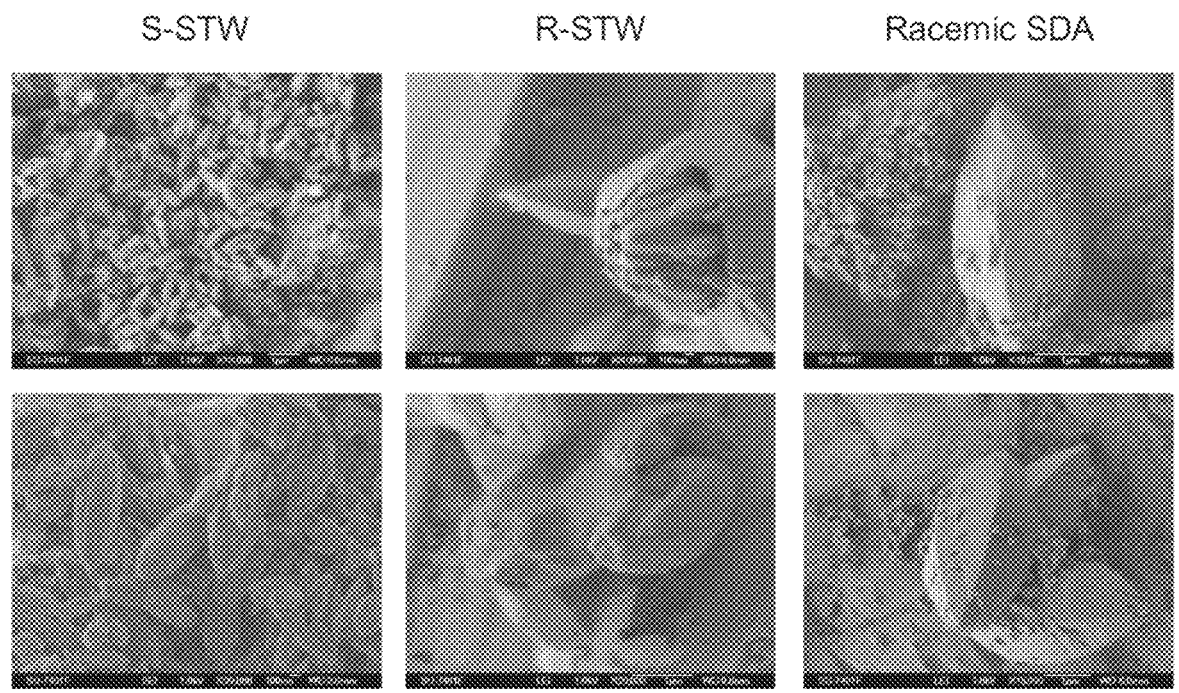
FIG. 16 shows selected SEM images for the R-, S-, and racemic STW.

Scanning electron micrographs (SEM) were recorded on a Hitachi S-570 instrument. EDS spectra were acquired with an Oxford X-Max SDD X-ray Energy Dispersive Spectrometer system on a ZEISS 1550 VP FESEM, equipped with in-lens SE. See FIG. 16 for select images of SEM images for S-, R- and racemic STW.

TABLE 7

Representative energy-dispersive X-Ray spectroscopy results for products obtained using S-2 in germanosilicate and aluminogermanosilicate synthesis gels

| Starting Gel | Si/Ge | Si/Al |
|---|---|---|
| Germanosilicate, Si/Ge = 2 | 0.806 ± 0.047 | — |
| Aluminogermanosilicate, Si/Ge = 2, Si/Al = 100 | 0.861 ± 0.045 | 30.15 ± 11.96 |

Example 4: Catalysis with Enantioenriched STW

Example 4.1: Reaction and Analysis Procedures

After addition of 20 mg of Al-containing STW (Si/Al=30: 1:10), 20 mmol of epoxide substrate, and 5 g of methanol (with pre-dissolved naphthalene as internal standard) were added to a 10 mL thick-walled glass reactor (VWR) containing a stir bar. The reactor was crimp-sealed and placed in a temperature-controlled oil bath at the desired reaction temperature. At predetermined times, aliquots of (~100 μL) were extracted and analyzed.

Quantitative GC/FID analysis was performed on an Agilent 7890B GC system equipped with a flame ionization detector and an Agilent Cyclosil-B column. Liquid $^1$H and $^{13}$C NMR spectra were recorded with a Varian INOVA 500 MHz spectrometer equipped with an auto-x pfg broad band probe. All liquid NMR analysis was performed in deuterated methanol.

Example 4.2: Results

The chirality in STW is defined over the specific distance within the helical STW pore structure (FIG. 1). As a consequence, adsorption and catalysis that show ee's will involve molecules that are of sufficient size to effectively experience the chirality of the structure, yet still be able to pass through the limited size of the pores. As such, we expect that any measured ee's will be greatly dependent on the selection of molecules used to test for a function. Moreover, the external surfaces of the crystallites may behave nonspecifically, resulting in diminishing ee's.

Figure 17A:
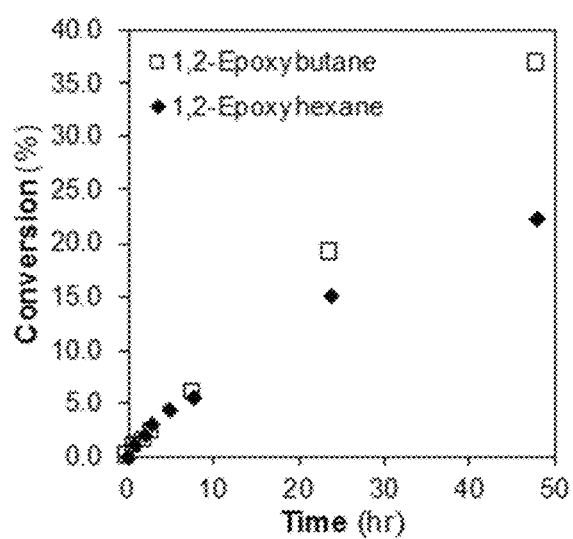
FIGS. 17(A-B) show kinetic results of the catalytic epoxide ring-opening reactions of 2-epoxybutane and 2-epoxyhexane using racemic STW aluminosilicate catalysts.
Figure 17B:
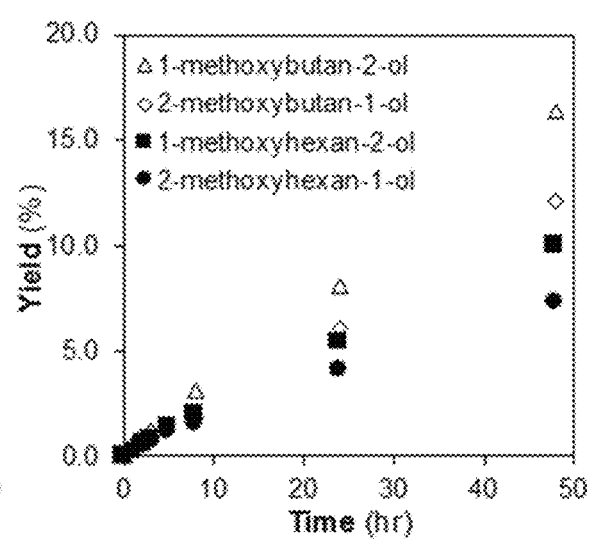

In initial experiments, racemic Al-containing STW (obtained using pentamethylimidazolium cations as OSDA) was used to examine the viability of the epoxide ring-opening. Two distinct reaction mechanisms are possible (see scheme in Table 8), both of which are known to occur in Al-containing molecular sieves. Shorter chained 1,2-epoxybutane achieved higher conversions (37%) than did 1,2-epoxyhexane (22%), likely due to steric and shape-selective results. For both reactions, the production of the least-substituted product (1-alkoxy-2-alcohol) was favored. See FIGS. 17(A-B).

To examine whether the enantioenriched STW samples are capable of performing enantioselective functions, catalysis and adsorption experiments were conducted. Epoxide ring-opening reactions on 1,2-epoxyalkanes were selected for catalysis, as they have been shown to take place within molecular sieves at relatively low temperatures. Such low-temperature probe reactions are particularly desirable because symmetry-breaking dispersive interactions with the catalyst surface are expected to be relatively larger contributors to the transition state free energies compared to high-temperature scenarios. The results from these reactions are reported in Table 8. For epoxides shorter than C8, enantiomeric excesses that are not significantly different than experimental error are observed. However, as the chain length is further extended (to approximate the size of OSDA 2) the magnitude of the ee's become significantly different from experimental error. Of importance is that results that approximately the same magnitude of the ee's are obtained, but in opposite directions, from the R-STW and the S-STW, as should be. Trans-stilbene oxide was also used as a substrate and minimal ring opening was observed. As this substrate is too large to enter the pores of STW, this control experiment demonstrates that the rate of reaction outside the pore structure (i.e., on the surface of the crystals) is negligible, and that any measured ee's do not occur as a consequence of surface or solvent effects.

TABLE 8

Summary of enantiomeric excess from the ring opening of 1,2-epoxyalkanes with methanol using aluminum-containing racemic, R-, and S-STW as catalysts. Product a is the less substituted 1-methoxyalkan-2-ol product, while product b is the more substituted 2-methoxyalkan-1-ol product. The reaction solutions were analyzed after 48 hours.

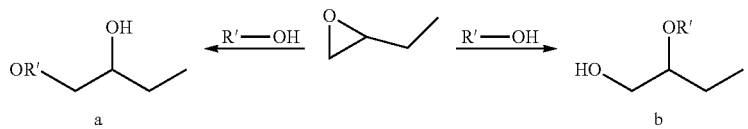

| | Enantiomeric Excess of Products Using Enantioenriched STW | | | | | |
|---|---|---|---|---|---|---|
| | R-STW | | Racemic STW | | S-STW | |
| Substrate | a, % | b, % | a, % | b, % | a, % | b, % |
| 1,2-epoxybutane | −0.14 | 2.31 | 0.05 | 0.06 | 0.02 | −2.26 |
| 1,2-epoxyhexane | 1.29 | 2.83 | 0.20 | −0.92 | −1.96 | −3.46 |
| 1,2-epoxyoctane | 4.13 | 9.85 | 1.14 | −0.86 | −4.41 | −10.65 |

Example 5: Adsorption with Enantio-Enriched STW

Example 5.1: Adsorption Procedures

Adsorption isotherms were collected on a Quantachrome Autosorb iQ with varying methods depending upon the adsorbate.

Example 5.2: Results

Figure 18A:
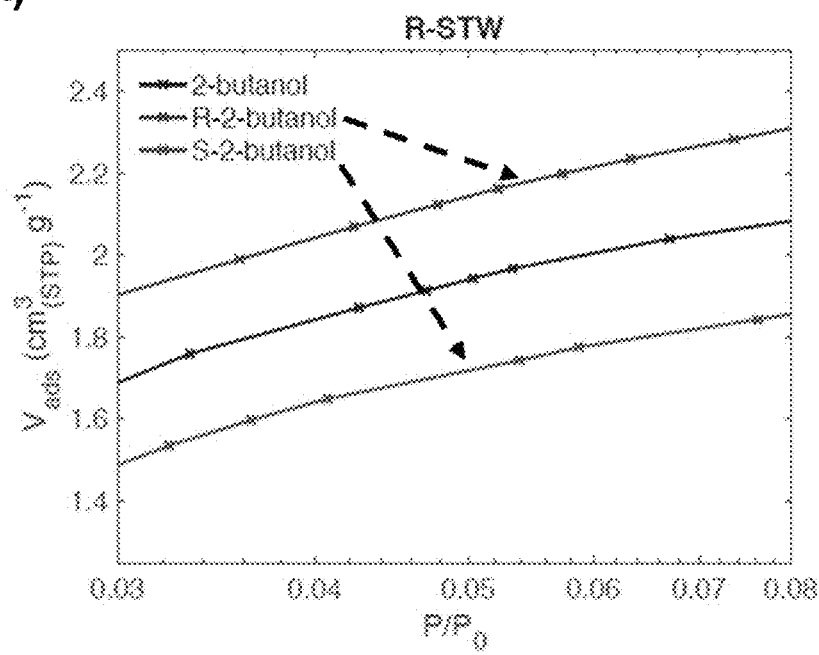
FIGS. 18(A-B) show 2-butanol adsorption isotherms at 278 K for germanosilicate R- and S-STW. Differences in uptake are a result of variations in sample crystallinity.
Figure 18B:
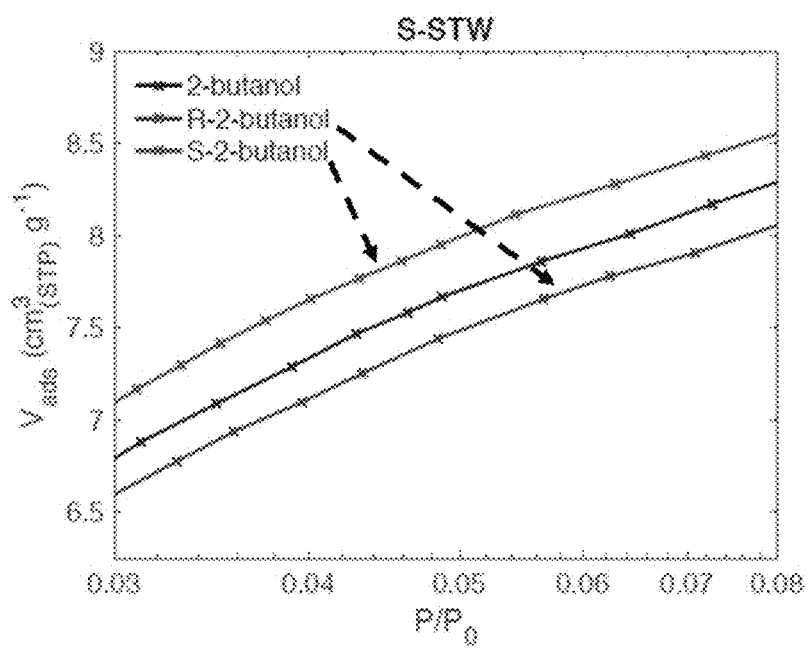

Vaporsorption experiments were performed utilizing the pure R-, S- and racemic solutions of 2-butanol. Previous computational studies suggested that germanosilicate STW is capable of selectively adsorbing R- and S-glycidol into the helices of the respective enantiomers of the framework, with increasing discrimination between enantiomers from a racemic mixture with decreasing system temperatures. Experiments were therefore performed at 278 K (which allows for a vapor pressure great enough to collect sufficient adsorption data). FIGS. 18(A-B) illustrate the adsorption isotherms obtained for R-, S- and racemic 2-butanol in germanosilicate R- and S-STW. For R-STW, R-2-butanol was selectively adsorbed relative to S-2-butanol. The racemic 2-butanol isotherm lay at the approximate average of the isotherms from the enantiomerically enriched sample 2-butanol isotherms. An equivalent, but inverse result was observed from S-STW.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

Each patent, patent application, and publication cited or described in this document is hereby incorporated herein by reference, each in its entirety, for all purposes, or at least for the teachings in the context in which it was raised.

What is claimed is:

1. An enantiomerically enriched powder comprising two enantiomers of a chiral crystalline microporous solid, the chiral crystalline microporous solid having an STW topology and comprising:
   (a) an oxide of silicon; and optionally
   (b) one or more oxides of aluminum, boron, cerium, gallium, germanium, hafnium, iron, tin, titanium, indium, vanadium, zirconium, or a combination thereof,
   wherein
   the enantiomerically enriched powder exhibits an enantiomeric excess of one enantiomer of the chiral crystalline microporous solid over the other enantiomer of the chiral crystalline microporous solid of at least 10%.

2. The enantiomerically enriched powder of claim 1, wherein the crystalline microporous solid is a pure silicate, an aluminosilicate, a borosilicate, a germanosilicate, a titanosilicate, a germanoaluminosilicate, or a germanotitanosilicate.

3. The enantiomerically enriched powder of claim 1, wherein the crystalline microporous solid further comprises a chiral Organic Structure Directing Agent (OSDA) occluded within pores of the crystalline microporous solid, as determined by Circular Dichroism Analysis, the chiral OSDA comprising a structure having a linked pair of imidazolium cations of a structure:

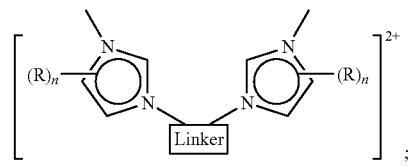

wherein Linker is a 3, 4, 5, or 6-membered ring chiral linking group or an alicyclic four-carbon chiral linking group; and R is independently methyl or ethyl; and n is independently 0, 1, 2, or 3.

4. The enantiomerically enriched powder of claim 3, wherein Linker comprises a chirally substituted cyclopropane, aziridine, epoxide, cyclobutane, cyclopentane, cyclohexane, tetrahydrofuran, pyrrolidine, or tetrahydrothiophene.

5. The enantiomerically enriched powder of claim 3, wherein Linker comprises a structure:
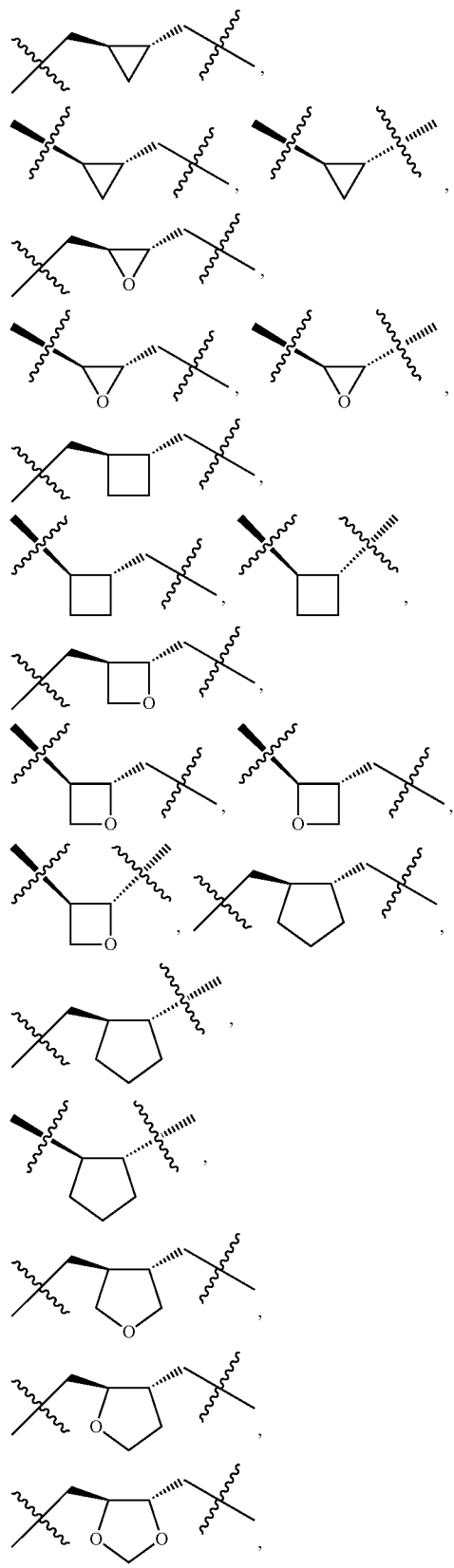
-continued
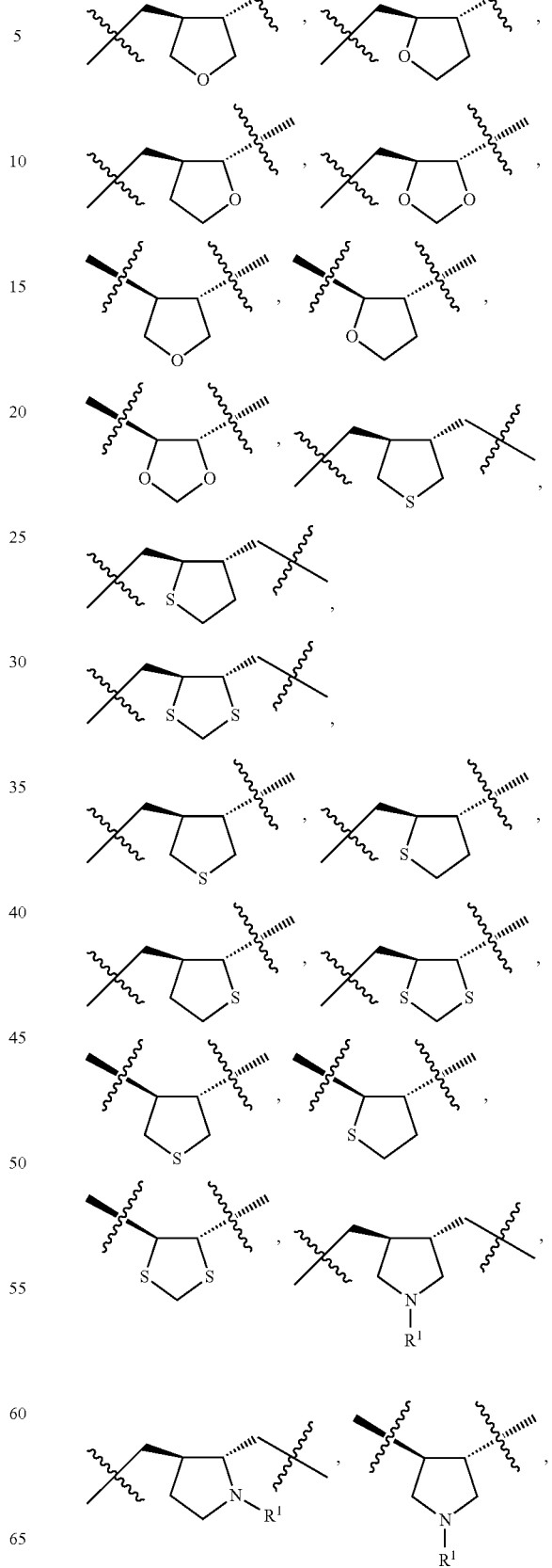

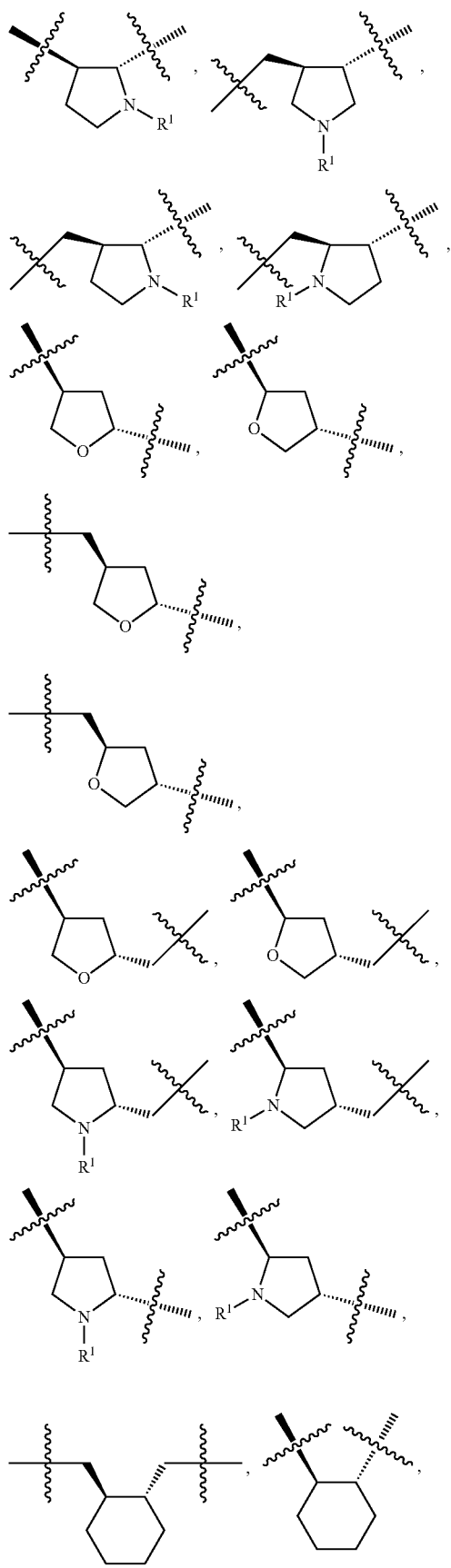
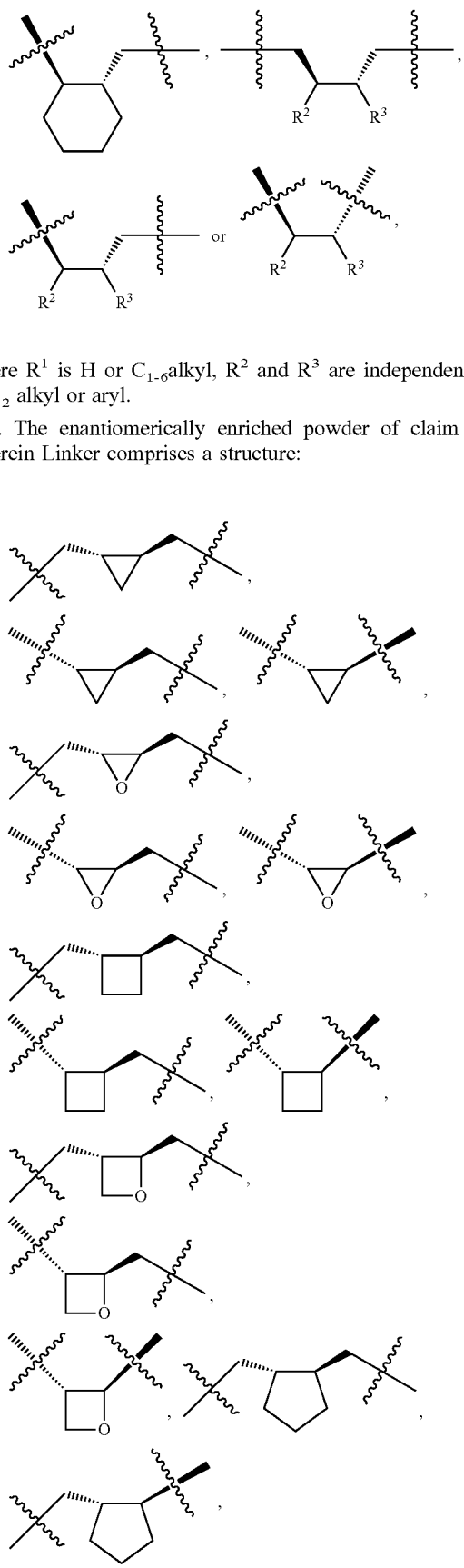
where $R^1$ is H or $C_{1-6}$alkyl, $R^2$ and $R^3$ are independently $C_{1-12}$ alkyl or aryl.
6. The enantiomerically enriched powder of claim 3, wherein Linker comprises a structure:

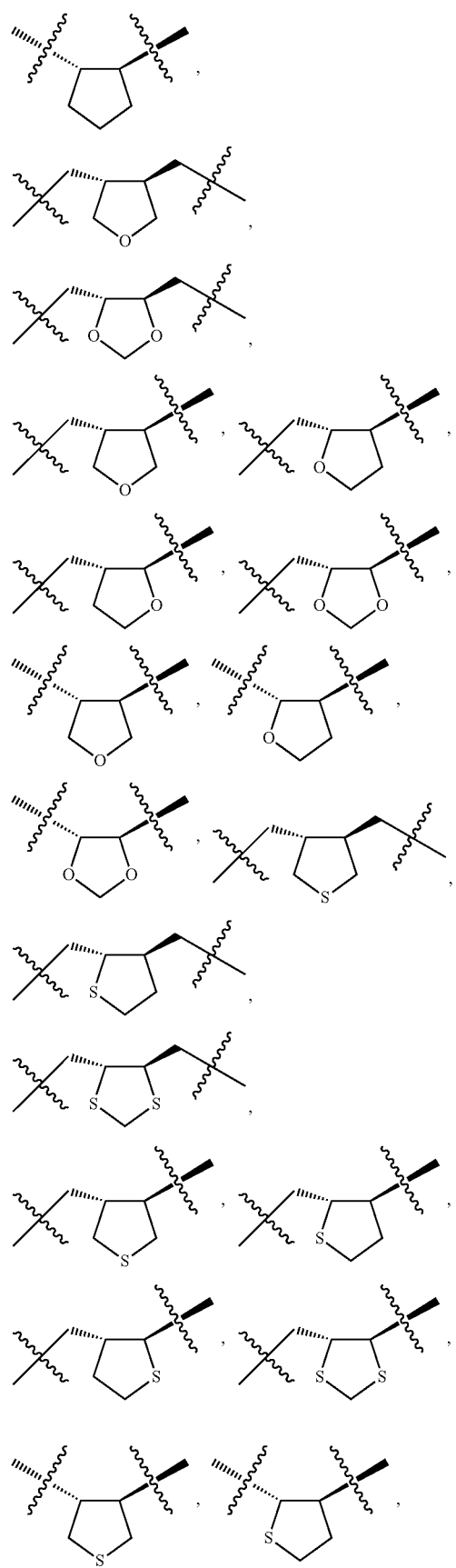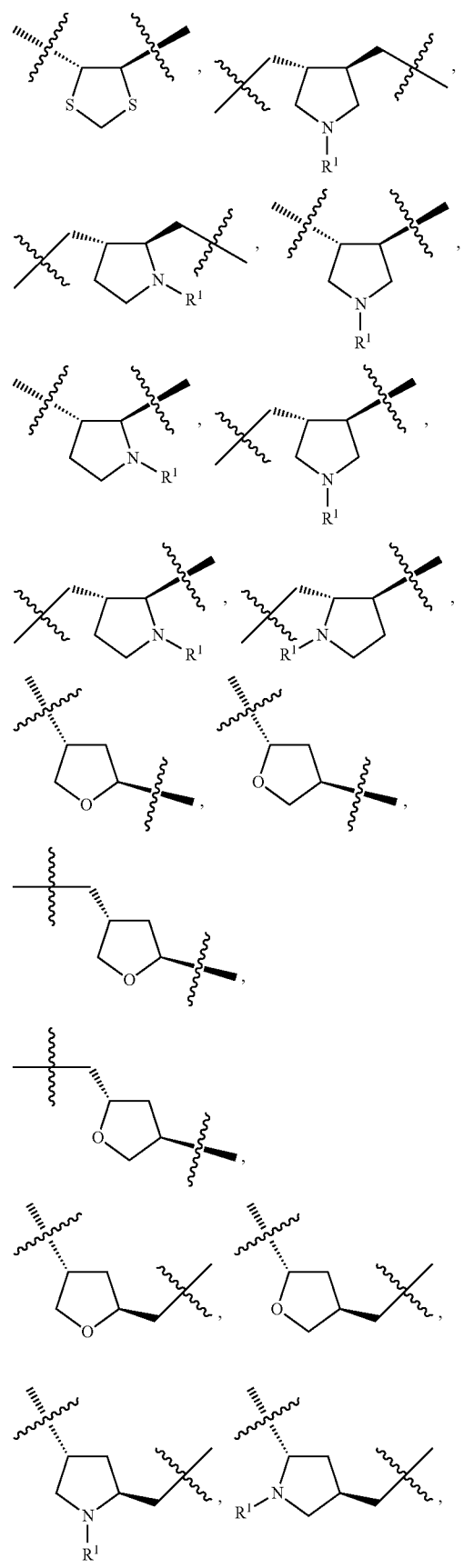

(d) a linked pair of quaternary imidazolium cations of a structure:

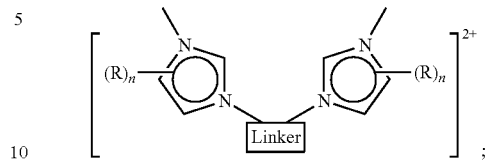

wherein
Linker is a 3, 4, 5, or 6-membered ring chiral linking group or an alicyclic four-carbon chiral linking group; and
R is independently methyl or ethyl; and
n is independently 0, 1, 2, or 3;
under conditions effective to crystallize a crystalline microporous solid that exhibits a chiral morphology and to form the enantiomerically enriched powder of claim 1.

11. The process of claim 10, wherein the conditions are conducive to forming a crystalline microporous silicate composition having STW topology.

12. The process of claim 10, wherein the hydrothermally treating is done at a temperature in a range of from about 100° C. to about 200° C. for a time effective for crystallizing the crystalline microporous solid.

13. The process of claim 10, further comprising isolating the crystalline microporous solid.

14. The process of claim 13, further comprising calcining the isolated crystalline microporous solid at a temperature in a range of from about 350° C. to about 850° C.

15. The process of claim 14, further comprising treating the calcined material with an aqueous ammonium salt.

16. The process of claim 15, further comprising treating the calcined crystalline microporous solid with at least one alkali metal cation, alkaline earth metal cation, transition metal, or transition metal oxide.

17. The enantiomerically enriched powder of claim 3, wherein R is methyl.

18. The enantiomerically enriched powder of claim 3, wherein n is 2 or 3.

19. The process of claim 10, wherein R is methyl.

20. The process of claim 10, wherein n is 2 or 3.

21. The enantiomerically enriched powder of claim 3, wherein Linker comprises a 4, 5, or 6-membered saturated cyclic chiral linking group.

22. The process of claim 10, wherein Linker comprises a 4, 5, or 6-membered saturated cyclic chiral linking group.

23. The enantiomerically enriched powder of claim 1 that exhibits an enantiomeric excess of an R-STW enantiomer of at least 50%.

24. The enantiomerically enriched powder of claim 1 that exhibits an enantiomeric excess of an R-STW enantiomer of at least 75%.

25. The enantiomerically enriched powder of claim 1 that exhibits an enantiomeric excess of an R-STW enantiomer of about 100%.

26. The enantiomerically enriched powder of claim 1 that exhibits an enantiomeric excess of an S-STW enantiomer of at least 50%.

27. The enantiomerically enriched powder of claim 1 that exhibits an enantiomeric excess of an S-STW enantiomer of at least 75%.

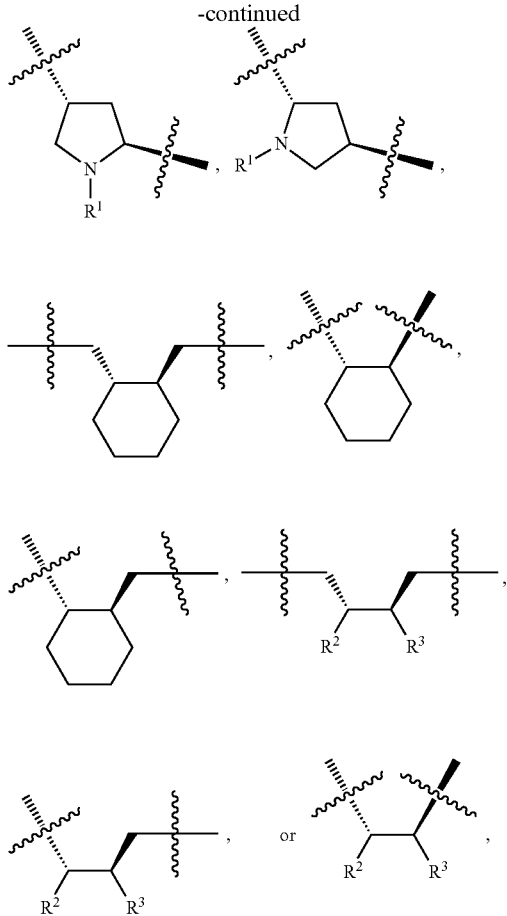

where $R^1$ is H or $C_{1-6}$alkyl, $R^2$ and $R^3$ are independently $C_{1-12}$ alkyl or aryl.

7. The enantiomerically enriched powder of claim 1, wherein the crystalline microporous solid is substantially free of occluded organic material, the crystalline microporous solid being predominantly in a hydrogen form.

8. The enantiomerically enriched powder of claim 1, wherein the crystalline microporous solid is calcined and contains a transition metal or transition metal oxide within its pores.

9. The enantiomerically enriched powder of claim 1, wherein the crystalline microporous solid is calcined and contains Li, Na, K, Rb, Cs, Be, Mg, Ca, Sr, Be, Al, Ga, In, Zn, Ag, Cu, Fe, Co, Ni, Cd, Ru, Rh, Pd, Pt, Au, Hg, La, Ce, Pr, Nd, Pm, Sm, Eu, or $R_{4-n}N^+H_n$ cations, where R is alkyl, n=0-4, in its pores.

10. A process for preparing the enantiomerically enriched powder of claim 1, the process comprising hydrothermally treating a composition comprising:
(a) at least one source of a silicon oxide;
(b) optionally at least one source of aluminum oxide, boron oxide, cerium oxide, gallium oxide, germanium oxide, hafnium oxide, iron oxide, tin oxide, titanium oxide, vanadium oxide, zinc oxide, zirconium oxide, or a combination or mixture thereof;
(c) either a source of fluoride or a source of hydroxide; and 28. The enantiomerically enriched powder of claim 1 that exhibits an enantiomeric excess of an S-STW enantiomer of about 100%.

* * * * *